United States Patent
Fefer et al.

(10) Patent No.: US 12,207,655 B2
(45) Date of Patent: Jan. 28, 2025

(54) PROTOPORPHYRIN IX DERIVATIVES AND USE THEREOF TO IMPROVE THE HEALTH OF PLANTS

(71) Applicant: NUTRIEN AG SOLUTIONS (CANADA) INC., Calgary (CA)

(72) Inventors: Michael Fefer, Mississauga (CA); Jun Liu, Mississauga (CA); Yuichi Terazono, Mississauga (CA); Kenneth Ng, Mississauga (CA); Youqing Shen, Hangzhou (CN)

(73) Assignee: NUTRIEN AG SOLUTIONS (CANADA) INC., Calgary (CA)

( * ) Notice: Subject to any disclaimer, the term of this patent is extended or adjusted under 35 U.S.C. 154(b) by 645 days.

(21) Appl. No.: 17/431,294

(22) PCT Filed: Feb. 14, 2020

(86) PCT No.: PCT/CA2020/050197
§ 371 (c)(1),
(2) Date: Aug. 16, 2021

(87) PCT Pub. No.: WO2020/163964
PCT Pub. Date: Aug. 20, 2020

(65) Prior Publication Data
US 2022/0132855 A1    May 5, 2022

Related U.S. Application Data

(60) Provisional application No. 62/806,084, filed on Feb. 15, 2019.

(51) Int. Cl.
| *A01N 55/02* | (2006.01) |
| *A01P 1/00* | (2006.01) |
| *A01P 3/00* | (2006.01) |
| *A01P 7/04* | (2006.01) |

(52) U.S. Cl.
CPC ............... *A01N 55/02* (2013.01); *A01P 1/00* (2021.08); *A01P 3/00* (2021.08); *A01P 7/04* (2021.08)

(58) Field of Classification Search
CPC . A01N 55/02; A01N 43/90; A01P 7/04; A01P 3/00; A01P 1/10
See application file for complete search history.

(56) References Cited

U.S. PATENT DOCUMENTS

| | | |
|---|---|---|
| 2,714,062 A | 7/1955 | Lockrey et al. |
| 2,786,821 A | 3/1957 | Gardner et al. |
| 2,870,037 A | 1/1959 | Converse et al. |
| 3,113,066 A | 12/1963 | Edmond |
| 3,131,119 A | 4/1964 | Fordyce et al. |
| 3,426,126 A | 2/1969 | Thorne et al. |
| 3,615,799 A | 10/1971 | Gannon et al. |
| 3,689,574 A | 9/1972 | Engelhart |
| 3,799,758 A | 3/1974 | Franz |
| 3,877,921 A | 4/1975 | Timmons et al. |
| 3,948,635 A | 4/1976 | Vachette et al. |
| 3,950,265 A | 4/1976 | Albrecht et al. |
| 3,997,322 A | 12/1976 | Ratledge |
| 4,002,628 A | 1/1977 | Benefiel et al. |
| 4,015,970 A | 4/1977 | Hennart |
| 4,041,164 A | 8/1977 | Albrecht et al. |
| 4,094,845 A | 6/1978 | De Long |
| 4,124,720 A | 11/1978 | Wenmaekers |
| 4,243,405 A | 1/1981 | Balasubramanyan et al. |
| 4,431,554 A | 2/1984 | Baur |
| 4,584,013 A | 4/1986 | Brunner |
| 4,618,360 A | 10/1986 | Brunner |
| 4,693,745 A | 9/1987 | Brunner |
| 4,698,334 A | 10/1987 | Horriere et al. |
| 4,734,432 A | 3/1988 | Szego et al. |
| 4,737,515 A | 4/1988 | Hallenbach et al. |
| 4,761,423 A | 8/1988 | Szego et al. |
| 4,826,863 A | 5/1989 | Szego et al. |
| 4,834,908 A | 5/1989 | Hazen et al. |

(Continued)

FOREIGN PATENT DOCUMENTS

| CA | 964482 | 3/1975 |
| CA | 2069311 | 4/1991 |

(Continued)

OTHER PUBLICATIONS

"Addendum 9. Northeastern Collegiate Weed Science Contest Weed, Crop, and Herbicide Lists," revised May 2007. Retrieved from the Internet: <URL: http://www.newss.org/docs/mop/addendum-9.pdf>, 7 pages.

(Continued)

*Primary Examiner* — Zohreh A Fay
(74) *Attorney, Agent, or Firm* — FAEGRE DRINKER BIDDLE & REATH

(57) ABSTRACT

Provided herein are compounds of general Formula I:

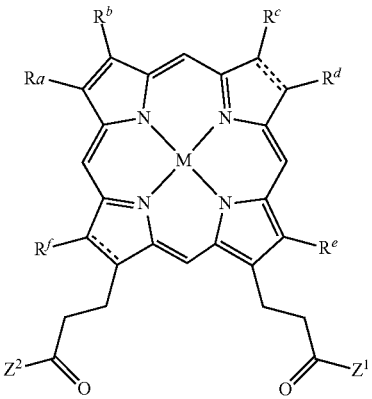

Formula I or agriculturally acceptable salts thereof. The compounds of Formula I can be used to improve the health of plants. For example, the compounds of Formula I can be used to inhibit a microbial pathogen of a plant, or to increase resistance of a plant to one or more abiotic stress.

20 Claims, No Drawings

(56) References Cited

U.S. PATENT DOCUMENTS

| | | |
|---|---|---|
| 4,844,756 A | 7/1989 | Forsberg |
| 4,853,026 A | 8/1989 | Frisch et al. |
| 4,902,333 A | 2/1990 | Quimby, Jr. |
| 4,971,840 A | 11/1990 | Boho et al. |
| 5,002,962 A | 3/1991 | Pandey et al. |
| 5,084,087 A | 1/1992 | Hazen et al. |
| 5,102,442 A | 4/1992 | Hazen et al. |
| 5,106,872 A | 4/1992 | Alder et al. |
| 5,137,726 A | 8/1992 | Ogawa |
| 5,178,795 A | 1/1993 | Roberts |
| 5,185,151 A | 2/1993 | Young |
| 5,206,021 A | 4/1993 | Dookhith |
| 5,229,356 A | 7/1993 | Tocker |
| 5,238,604 A | 8/1993 | Hazen et al. |
| 5,242,892 A | 9/1993 | Rebeiz |
| 5,300,526 A | 4/1994 | Rebeiz et al. |
| 5,308,827 A | 5/1994 | Sakamoto et al. |
| 5,330,995 A | 7/1994 | Eicken et al. |
| 5,336,661 A | 8/1994 | Lucas |
| 5,352,729 A | 10/1994 | Birkhofer et al. |
| 5,362,167 A | 11/1994 | Loftin |
| 5,393,770 A | 2/1995 | Grayson |
| 5,393,791 A | 2/1995 | Roberts |
| 5,409,885 A | 4/1995 | Derian et al. |
| 5,504,054 A | 4/1996 | Murphy |
| 5,547,918 A | 8/1996 | Newton et al. |
| 5,558,806 A | 9/1996 | Policello et al. |
| 5,580,567 A | 12/1996 | Roberts |
| 5,599,768 A | 2/1997 | Hermansky |
| 5,599,804 A | 2/1997 | Mudge |
| 5,614,203 A | 3/1997 | Dezur |
| 5,643,852 A | 7/1997 | Lucas et al. |
| 5,658,851 A | 8/1997 | Murphy et al. |
| 5,665,672 A | 9/1997 | Lucas |
| 5,668,086 A | 9/1997 | Tadayuki et al. |
| 5,703,016 A | 12/1997 | Magin et al. |
| 5,739,371 A | 4/1998 | O'Lenick, Jr. |
| 5,741,502 A | 4/1998 | Roberts |
| 5,913,884 A | 6/1999 | Trauner et al. |
| 5,919,858 A | 7/1999 | Loftin |
| 5,958,104 A | 9/1999 | Nonomura et al. |
| 5,976,535 A | 11/1999 | Fritzberg et al. |
| 5,989,331 A | 11/1999 | Bauer et al. |
| 6,015,897 A | 1/2000 | Theodore et al. |
| 6,033,647 A | 3/2000 | Touzan et al. |
| 6,036,941 A | 3/2000 | Bottiroli et al. |
| 6,117,820 A | 9/2000 | Cutler et al. |
| 6,123,923 A | 9/2000 | Unger et al. |
| 6,146,652 A | 11/2000 | Gore et al. |
| 6,159,900 A | 12/2000 | Bieringer et al. |
| 6,162,763 A | 12/2000 | Tateno |
| 6,210,656 B1 | 4/2001 | Touzan et al. |
| 6,217,869 B1 | 4/2001 | Meyer et al. |
| 6,221,811 B1 | 4/2001 | Policello et al. |
| 6,329,321 B2 | 12/2001 | Okura et al. |
| 6,403,061 B1 | 6/2002 | Candau et al. |
| 6,416,748 B1 | 7/2002 | Candau et al. |
| 6,432,877 B2 | 8/2002 | Okura et al. |
| 6,498,945 B1 | 12/2002 | Alfheim et al. |
| 6,515,031 B2 | 2/2003 | Fefer |
| 6,573,258 B2 | 6/2003 | Bommer et al. |
| 6,673,360 B2 | 1/2004 | Fefer |
| 6,683,030 B2 | 1/2004 | Kober et al. |
| 6,713,518 B1 | 3/2004 | Bessette et al. |
| 6,727,205 B2 | 4/2004 | Brinkman |
| 6,734,202 B2 | 5/2004 | Cotter et al. |
| 6,803,345 B2 | 10/2004 | Herold et al. |
| 6,878,674 B2 | 4/2005 | Kobayashi |
| 6,972,273 B2 | 12/2005 | Sedun et al. |
| 7,135,435 B2 | 11/2006 | Cooper et al. |
| 7,166,725 B2 | 1/2007 | Fang et al. |
| 7,384,927 B2 | 6/2008 | Iori |
| 7,799,343 B2 | 9/2010 | Loughner |
| 7,923,452 B2 | 4/2011 | Birner et al. |
| RE42,394 E | 5/2011 | Mudge |
| 8,076,267 B2 | 12/2011 | Diebold et al. |
| 8,153,558 B2 | 4/2012 | Norton et al. |
| 8,298,990 B2 | 10/2012 | Wu et al. |
| 8,426,343 B2 | 4/2013 | Norton et al. |
| 8,449,917 B2 | 5/2013 | Dave et al. |
| 8,569,210 B2 | 10/2013 | Fefer et al. |
| 8,633,311 B2 | 1/2014 | Bommer et al. |
| 8,747,874 B2 | 6/2014 | Fefer |
| 8,748,342 B2 | 6/2014 | Gewehr et al. |
| 8,853,128 B2 | 10/2014 | Fefer et al. |
| 9,044,008 B2 | 6/2015 | Fefer |
| 9,226,504 B2 | 1/2016 | Fefer et al. |
| 9,357,768 B2 | 6/2016 | Fefer et al. |
| 9,451,773 B2 | 9/2016 | Fefer et al. |
| 9,485,988 B2 | 11/2016 | Fefer et al. |
| 9,750,249 B2 | 9/2017 | Fefer |
| 9,801,369 B2 | 10/2017 | Fefer et al. |
| 9,826,738 B2 | 11/2017 | Fefer et al. |
| 9,999,219 B2 | 6/2018 | Fefer |
| 2001/0008873 A1 | 7/2001 | Shafer et al. |
| 2001/0019728 A1 | 9/2001 | Basinger et al. |
| 2001/0044381 A1 | 11/2001 | Dean |
| 2002/0098161 A1 | 7/2002 | Uhrich |
| 2002/0137901 A1 | 9/2002 | Cavanaugh |
| 2002/0161057 A1 | 10/2002 | Fefer |
| 2002/0183245 A1 | 12/2002 | Hasan et al. |
| 2003/0050296 A1 | 3/2003 | Boomer et al. |
| 2003/0087764 A1 | 5/2003 | Pallas et al. |
| 2003/0185754 A1 | 10/2003 | Cohen et al. |
| 2003/0187079 A1 | 10/2003 | Fefer |
| 2003/0194454 A1 | 10/2003 | Bessette et al. |
| 2003/0198659 A1 | 10/2003 | Hoffmann et al. |
| 2003/0198696 A1 | 10/2003 | Keen |
| 2004/0132621 A1 | 7/2004 | Frisch et al. |
| 2004/0132622 A1 | 7/2004 | Stewart |
| 2004/0151749 A1 | 8/2004 | Hasebe et al. |
| 2004/0162239 A1 | 8/2004 | Allan et al. |
| 2004/0167034 A1 | 8/2004 | Coote et al. |
| 2004/0192556 A1 | 9/2004 | Schregenberger et al. |
| 2004/0237133 A1 | 11/2004 | Goldman |
| 2004/0266748 A1 | 12/2004 | Robinson et al. |
| 2005/0020559 A1 | 1/2005 | Robinson et al. |
| 2005/0026786 A1 | 2/2005 | Deckwer et al. |
| 2005/0074414 A1 | 4/2005 | Tamarkin et al. |
| 2005/0181949 A1 | 8/2005 | Norton et al. |
| 2005/0202102 A1 | 9/2005 | Miller |
| 2005/0233907 A1 | 10/2005 | Nabors et al. |
| 2005/0244357 A1 | 11/2005 | Sieverding |
| 2005/0261379 A1 | 11/2005 | Fefer |
| 2005/0274164 A1 | 12/2005 | Coates et al. |
| 2006/0063676 A1 | 3/2006 | Brigance et al. |
| 2006/0068991 A1 | 3/2006 | Norton et al. |
| 2006/0105974 A1 | 5/2006 | Lange et al. |
| 2006/0194699 A1 | 8/2006 | Moucharafieh et al. |
| 2006/0276339 A1 | 12/2006 | Windsor et al. |
| 2006/0282961 A1 | 12/2006 | Hughes |
| 2006/0293188 A1 | 12/2006 | Norton et al. |
| 2007/0148200 A1 | 6/2007 | Stringfellow |
| 2007/0184005 A1 | 8/2007 | Policello et al. |
| 2007/0197386 A1 | 8/2007 | Diebold et al. |
| 2007/0197387 A1 | 8/2007 | Polge |
| 2007/0213500 A1 | 9/2007 | Uhrich |
| 2007/0264297 A1 | 11/2007 | Sciadone |
| 2007/0281878 A1 | 12/2007 | Gottschalk-Gaudig et al. |
| 2007/0287720 A1 | 12/2007 | Royalty et al. |
| 2008/0064601 A1 | 3/2008 | Casanello et al. |
| 2008/0085832 A1 | 4/2008 | Fefer et al. |
| 2008/0112909 A1 | 5/2008 | Faler et al. |
| 2008/0153702 A1 | 6/2008 | Voeste et al. |
| 2008/0161367 A1 | 7/2008 | Voeste et al. |
| 2008/0193431 A1 | 8/2008 | Zheng et al. |
| 2008/0194704 A1 | 8/2008 | Bhatnagar et al. |
| 2008/0274888 A1 | 11/2008 | Goldstein |
| 2008/0280763 A1 | 11/2008 | Hodge et al. |
| 2008/0281091 A1 | 11/2008 | Brundish et al. |
| 2008/0293567 A1 | 11/2008 | Birner et al. |
| 2009/0092986 A1 | 4/2009 | Taing et al. |
| 2009/0175873 A1 | 7/2009 | Liu |
| 2009/0215851 A1 | 8/2009 | Van Der Haas et al. |

(56) References Cited

U.S. PATENT DOCUMENTS

| | | | |
|---|---|---|---|
| 2009/0220430 A1 | 9/2009 | Rajopadhye et al. |
| 2009/0325922 A1 | 12/2009 | Fefer et al. |
| 2010/0009970 A1 | 1/2010 | Johansen et al. |
| 2010/0016447 A1 | 1/2010 | Fefer |
| 2010/0323897 A1 | 2/2010 | Burke |
| 2010/0099567 A1 | 4/2010 | Shinichi |
| 2010/0218282 A1 | 8/2010 | Nguyen et al. |
| 2010/0228343 A1 | 9/2010 | Brandom et al. |
| 2010/0251416 A1 | 9/2010 | Puzio et al. |
| 2010/0292202 A1 | 11/2010 | Vanderberg |
| 2010/0310617 A1 | 12/2010 | Zhang et al. |
| 2010/0317527 A1 | 12/2010 | Takeuchi et al. |
| 2011/0269628 A1 | 11/2011 | Gewehr et al. |
| 2011/0275516 A1 | 11/2011 | Wu et al. |
| 2011/0306495 A1 | 12/2011 | Sanaraheewa et al. |
| 2012/0070377 A1 | 3/2012 | Yahioglu et al. |
| 2012/0108431 A1 | 5/2012 | Williams |
| 2012/0149572 A1 | 6/2012 | Gewehr et al. |
| 2012/0197179 A1 | 8/2012 | Khan et al. |
| 2012/0245232 A1 | 9/2012 | Bousque et al. |
| 2013/0172185 A1 | 7/2013 | Wei |
| 2013/0224874 A1 | 8/2013 | Vinogradov et al. |
| 2013/0231604 A1 | 9/2013 | Jones et al. |
| 2013/0253016 A1 | 9/2013 | Fefer et al. |
| 2013/0296370 A1 | 11/2013 | Di Martino et al. |
| 2013/0303374 A1 | 11/2013 | Fefer et al. |
| 2013/0324620 A1 | 12/2013 | Fefer |
| 2014/0066449 A1 | 3/2014 | Stewart |
| 2014/0107070 A1 | 4/2014 | Fefer et al. |
| 2014/0228218 A1 | 8/2014 | Fefer et al. |
| 2014/0256556 A1 | 9/2014 | Fefer et al. |
| 2015/0065475 A1 | 3/2015 | Fefer et al. |
| 2015/0225723 A1 | 8/2015 | Na et al. |
| 2015/0237869 A1 | 8/2015 | Fefer |
| 2015/0296801 A1 | 10/2015 | Brahm et al. |
| 2015/0305329 A1 | 10/2015 | Fefer |
| 2016/0073634 A1 | 3/2016 | Hasan et al. |
| 2016/0150783 A1 | 6/2016 | Fefer et al. |
| 2016/0177028 A1 | 6/2016 | Bolikal et al. |
| 2016/0198723 A1 | 7/2016 | Fefer |
| 2016/0205925 A1 | 7/2016 | Nisnevitch et al. |
| 2016/0243172 A1 | 8/2016 | Cook et al. |
| 2016/0286801 A1 | 10/2016 | Liu et al. |
| 2017/0037427 A1 | 2/2017 | Evdokimov et al. |
| 2017/0071201 A1 | 3/2017 | Fefer et al. |
| 2017/0119908 A1 | 5/2017 | Rajopadhye et al. |
| 2017/0119913 A1 | 5/2017 | Osterkamp et al. |
| 2017/0223951 A1 | 8/2017 | Fefer et al. |
| 2017/0295793 A1 | 10/2017 | Chang et al. |
| 2018/0092353 A1 | 4/2018 | Fefer |
| 2020/0253211 A1 | 8/2020 | Fefer et al. |
| 2021/0068392 A1 | 3/2021 | Fefer et al. |
| 2021/0352889 A1 | 11/2021 | Fefer |
| 2022/0046920 A1 | 2/2022 | Liu et al. |
| 2022/0089615 A1 | 3/2022 | Fefer et al. |
| 2022/0132856 A1 | 5/2022 | Fefer et al. |
| 2023/0128730 A1 | 4/2023 | Ng et al. |

FOREIGN PATENT DOCUMENTS

| | | |
|---|---|---|
| CA | 1338855 | 1/1997 |
| CA | 2333175 | 12/1999 |
| CA | 2434848 | 8/2002 |
| CA | 2459928 | 4/2003 |
| CA | 2507482 | 5/2005 |
| CA | 2496142 | 8/2005 |
| CA | 2472806 | 11/2005 |
| CA | 2568817 | 12/2005 |
| CA | 2209920 | 1/2007 |
| CA | 2634630 | 7/2007 |
| CA | 2562718 | 4/2008 |
| CA | 2605092 | 4/2008 |
| CA | 2625415 | 9/2008 |
| CA | 2701764 | 4/2009 |
| CA | 2702811 | 4/2009 |
| CA | 2711660 | 7/2009 |
| CA | 2748084 | 7/2010 |
| CA | 2833190 | 11/2012 |
| CA | 2839775 | 6/2013 |
| CA | 3019623 | 10/2017 |
| CN | 1250471 | 4/2000 |
| CN | 1558760 | 12/2004 |
| CN | 101238820 | 8/2008 |
| CN | 101304658 | 11/2008 |
| CN | 101390517 | 3/2009 |
| CN | 101415327 | 4/2009 |
| CN | 101473849 | 7/2009 |
| CN | 101998827 | 3/2011 |
| CN | 102273467 | 6/2011 |
| CN | 102245027 | 11/2011 |
| CN | 102270836 | 10/2012 |
| CN | 101773113 | 2/2013 |
| CN | 102285992 | 12/2013 |
| CN | 104513250 | 4/2015 |
| CN | 105111219 | 12/2015 |
| CN | 105555312 | 5/2016 |
| CN | 105601638 | 5/2016 |
| CN | 105748439 | 7/2016 |
| CN | 107417706 | 7/2019 |
| DE | 2511077 | 9/1976 |
| EP | 0233701 | 8/1987 |
| EP | 0267778 | 5/1988 |
| EP | 0498231 | 8/1992 |
| EP | 0526206 | 2/1993 |
| EP | 0598515 | 5/1994 |
| EP | 0733066 | 9/1996 |
| EP | 0862857 | 9/1998 |
| EP | 1563734 | 8/2005 |
| EP | 1976861 | 10/2008 |
| EP | 2240767 | 10/2010 |
| EP | 2319484 | 5/2011 |
| EP | 2943072 | 11/2015 |
| EP | 2954933 | 12/2015 |
| EP | 2954934 | 12/2015 |
| EP | 3142684 | 3/2017 |
| EP | 3237487 | 11/2017 |
| GB | 191208748 | 4/1913 |
| GB | 19295 | 1/1914 |
| GB | 745360 | 2/1956 |
| GB | 747909 | 4/1956 |
| GB | 748422 | 5/1956 |
| GB | 753976 | 8/1956 |
| GB | 758926 | 10/1956 |
| GB | 762866 | 12/1956 |
| GB | 763246 | 12/1956 |
| GB | 765459 | 1/1957 |
| GB | 792045 | 3/1958 |
| GB | 1044895 | 10/1966 |
| GB | 1168913 | 10/1969 |
| GB | 1249674 | 10/1971 |
| GB | 1417364 | 12/1975 |
| GB | 1499397 | 2/1978 |
| GB | 2123819 | 2/1984 |
| GB | 2176493 | 12/1986 |
| JP | 50-063141 | 5/1975 |
| JP | 54-036205 | 11/1979 |
| JP | 55-129213 | 10/1980 |
| JP | 57-028184 | 2/1982 |
| JP | 59-067205 | 4/1984 |
| JP | 59-210007 | 11/1984 |
| JP | S62-240601 | 10/1987 |
| JP | 2-138376 | 5/1990 |
| JP | 3-183505 | 8/1991 |
| JP | 3-221576 | 9/1991 |
| JP | 4-128003 | 4/1992 |
| JP | 1910962 | 3/1995 |
| JP | 07-179306 | 7/1995 |
| JP | 2056091 | 5/1996 |
| JP | 8-218225 | 8/1996 |
| JP | 10-029901 | 2/1998 |
| JP | 11-137084 | 5/1999 |
| JP | 11-349588 | 12/1999 |
| JP | 2006-124337 | 5/2006 |
| JP | 2008-502640 | 1/2008 |

(56) References Cited

FOREIGN PATENT DOCUMENTS

| | | |
|---|---|---|
| NL | 8900381 | 9/1990 |
| NO | 151687 | 2/1985 |
| SU | 1021415 | 6/1983 |
| WO | WO 1990007272 | 7/1990 |
| WO | WO 1993012175 | 6/1993 |
| WO | WO 1996021353 | 7/1996 |
| WO | WO 1996032010 | 10/1996 |
| WO | WO 1996032011 | 10/1996 |
| WO | WO 1998035561 | 8/1998 |
| WO | WO 1999063900 | 12/1999 |
| WO | WO 2000064257 | 11/2000 |
| WO | WO 2002021913 | 3/2002 |
| WO | WO 2002034047 | 5/2002 |
| WO | WO 2002089573 | 11/2002 |
| WO | WO 2002096199 | 12/2002 |
| WO | WO 2003047558 | 6/2003 |
| WO | WO 2003101195 | 12/2003 |
| WO | WO 2003105587 | 12/2003 |
| WO | WO 2004030641 | 4/2004 |
| WO | WO 2004080177 | 9/2004 |
| WO | WO 2005009132 | 2/2005 |
| WO | WO 2005018324 | 3/2005 |
| WO | WO 2005048944 | 6/2005 |
| WO | WO 2005055716 | 6/2005 |
| WO | WO 2005082137 | 9/2005 |
| WO | WO 2005123105 | 12/2005 |
| WO | WO 2006126211 | 11/2006 |
| WO | WO 2007054473 | 3/2007 |
| WO | WO 2007117720 | 10/2007 |
| WO | WO 2007136597 | 11/2007 |
| WO | WO 2008014185 | 1/2008 |
| WO | WO 2008020872 | 2/2008 |
| WO | WO 2008030753 | 3/2008 |
| WO | WO 2008049192 | 5/2008 |
| WO | WO-2008049335 A1 * 5/2008 ............... A01N 3/02 |
| WO | WO 2008069990 | 6/2008 |
| WO | WO 2008073397 | 6/2008 |
| WO | WO 2009080428 | 7/2009 |
| WO | WO 2009090181 | 7/2009 |
| WO | WO 2009098223 | 8/2009 |
| WO | WO 2009126370 | 10/2009 |
| WO | WO 2009137062 | 11/2009 |
| WO | WO 2009139106 | 11/2009 |
| WO | WO 2009155693 | 12/2009 |
| WO | WO 2010014728 | 2/2010 |
| WO | WO 2010043447 | 4/2010 |
| WO | WO 2010132169 | 11/2010 |
| WO | WO 2011028987 | 3/2011 |
| WO | WO 2011070503 | 6/2011 |
| WO | WO 2011075805 | 6/2011 |
| WO | WO 2012031355 | 3/2012 |
| SU | WO 2012040804 | 4/2012 |
| WO | WO 2012055991 | 5/2012 |
| WO | WO 2012126094 | 9/2012 |
| WO | WO 2012162844 | 12/2012 |
| WO | WO 2012162846 | 12/2012 |
| WO | WO 2012171126 | 12/2012 |
| WO | WO 2013073998 | 3/2013 |
| WO | WO 2013078546 | 6/2013 |
| WO | WO 2013130510 | 9/2013 |
| WO | WO 2013192521 | 12/2013 |
| WO | WO 2014139012 | 9/2014 |
| WO | WO 2015081441 | 6/2015 |
| WO | WO 2015106770 | 7/2015 |
| WO | WO 2017035582 | 3/2017 |
| WO | WO 2018135882 | 7/2018 |
| WO | WO 2019033216 | 2/2019 |
| WO | WO 2019210403 | 11/2019 |
| WO | WO 2020150831 | 7/2020 |
| WO | WO 2020163964 | 8/2020 |
| WO | WO 2020163965 | 8/2020 |

OTHER PUBLICATIONS

"An Online Guide to Plant Disease Control," Oregon State University Extension, print 1954, web 1996. Retrieved from the Internet: <URL: http:/plant-disease.orst.edu/>, 7 pages.

"Auxin," Wikipedia [online]. Retrieved from the Internet: <URL: http://en.wikipedia.org/wiki/Auxin>, 12 pages, Retrieved on Apr. 9, 2015.

"Bentgrass Dead Spot: Ophiosphaerella agrostis," Cornell University, created Apr. 2001, updated Jan. 2015. Retrieved from the Internet: <URL: http://plantclinic.cornell.edu/factsheets/bentgrassdeadspot.pdf>, 2 pages.

"Biological/Biorational Products for Disease Management," University of Connecticut Integrated Pest Management, [online] Jan. 2006. Retrieved from the Internet: <URL: http://www.ipm.uconn.edu/ipm/greenhs/htms/biofung.htm>, 6 pages.

"Characteristics of Plant Growth Regulators used in Fine Turf," Clemson University, retrieved on Aug. 24, 2011. Retrieved from the Internet: <URL: http://www.clemson.edu/extension/horticulture/turf/pest-guidelines/2011-p- est-guidelines/plantgrowth-reg-201 1.pdf>, 9 pages.

"Chemical Update: Plant growth regulators," Grounds Maintenance [online] 2008. Retrieved from the Internet: <URL: http://www.grounds-mag.com/mag/grounds_maintenance_chemical_update plant_6>, 2 pages.

"Civitas Technical Bulletin—Fungicide Resistance," Petro-Canada. Retrieved from the Internet: <URL: http://www.civitasturf.com/pdf/techBulletin.pdf>, 2 pages, 2009.

"Deformulation of RD 7212 Grazz Greenzit," 5 pages, 2009.

"Dollar Spot on Turfgrass," Cornell University, Retrieved on Aug. 22, 2011. Retrieved from the Internet: <URL: http://counties.cce.cornell.edu/wyoming/agriculture/resources/ipd/dollar_spot_turfgrass.htm>, 3 pages.

"Emerald® Fungicide A Better Standard For Dollar Spot Control," Jan. 1, 2007 [retrieved on Jan. 14, 2014]. Retrieved from the Internet <URL: http://betterturf.basf.us/products/related-documents/emerald-info-sheet.pdf>, 2 pages.

"Food, Crop & Livestock Safety: Phytotoxicity," British Columbia Ministry of Agriculture. Archived Oct. 27, 2005. Retrieved from the Internet: <URL: http://www.agf.gov.bc.ca/pesticides/e_10.htm>, 2 pages.

"Fungicide Synergy," Kansas State University, Feb. 26, 2009. Retrieved from the Internet: <URL: http://www.ksuturf.com/LISTServArchive/2009-02-26-Fungicide-Synergy.pdf>, 3 pages.

"Gray leaf spot of perennial ryegrass," Kansas State University Turfgrass Research, 4 pages, revised Aug. 2008.

"Heat Stress Study Using Greenzit Pigment," University of Guelph, 3 pages, 2009.

"Herbicide Recommendations for Turfgrass: Postemergence Broadleaf Herbicides," Ontario Ministry of Agriculture, Food and Rural Affairs, Nov. 25, 2002, reviewed May 15, 2006. Retrieved from the Internet: <URL: http://www.omafra.gov.on.ca/english/crops/pub75/17turpbh.htm>, 7 pages.

"Herbicide," Wikipedia [online], retrieved on Aug. 29, 2006. Retrieved from the Internet: <http://en.wikipedia.org/wiki/Herbicide>, 5 pages.

"Horticultural Oils," IPM of Alaska [online] retrieved on Apr. 5, 2005. Retrieved from the Internet: <URL: http:/www.ipmofalaska.com/filed/hortoils.html>, 3 pages.

"Inert (other) Pesticide Ingredients in Pesticide Products," U.S. Environment Protection Agency, retrieved Sep. 11, 2007. Retrieved from the Internet: <http://www.epa.gov/opprd001/inerts/lists.html> 3 pages.

"It pays to be pure," Retrieved from the Internet: <http://www.findarticles.com/p/articles/mi-qa3824/is-200405/ai-n9424665/print>, Meister Media Worldwide, 1 pages, May 2004.

"Kannar Product Range Turf Enhancing Products," 1 page. Retrieved on Dec. 14, 2007. Retrieved from the Internet: <URL: http://web.archive.org/web/20040101182326/http:kannar.com/>, 1 page.

"Leaf Spot and Melting-out (crown and root rot) Diseases," Center for Turfgrass Science, Penn State College of Agricultural Sciences, retrieved on Aug. 30, 2011. Retrieved from the Internet: <URL: http://cropsoil.psu.edu/turf/extension/factsheets/managing-diseases/leaf-spot>, 2 pages.

(56) References Cited

OTHER PUBLICATIONS

"Performance of generic phosphite fungicides: A status report," AgNet Mar. 8, 2004, The Canadian Phytopathological Society, Retrieved from the Internet: <URL: http://www.cps-scp.ca/pathologynews/performanceofgenericfungicides.html>, 2 pages.
"Plant Growth Regulators for Turf, Landscape and Garden," Lawn Care Academy [online], retrieved Dec. 28, 2010. Retrieved from the Internet: <URL: http://www.lawn-care-academy.com/plant-growth-regulators.html>, 6 pages.
"The National Turfgrass Research Initiative: Enhancing America's Beauty Protecting America's Natural Resources Ensuring the Health and Safety of all Americans," Retrieved from the Internet: <URL: http://www.ntep.org/pdf/turfinitiative.pdf>, Apr. 2003, 22 pages.
"The Stylet-Oil User's Guide," Retrieved from the Internet: <URL: http://www.stylet-oil.com>, 15 pages. Retrieved on Mar. 22, 2005.
"Trinexapac-ethyl—Compound Summary," PubChem Public Chemical Database, [online] retrieved on Aug. 25, 2011. Retrieved from the Internet: <URL: http://pubchem.ncbi.nlm.nih.gov/summary/summary.cgi?cid=92421&loc=ec_rcs>, 3 pages.
"Turf grass coloration using hexadentate cobalt phthalocyanine amine complex salts," AN-1976-74211X[40], p. 1, 1975.
"Turfgrass Diseases: Leaf Spots and Tip Blights, Melting Out, Crown and Root Rots," University of Rhode Island Landscape Horticulture Program, 2000. Retrieved from the Internet: <URL: http://www.uri.edu/ce/factsheets/prints/leafspotsetcprint.html>, 3 pages.
"Turfgrass Pest Management Manual: A Guide to Major Turfgrass Pests & Turfgrasses," North Carolina State University, Mar. 26, 2007. Retrieved from the Internet: <URL: http://www.turfiles.ncsu.edu/PDFFiles/004041/Turfgrass_Pest_Management_Manual_A_Guide_to_Major_Turfgrass_Pests_and_Turfgrasses.pdf>, 106 pages.
Aerosil 200, Evonik [online] <URL: http://www.aerosil.com/lpa-productfinder/page/productsbytext/detail.html?pid=1855&langen>, Jun. 19, 2012, 1 page.
Agnello, "Petroleum-derived spray oils: chemistry, history, refining and formulation," in Beattie, G.A.C., Watson, D.M., Stevens, M., Spooner-Hart, R. and Rae, D.J. (eds). Spray Oils Beyond 2000—Sustainable Pest & Disease Management. University of Western Sydney, 2002. Retrieved from the Internet: <URL: http://web.entomology.cornell.edu/agnello/assets/1-1_Agnello.pdf>, 17 pages.
Agri Star, Dicamba DMA Salt Label, May 2005, 28 pages.
agrilife.org [online], "Adjuvant", 2013, retrieved on May 27, 2022, retrieved from <URL: http://agrilife.org/fisheries2/files/2013/09/Adjuvants.pdf<, 3 pages.
Ahmed et al., "Side effects of Benomyl (Fungicide) Treatments on Sunflower, Cotton and Cowpea plants," Phyton (Austria), Sep. 30, 1983, 23(2):185-195.
Alligare 2,4-D Amine Label, Feb. 2001.
Anderson et al., "Antagonistic Interation betweeen Abscisic Acid and Jasmonate-Ethylene Signaling Pathways Modulates Defense Gene Expression and Disease Resistance in *Arabidopsis*," Dec. 2004, The Plant Cell, 16:3460-3479.
Arysta Life Science, "Banvel Herbicide," retrieved on Nov. 23, 2016, http://www.cdms.net/LDat/ld279008.pdf , 29 pages.
Audenaert et al., "Abscisic Acid Determines Basal Susceptibility of Tomato to Botrytis cinerea and Suppresses Saliccylic Acid-Deprendent Signaling Mechanisms," Plant Physiology, 2002, 128(2):491-501.
Bader et al., "Adaptation of Plants to Anthropogenic and Environmental Stresses: The Effects of Air Constituents and Plant-Protective Chemicals," Marcel Dekker, Inc. 1999, 973-1010.
Bakke, "Analysis of Issues Surrounding the Use of Spray Adjuvants with Herbicides," Dec. 2002, Revised Jan. 2007. Retrieved from the Internet: <URL: http://www.fs.usda.gov/Internet/FSE_DOCUMENTS/fsbdev3_045552.pdf>, 61 pages.
Beasley and Branham, "Trinexapac-ethyl and Paclobutrazol Affect Kentucky Bluegrass Single-Leaf Carbon Exchange Rates and Plant Growth," Crop Sci., 47:132-138, Jan. 22, 2007.
Beckerman, "Disease Management Strategies for Horticultural Crops: Using Organic Fungicides," Purdue Extension, Apr. 1, 2008 [retrieved on Sep. 29, 2014]. Retrieved from the Internet: <URL: https://www.extension.purdue.edu/extmedia/bp/bp-69-w.pdf>, 4 pages.
Bell et al., "Comparison of Turfgrass Visual Quality Ratings with Ratings Determined Using a Handheld Optical Sensor," Hortitechnology., 19(2):309-316, 2009.
Ben-Tal, "Effect of Chloro-Aluminum-Phtahalocyanine on the Growth of Lenma gibba G3," J. Plant Physiol., 135(5):635-636, 1989.
BERC Biomass Energy Resource Center, "Grass Energy Basics," 2015,6 pages.
Beresford, "DMI (demethylation inhibitor) management strategy," Prevention and management strategies., pp. 21-25, 2003.
Bhosale et al., "Supramolecular self-assembly of protoporphyrin IX amphiphiles into worm-like and particular aggregates," Supramolecular Chemistry, Mar. 1, 2011, ;23(03-04):263-268.
Bigelow et al., "Evaluation of Commercially Available Plant Growth Regulator Programs for Creeping Bentgrass Fairway Management," Retrieved from the Internet: <URL: http://www.agry.purdue.edu/turf/report/2003/Page66.pdf>, pp. 66-74, 2003.
Biology and Control of Dollar Spot Disease, Ontario Ministry of Agriculture Food & Rural Affairs, Retrieved on Aug. 22, 2011. Retrieved from the Internet: <URL: http://www.omafra.gov.on.ca/english/crops/facts/info_turfdollarspot.htm>, 3 pages.
Blenis et al., "Evaluation of Fungicides and Surfactants for Control of Fairy Rings Caused by Marasmius oreades (Bolt ex. Fr.) Fr.," HortScience, 32(6):1077-1084, 1997.
Bradley, "Some ways in which a paraffin oil impedes APHID transmission of potato virus Y," Canadian Journal of Microbiology, 9(3): 369-380, 1963.
Bremer et al., "Relationships between Normalized Difference Vegetation Index and Visual Quality in Cool-Season Turfgrass: I. Variation among Species and Cultivars," Crop Science., 51:2212-2218, 2011.
Brochure for Civitas, Petro-Canada, retrieved on Aug. 22, 2011. Retrieved from the Internet: <URL: http://www.civitasturf.com/pdf/CIVITAS-technical-brochure.pdf>, 12 pages.
Brown Patch on Turfgrass *Rhizoctonia* spp., Cornell University Department of Plant Pathology and Plant-Microbe Biology, created Aug. 1999, updated May 2011. Retrieved from the Internet: <URL: http://plantclinic.cornell.edu/factsheets/brownpatch.pdf>, 3 pages.
Brown Patch Rhizoctonia solani, University of Guelph, Nov. 27, 2003. Retrieved from the Internet: <URL: http://www.uoguelph.ca/pdc/Factsheets/PDFs/127TurfBrownPatch.pdf>, 1 page.
Brown Patch, Center for Turfgrass Science, Penn State College of Agricultural Sciences, retrieved on Aug. 30, 2011. Retrieved from the Internet: <URL: http://cropsoil.psu.edu/turf/extension/factsheets/managing-diseases/brown- -patch>, 3 pages.
Buckley et al., "An Integrated Approach to Insect Management in Turfgrass: Black Cutworm," Rutgers, The State University of New Jersey, Mar. 2010. Retrieved from the Internet: <URL: http://snyderfarm.rutgers.edu/pdfs/BlackCutworms.pdf>, 3 pages.
Bunderson et al., "Tools for Evaluating Native Grasses as Low Maintenance Turf," Hortitechnology., 19(3):626-632, 2009.
Burpee and Latin, "Reassessment of Fungicide Synergism for Control of Dollar Spot," Plant Disease, 92(4):601-606, 2008.
Burpee et al., "Interactive Effects of Plant Growth Regulators and Fungicides on Epidemics of Dollar Spot in Creeping Bentgrass," Plant Disease, 80(11):1245-1250, 1996.
Burr and Warren, "Enhancement of Herbicide Activitiy with an Isoparaffinic Oil Carrier," Weed Science, 19(6):701-705, Nov. 1971.
Burt, "Tolerance of warmseason turf grasses to herbicides," Plantation Field Laboratory Mimeo Report PFL66-1, University of Florida Digital Collections [online] Aug. 1966. Retrieved from the Internet: <URL: http://ufdc.ufl.edu//UF00076427/00001>, 11 pages.
Buss, "Insect Pest Management on Golf Courses," University of Florida. Retrieved from the Internet: <URL: http://edis.ifas.ufl.edu/in410>, 14 pages. Retrieved on Aug. 26, 2011.
Buss, "Insect Pest Management on Turfgrass," University of Florida. Retrieved from the Internet: <URL: http://edis.ifas.ufl.edu/ig001>, 13 pages. Retrieved on Aug. 26, 2011.
Butler, "Cultural practices and their effects upon turf grass growth and stress tolerance," The British and International Golf Greenkeepers Association Limited, Jul. 2006. Retrieved from the Internet:

(56) References Cited

OTHER PUBLICATIONS

<URL: http://www.bigga.org.uk/about-us/magazine/back-issues/07-2006/cultural-pray-tim-butler/00919.html>, 7 pages.
Bywater, "Plant Growth Regulators: Mode of Action," AGCSA [online] Australian Turfgrass Management vol. 3.3, Jun.-Jul. 2001. Retrieved from the Internet: <URL: http://www.agcsa.com.au/static/atm_articles/html/3_3c.html>, 3 pages.
CAS No. 117428-22-5, picoxystrobin, methyl (2E)-3-methoxy-2-{2-[6-(trifluoromethyl)-2-pyridyloxymethyl]phenyl}acrylate; methyl (2E)-3-methoxy-2-[2-({[6-(trifluoromethyl)pyridin-2-yl]oxy}methyl)phenyl]prop-2-enoate; (E)-Methyl 3-methoxy-2-(2-(((6-(trifluoromethyl)pyridin 2-yl)oxy)methyl)phenyl)acrylate; ACANTO; methyl (αE)-α-(methoxymethylene)-2-[[[6-(trifluoromethyl)-2-pyridinyl]oxy]methyl]benzeneacetate; Picoxystrobin; ZA1963; © 2013-2016, retrieved Nov. 28, 2016, http://www.molbase.com/en/precursor_117428-22-5-moldata-29033.html?synonyms=1, 1 page.
CAS No. 131807-57-3, (RS)-3-anilino-5-methyl-5-(4-phenoxyphenyl)-1,3-oxazolidine-2,4-dione; Famoxate; DPX-JE 874; 3-anilino-5-methyl-5-(4-phenoxyphenyl)-1,3 oxazolidine-2,4-dione; Famoxadone; 3-Anilino-5-methyl-5-(4 phenoxyphenyl)oxazolidine-2,4-dione; 5-methyl-5-(4-phenoxyphenyl)-3-(phenylamino)-2,4-oxazolidinedione; rac-(5R)-3-anilino-5-methyl-5-(4-phenoxyphenyl)-1,3-oxazolidine-2,4-dione; © 2013-2016, retrieved on Nov. 17, 2016, http://www.molbase.com/en/precursor_131807-57-3-moldata-3366.html?synonyms=1, 1 page.
CAS No. 133408-50-1, (E)-Metominostrobin; (2E)-2-(methoxyimino)-N-methyl-2-(2-phenoxyphenyl)acetamide; Metominofen; (E)-2-(methoxyimino)-N-methyl-2-(2-phenoxyphenyl)acetamide; Metominostrobin; ssf-126; (αE)-α-(methoxyimino)-N-methyl-2 phenoxybenzeneacetamide; metaminostrobin; © 2013-2016, retrieved on Nov. 28, 2016, http://www.molbase.com/en/precursor_133408-50-1-moldata-473468.html?synonyms=1, 1 page.
CAS No. 143390-89-0, methyl (αE)-α-(methoxyimino)-2-[(2-methylphenoxy)methyl]benzeneacetate; methyl (2E)-2-methoxyimino-2-[2-[(2-methylphenoxy)methyl]phenyl]acetate; Kresoxim-methyl; methyl (E)-methoxyimino[α-(o-tolyloxy)-o-tolyl]acetate; methyl (2E)-(methoxyimino){[(2-methylphenoxy)methyl]phenyl}acetate; © 2013-2016, retrieved on Nov. 28, 2016, http://www.molbase.com/en/precursor_143390-89-0-moldata-28515.html?synonyms=1, 1 page.
CAS No. 161326-34-7, (S)-1-Anilino-4-methyl-2-methylthio-4-phenyl-2-imidazolin-5-one; (5S)-3-anilino-5-methyl-2-methylsulfanyl-5-phenylimidazol-4-one; Fenamidone; (5S)-3-anilino-5-methyl-2-(methylsulfanyl)-5-phenyl-3,5-dihydro-4H-imidazol-4-one; (5S)-3,5-dihydro-5-methyl-2-(methylthio)-5-phenyl-3-(phenylamino)-4H-imidazol-4-one; (S)-1-anilino-4-methyl-2-methylthio-4-phenylimidazolin-5-one; © 2013-2016, retrieved on Nov. 17, 2016, http://www.molbase.com/en/precursor_161326-34-7-moldata-475051.html?synonyms=1, 1 page.
CAS No. 248593-16-0, (2E)-2-[2-[[(E)-[(3E,4E)-3,4-bis(methoxyimino)pentan-2-ylidene]aminoJoxymethyl]phenyl]-2-methoxyimino-N-methylacetamide; (2E)-2-(methoxyimino)-2-{[(3E,5E,6E)-5-(methoxyimino)-4,6-dimethyl-2,8-dioxa-3,7-diazanona-3,6-dien-1 yl]phenyl}-N-methylacetamide; Orysastrobin [ISO]; (αE)-α-(methoxyimino)-2-[(3E,5E,6E)-5-(methoxyimino)-4,6-dimethyl-2,8-dioxa-3,7-diaza-3,6-nonadienyl]-N-methylbenzeneacetamide; Orysastrobin; © 2013-2016, retrieved on Nov. 28, 2016, http://www.molbase.com/en/precursor_248593-16-0-moldata-1557223.html?synonyms=1, 1 page.
CAS No. 799247-52-2, pyribencarb; methyl {2-chloro-5-[(1E)-1-(6-methyl-2-pyridylmethoxyimino)ethyl]benzyl}carbamate; methyl [(2-chloro-5-{(1E)-N-[(6-methylpyridin-2-yl)methoxy]ethanimidoyl}phenyl)methyl]carbamate; methyl N-[2-chloro-5-[(1E)-1-[[(6 methyl-1-2-pyridinyl)methoxy]imino]ethyl]phenyl]methyl]carbamate; methyl N-[[2-chloro-5-[(Z)-C-methyl-N-[(6-methylpyridin-2-yl)methoxy]carbonimidoyl]phenyl]methyl]carbamate; © 2013-2016, retrieved on Nov. 28, 2016, http://www.molbase.com/en/precursor_799247-52-2-moldata-1607308.html?synonyms=1, 1 page.
CAS No. 850881-70-8, "Coumoxystobin; Coumoxystrobine; methyl (2E)-2-(2-{[(3-butyl-4-methyl-2-oxo-2H-1-benzopyran-7-yl)oxy]methyl}phenyl)-3-methoxyprop-2-enoate; SYP 3375," © 2013-2016, retrieved on Nov. 17, 2016, http://www.molbase.com/en/850881-70-8-moldata-2475984.html, 1 page.
CAS No. 862588-11-2, Pyraoxystrobin; Benzeneacetic acid, 2-[[[3-(4-chlorophenyl)-1-methyl-1H-pyrazol-5-yl]oxy]methyl]-a-(methoxymethylene)-, methyl ester, (aE)—(CA Index Name), STN, entered STN on Sep. 7, 2005, retrieved on Nov. 28, 2016, stnc.cas.org, 3 pages.
Cawthon and Pyle, "Use of Plant Growth Regulators to Retard Growth of Bermudagrass and Dallisgrass in the Landscape," Texas A&M University, retrieved Aug. 24, 2011. Retrieved from the Internet: URL:<http://www.tamu-commerce.edu/agscience/res-dlc/turf/pgr.html>, 5 pages.
Chase and Simone, "Phytotoxicity on Foliage Ornamentals Caused by Bactericides and Fungicides," Plant Pathology Fact Sheet, Florida Cooperative Extension Service, Institute of Food and Agricultural Sciences, University of Florida. Retrieved from the Internet: <URL: http://plantpath.ifas.ufl.edultakextpublFactSheetsippOO30.pdf>, 8 pages. Retrieved on Aug. 26, 2011.
Chemical Structures, The Bugwood Network, Nov. 7, 2002. Retrieved from the Internet: <URL: http://www.bugwood.org/PAT/22chemicalstructures.html>, 8 pages.
Chen et al., "Chlorin e6 131: 152-Anhydride: A Key Intermediate in Conjugation Reactions of Chlorin e6," European journal of organic chemistry, Jun. 2015, 2015(17):3661-3665.
Chen et al., "Rheological properties of silica particle suspensions in mineral oil," J Dispers Sci Technol., 26(6):791-798, 2005.
Christians, "Creative uses for plant growth regulators," USGA Green Sec. Rec, 39: 11-13, Sep. 2001/Oct. 2001.
Clarke et al., "Pest Control Recommendations for Lawn and Turf Areas, 2006" Rutgers NJAES Cooperative Extension, Jul. 13, 2006. Retrieved from the Internet: <URL: http://njaes.rutgers.edu/pubs/publication.asp?pid=e037>, 33 pages.
Cleary Chemical Corporation, "Use of Cleary's Grass Greenzit™," 1 page, 2004.
Cline, "OLR mating disruption just got easier," Western Farm Press [online] Jun. 1, 2001. Retrieved from the Internet: <URL: http://westernfarmpress.com/olr-mating-disruption-just-got-easier>, 4 pages.
Cockerham et al., "Evaluation of Turfgrass Growth Retardant Chemicals," California Turfgrass Culture, 23-24, 21(3):23-24, 1971.
Colby, "Calculating synergistic and antagonistic responses of herbicide combinations," Weeds, Jan. 1967, 15(1): 4 pages.
Coo-Ranger et al., "Ionic silicone surfactants in water-in-silicone oil emulsions containing proteins," Polymer Preprints, 45(1):674-675, 2004.
Cortes-Barco et al., "Comparison of induced resistance activated by benzothiadiazole,(2R, 3R)-butanediol and an isoparaffin mixture against anthracnose of Nicotiana benthamiana," Plant pathology, 59(4):643-653, 2010.
Cortes-Barco et al., "Induced systemic resistance against three foliar diseases of Agrostis stolonifera by (2R, 3R)-butanediol or an isoparaffin mixture, " Annals of Applied Biology, 157(2):179-189, 2010.
Corwin, "Integrated Pest Management: Identification & Management of Turfgrass Disease," University of Missouri Extension. Retrieved from the Internet: <URL: http://extension.missouri.edu/p/IPM1029> 56 pages, 2007.
Cranmer et al., "Controlled droplet application (CDA) of fluazifop and sethoxydim for annual and perennial weed control," 1983 Meeting of the Weed Science Society of America, 1983, 23-24, Weed Abstract vol. 033 Abs. (No. 00871).
Cranshaw, "Clover and Other Mites of Turfgrass," Colorado State University Extension. Dec. 2012. Retrieved from the Internet: <URL: http://www.ext.colostate.edu/pubs/insect/05505.html>, 2 pages.
Crocker & Simpson, "Pesticide screening test for the southern chinch bug," Journal of Economic Entomology, 74(6):730-731, 1981.
Croda, "Volpo," Croda Chemicals Europe Ltd, Jul. 2001. Retrieved from the Internet: <URL: http://www.chservice.ru/download/DC%20Volpo.pdf>, May 2004.
Cropper, "Towards Reducing Fungicide Use in the Control of Dollar Spot (Sclerotinia Homoeocarpa F.T. Bennett) Disease on Creeping Bentgrass (Agrostis Stolonifera L.)," May 4, 2009, Master of

(56) References Cited

OTHER PUBLICATIONS

Science Thesis, University of Kentucky. Retrieved from the Internet: < URL: http://archive.uky.edu/handle/10225/1044>, 69 pages.
Danneberger and Street, "Turfgrass Growth Substances," Golf Course Management, Apr. 1990, 58(4):80, 82, 86, 88,.
Datapak for SALVO herbicide, United Agri Products Canada Inc., 14 pages, Oct. 2005.
Dell et al., "The Efficacy of JMS Stylet-Oil on Grape Powdery Mildew and Botrytis Bunch Rot and Effects on Fermentation," Am. J. Enol. Vitic., 49(1): 11-16, 1998.
Deoliveira et al., "Chlorins: natural sources, synthetic developments and main applications," Current Organic Synthesis, Feb. 1, 2014, 11(1):42-58.
Derksen et al., "Spray delivery to nursery trees by air curtain and axial fan orchard sprayers," Journal of Environmental Horticulture, Mar. 2004, 22(1): 17-22, 7 pages.
Dickey, "Using plant growth regulators in turfgrass management. (Green Science).," Golfscape [online] Sept. 1, 2002. Retrieved from the Internet: < URL: http://www.highbeam.com/doc/1G1-105617663.html/print>, 2 pages.
Diesburg, "Effects of Turf Colorants and FES04 on Spring Greenup of Zoysiagrass," 1990. Retrieved from the Internet: < URL: http://www.turf.uiuc.edu/research/summaries/1990/effect_colorant.pdf>, 2 pages.
Dokkuma, "Plant Growth Regulators as a Turfgrass Management Tool," Greenkeeper [online] 2008. Retrieved from the Internet: < URL: http://www.greenkeeper.com/upload/alinea_1425.pdf>, 4 pages.
Dokkuma, Plant Growth Regulators Used in Turfgrass Management, Greenkeeper [online] 2008. Retrieved from the Internet :< URL:http://www.greenkeeper.eu/upload/alinea_1420.pdf>, 4 pages.
Duell, "Turfgrass quality and phytotoxicity affected by growth retardants," Chapter 70. Retrieved from the Internet: < URL: http://archive.lib.msu.edu/tic/its/articles/1985pro749.pdf>, 8 pages. Retrieved on Aug. 24, 2011.
Duke et al. "Photosensitizing Porphyrins as Herbicides," Naturally Occurring Pest Bioregulators, Jan. 9, 1991, 26(449):371-386.
Engvild, "Herbicidal activity of 4-chloroindoleacetic acid and other auxins on pea, barley and mustard," Physiologia Plantarum, 96(2):333-337, Feb. 1996.
Erhan and Nelsen, "Comparisons of volatile organic chemical content of news, sheetfed, and heatset ink formulations," Journal of the American Oil Chemists' Society, 78(4):419-422, 2001.
European Search Report in corresponding European Application No. 07866183.2, dated Jul. 24, 2013, pp. 1-7.
European Search Report in European Application No. 14763572.6-1454, dated Feb. 16, 2017, 8 pages.
Fasold, "Plant Growth Regulators: More Color, Less Clippings," Irrigation and Green Industry [online], May 15, 2009. Retrieved from the Internet: < URL: http://www.igin.com/article-925-%20plant growth regulat.html>, 4 pages.
Fässler et al., "Effects of indole-3-acetic acid (IAA) on sunflower growth and heavy metal uptake in combination with ethylene diamine disuccinic acid (Edds)," J Chemosphere, 80(8):901-907, Aug. 1, 2010.
Fertilome, "Broad Spectrum Landscape & Garden Fungicide (32 oz)," Fertilome.com [online] archived on Dec. 30, 2010. Retrieved from the Internet: < URL: http://web.archive.org/web/20101230174658/http://www.fertilome.com/product.aspx?pid=9950d7cl-dfed-4268-9474-eb508f967dc0>, 2 pages.
Fidanza et al., "Evaluation of fungicide and plant growth regulator tank-mix programmes on dollar spot severity of creeping bentgrass," Crop Protection, 25(9): 1032-1038, 2006.
Fidanza et al., "Use of a Soil Surfactant with Fungicides for Control of Fairy Ring Disease in Turfgrass," Journal of ASTM International, 4(4):77-82, 2007.
Fishel, "Plant Growth Regulators," University of Florida, Feb. 2006, Revised Apr. 2009, 5 pages.
Fungicide Resistance Action Committee [FRAC] Code List: Fungicides sorted by mode of Action, Fungicide Resistance Action Committee, retrieved on Aug. 22, 2011. Retrieved from the Internet: <URL: http://www.frac.info/frac/publication/anhang/FRAC%20Code%20List%202011final.pdf>, 10 pages.
Furuta, "Strangers in a Strange Land, " California Turfgrass Culture, 21(3):22-23, 1971.
Gaussoin and Branham, "Plant Growth Regulator Effects on Annual Bluegrass/Creeping Bentgrass Competition," Department of Crop & Soil Sciences Michigan State University, pp. 52-56, Jul. 2008. Retrieved from the Internet: < URL: http://archive.lib.msu.edu/tic/mitgc/article/198852a.pdf>.
Gauvrit and Cabanne, "Oils for weed control: Uses and mode of action," Pesticide Science, 37(2):147- 153, 1993.
Gebhardt et al., "Herbicide application with the controlled droplet applicator when using soybean oil," American Society of Agricultural Engineers, Paper No. 83-1509, 13 p. 1983.
Gilbert and Kopec, "Spring Greenup of Dormant Non-Overseeded Bermudagrass," University of Arizona College of Agriculture 2004 Turfgrass and Ornamental Research Report. Retrieved from the Internet: < URL: http://ag.arizona.edu/pubs/crops/az1359/az13593c11.pdf>, 4 pages.
Golden Artist Colors, "Pigment Identification Charts," Retrieved on Sep. 15, 2011. Retrieved from the Internet: < URL: http://www.goldenpaints.com/technicaldata/pigment.php>, 15 pages.
Gomes et al., "Photodynamic inactivation of Penicillium chrysogenum conidia by cationic porphyrins," Photochemical & Photobiological Sciences, 2011, 10(11): 1735-1743.
Goodwin and McBrydie, "Effect of surfactants on honey bee survival," New Zealand Plant Protection, 53:230-234, 2000.
Gordon's brand, Amine 400 2,4-D Weed Killer, herbicide label, 4 pages, Oct. 2015.
Grey et al., "Timed Release of Flurprimidol from a Granular Formulation in Mulches and Sand," HortScience, 44(2):512-515, 2009.
Grover et al., "Droplet and Vapor Drift from Butyl Ester and Dimethylamine Salt of 2,4-D," Weed Science, 20(4): 320-324, Jul. 1972.
Guillaumot et al., "Synergistic enhancement of tolerance mechanisms in response to photoactivation of cationic tetra (N-methylpyridyl) porphyrins in tomato plantlets," Journal of Photochemistry and Photobiology B: Biology, Mar. 1, 2016, 156:69-78.
Guo et al., "Synergistic antiproliferative effect of chemo-phototherapy: Synthesis and photodynamic activity evaluation of novel Chlorin e6-artesunate conjugates as antiproliferative agents," Bioorganic & Medicinal Chemistry Letters, Oct. 1, 2017, 4 pages.
Guy et al., "The performance of postemergence grass herbicides applied with sprinkler irrigation," Proceedings of the 39th annual meeting of the Southern Weed Science Society, p. 106, 8A, 1986.
Harmon and Latin, "Gray leaf spot of perennial ryegrass," Plant Health Progress [online]. Retrieved from the Internet: < URL: http://www.plantmanagementnetwork.org/pub/php/diagnosticguide/2003/ryegrass/>, 8 p. 2003.
Hartzler, "Role of spray adjuvants with postemergence herbicides," Iowa State University Weed Science [online], Mar. 7, 2001, Retrieved from the Internet: < URL: http:/www.weeds.iastate.edu/mgmt/2001/additives.htm>, 3 pages.
Hazen et al., "Adjuvants-Terminology, Classification, and Chemistry 1," Weed technology, Oct. 2000, 14(4): 13 pages.
Heath et al., "Chelating agents and auxin," Nature, 201(4919):585-587, Feb. 8, 1964.
Heil and Bostock, "Induced systemic resistance (ISR) against pathogens in the context of induced plant defences," Annals of Botany, 89(5), 503-512, 2002.
Hill, "Silicone surfactants-new developments," Current opinion in colloid & interface science, 7(5):255-261, 2002.
Hodgson, "Armyworms and cutworms in turfgrass," Utah State University Extension, Jun. 2007. Retrieved from the Internet: < URL: http://utahpests.usu.edu/IPM/files/uploads/PDFDocs/factsheet-pdf/armyw-cutw-turf07.pdf>, 3 pages.
Hoffman et al., "Application of Fungicides for Suppression of Fusarium Head Blight (Scab)," North Dakota State University, May 2000. Retrieved from the Internet: < URL: http://www.ag.ndsu.edu/pubs/ageng/machine/ae1148.pdf>, 4 pages.

(56) References Cited

OTHER PUBLICATIONS

Hoffman, "Analysis of Alcohol and Alkylphenol Polyethers via Packed col. Supercritical Fluid Chromatography," (Doctoral dissertation, Virginia Polytechnic Institute and State University), 2004.

Holly Frontier®, "Sunspray Oils," 2014 [retrieved on 2015-07-27]. Retrieved from the Internet: <URL: http://www.hollyfrontierlsp.com/Products/Horticultural-Oils/Sunspray-Oils/85/>, 1 page.

Horn, "Increasing the Effectiveness of Turf Herbicides by Use of Oil," Florida State Horticultural Society, pp. 499-509, 1966.

Horn, "Tolerance of Several Southern Turfgrasses to Various Spray Oils," Florida State Horticultural Society, pp. 494-499, 1966.

Hsiang and Tian, "Chemical Trials for Dollar Spot Disease Control," Summer 2006, Guelph Turfgrass Institute, 2006 Annual Research Report, Retrieved from the Internet <URL: http://131.104.104.3/06anrep/40-42.pdf>, pp. 40-42.

Hsiang et al. "Sporulation and identity of tar spot of maple in Canada," Acta Silv. Lign. Hung. Spec. Edition, (2007) 71-74.

Hsiang et al., "Baseline sensitivity and cross-resistance to demethylation-inhibiting fungicides in Ontario isolates of Sclerotinia homoeocarpa," European journal of plant pathology, 103(5):409-416, 1997.

Hsiang et al., "Sensitivity of Sclerotinia homoeocarpa to demethylation-inhibiting fungicides in Ontario, Canada, after a decade of use," Plant pathology, 56(3):500-507, 2007.

Huang, "Better Creeping Bentgrass Through Electricity," GCM, 2003, pp. 85-86. Retrieved from the Internet: < http://www2.gcsaa.org/gcm/2003/Dec. 03/pdfs/12electricity.pdf>, 2 pages.

Huang, "Plant growth regulators: What and why," Golf Course Management, pp. 157-160, Jan. 2007.

Hwang et al., "The response of seeds and seedlings to treatment with indolylacetic acid," Annals of Botany, 4(13):31-37, Jan. 1, 1940.

Jesus et al., "An insight into the photodynamic approach versus copper formulations in the control of Pseudomonas syringae pv. actinidiae in kiwi plants," Photochemical & Photobiological Sciences, 2018, 17(2): 13 pages.

Jordan, "Enhanced post-emergence herbicide efficacy with ultra-low vol. application," Proceedings of the 48th annual meeting of the Southern Weed Science Society, 48, pp. 208-212, 1995.

Jung et al., "Toxic tetrapyrrole accumulation in protoporphyrinogen IX oxidase-overexpressing transgenic rice plants," Plant molecular biology, Jul. 2008, 67(5):535-546.

Kaminski and Dernoeden, "Dead Spot Disease of Creeping Bentgrass," University of Maryland, Nov. 2003. Retrieved from the Internet: < URL: http://www.hgic.umd.edu/content/documents/TT- 14DeadSpot.pdf>, 2 pages.

Kaminski and Dernoeden, "Dead Spot of Creeping Bentgrass and Hybrid Bermudagrass," Plant Management Network [online], Apr. 19, 2005. Retrieved from the Internet: < URL: http://www.plantmanagementnetwork.org/pub/ats/diagnostic/2005/de- adspot/>, 8 pages.

Kaminski and Dernoeden, "Understanding Bentgrass Dead Spot," USGA Turfgrass and Environmental Research Online, 2(2):1-7, Jan. 15, 2003. Retrieved rom the Internet: < URL: http://turf.lib.msu.edu/tero/v02/n02.pdf>, 9 pages.

Kaminski, "Bentgrass dead spot," University of Connecticut, Dec. 2006. Retrieved from the Internet: <http://www.turf.uconn.edu/pdf/research/factsheets/Disease_Bentgrass_Dead_Spot.pdf>, 2 pages.

Knowles, D. A., "Formulation of Agrochemicals." Chemistry and Technology of Agrochemical Formulations. Springer., 41-79, 1998.

Koga et al., "Abscisic acid and low temperatures suppress the whole plant-specific resistance reaction of rice plants to the infection of Magnaporthe grisea," 2004, Physiological and Molecular Plant Pathology, 65:3-9.

Kopec et al., "Repeat Applications of Paclobutrazole (TGR) Plant Growth Regulator on Overseeded Bermudagrass Turf: Weed Control and Bermudagrass Transition," Turfgrass, Landscape and Urban IPM Research Summary, The University of Arizona. Retrieved from the Internet: <URL: http://ag.arizona.edu/pubs/crops/az1487/14875e.pdf>, pp. 174-196, Feb. 2009.

Kopeck and Gilbert, "Overseed Greens Performance Trials," 6 pp. 1995-1996.

Koppenhofer et al., "An Integrated Approach to Insect Management in Turfgrass: Sod Webworms," Rutgers, The State University of New Jersey, Mar. 2010. Retrieved from the Internet: < URL: http://snyderfarm.rutgers.edu/pdfs/SodWebworms.pdf> 3 pages.

Koppenhofer et al., "An Integrated Approach to Insect Management in Turfgrass: White Grubs," Jun. 2002. Retrieved from the Internet: < URL: https://www.co.somerset.nj.US/pdf/JapBeetleFS.pdf>, 4 pages.

Kremer et al., "Control of Sclerotinia homoeocarpa in turfgrass using effective microorganisms," EM World J, 1:16-21, 2000.

Larkin et al., "Tetrapyrrole signaling in plants," Frontiers in plant science, Oct. 19, 2016, 7(1586): 17 pages.

Latin and Stewart, "Turfgrass Disease Profiles: Gray Leaf Spot," Purdue University. Retrieved from the Internet: < URL: https://www.extension.purdue.edu/extmedia/BP/BP-107-W.pdf> Apr. 2008, 2 pages.

Latin, "Turfgrass Disease Profiles: Brown Patch," Purdue University, Retrieved from the Internet: <URL: https://www.extension.purdue.edu/extmedia/BP/BP-106-W.pdf> Apr. 2008, 2 pages.

Latin, "Turfgrass Disease Profiles: Dollar Spot," Purdue University. Retrieved from the Internet: <URL: https://www.extension.purdue.edu/extmedia/BP/BP-105-W.pdf>, Jan. 2010, 3 pages.

Latin, "Turfgrass Disease Profiles: Gray Snow Mold," Purdue University, Retrieved from the Internet: <URL: https://www.extension.purdue.edu/extmedia/BP/BP-101-W.pdf> Jan. 2006, 3 pages.

Latin, "Turfgrass Disease Profiles: Leaf Spot/Melting Out," Purdue University, Retrieved from the Internet: < http://www.ces.purdue.edu/extmedia/bp/bp-103-w.pdf>, Apr. 2008, 2 pages.

Latin, "Turfgrass Disease Profiles: Pink Snow Mold and Microdochium Patch," Purdue University, Retrieved from the Internet: < URL: https://www.extension.purdue.edu/extmedia/BP/BP-102-W.pdf>, Jan. 2006, 3 pages.

Li et a l., "Self-assembled chlorin e6 conjugated chondroitin sulfate nanodrug for photodynamic therapy," Biomacromolecules, May 9, 2011, 12(5): 1724-1730.

Lickfeldt et al., "Implications of repeated trinexapac-ethyl applications on Kentucky bluegrass," Agronomy Journal, 93(5):1164-1168, 2001.

Lincoln County Noxious Weed Control, "Herbicide Facts," 2007, Retrieved from the Internet: < URL: http://www.co.lincoln.wa.US/WeedBoard/herbicide/herbicidefacts.pdf>, 22 pages.

Liu, "Cytokinin Effects on Creeping Bentgrass Responses to Heat Stress: I. Shoot and Root Growth," Crop. Sci., 42:457-465, 2002.

Liu, "Painting dormant bermudagrass putting greens," Golf Course Manage, 75(11):86-91, 2007.

Lopez et al., "Effect of indole-3-acetic acid, kinetin, and ethylenediaminetetraacetic acid on plant growth and uptake and translocation of lead, micronutrients, and macronutrients in alfalfa plants," Int J Phytoremediation., 11(2):131-149, Feb. 13, 2009.

Lorbeer, "Synergism, Antagonism, and Additive Action of Fungicides in Mixtures," Phytopathology, 86(11):1261-1262, 1996.

Material Safety Data Sheet for AGRI-DEX, Helena Chemical Company, 1 page, Apr. 29, 2005.

Material Safety Data Sheet for Banner MAXX, Syngenta Crop Protection, Inc., 5 pages, Aug. 30, 2010.

Material Safety Data Sheet for Blendex Vhc, Helena Chemical Company, 1 page, Jul. 27, 2000.

Material Safety Data Sheet for Broadcoat Spray Adjuvant, Caltex Australia Limited, 5 pages, Sep. 2003.

Material Safety Data Sheet for Chipco Signature, Bayer CropScience Pty Ltd, May 1, 2007, 6 pages.

Material Safety Data Sheet for Chipco Signature, Bayer CropScience Pty Ltd, Oct. 21, 2002, 7 pages.

Material Safety Data Sheet for Civitas, Petro-Canada Lubricants, Inc., 6 pages, Mar. 21, 2011.

Material Safety Data Sheet for Cleary 3336 Plus, Cleary Chemical Corporation, Feb. 1, 2005, 4 pages.

Material Safety Data Sheet for Daconil 2787, Syngenta Crop Protection Canada, Inc., 7 pages, Dec. 31, 2008.

Material Safety Data Sheet for Daconil Ultrex Fungicide, Syngenta Crop Protection Canada, Inc., 7 pages, Aug. 1, 2009.

(56) References Cited

OTHER PUBLICATIONS

Material Safety Data Sheet for FORE 80 WP Rainshield, Dow AgroSciences, Jun. 1, 2001, 9 pages.
Material Safety Data Sheet for FORE Fungicide, Rohm and Haas Company, 9 pages, Oct. 16, 1995.
Material Safety Data Sheet for Grass Greenzit, W.A.Cleary Chemical Corporation, 2 pages, Oct. 1997.
Material Safety Data Sheet for Green Lawnger, Becker Underwood, Inc., 5 pages, Feb. 25, 2009.
Material Safety Data Sheet for Harmonizer, Petro-Canada Lubricants Inc., 6 pages, May 6, 2011.
Material Safety Data Sheet for JMS Stylet-Oil, 4 pages, Mar. 1, 1994.
Material Safety Data Sheet for Kannar Turfkare Green, 1 page, Sep. 18, 2007.
Material Safety Data Sheet for Killex Lawn Weed Control Concentate (Ortho), Scotts Canada Ltd., 7 pages, Sep. 13, 2005.
Material Safety Data Sheet for Lambent MFF 159-100, Lambent Technologies Corp., 3 pages, Apr. 4, 2006.
Material Safety Data Sheet for Lambent MFF-199 Sw, Lambent Technologies Corp., 3 pages, Jan. 31, 2005.
Material Safety Data Sheet for PEPTOIL, Drexel Chemical Company, 1 page, Jan. 7, 2005.
Material Safety Data Sheet for Regreen™M Turfgrass Colorant, Precision Laboratories, Inc., 3 pages, Mar. 1, 2010.
Material Safety Data Sheet for Rovral Green GT Flowable Fungicide, Bayer CropScience Inc., 9 pages, Mar. 2, 2011.
Material Safety Data Sheet for Silsurf A008-UP, Siltech Corporation, 4 pages, Aug. 21, 2009.
Material Safety Data Sheet for Sunspray 6E, Jun. 1, 2009, [retrieved on 2014-09-30]. Retrieved from the Internet: < URL: http://www.recarroll.com/cw3/Assets/product files/Sunspray 6E.pdf>, 5 pages.
Material Safety Data Sheet for Surf Ac 820, Drexel Chemical Company, 1 page, Jul. 22, 2005.
Material Safety Data Sheet for Sylgard 309 Silicone Surfactant, Dow Corning Corporation, 9 pages, Apr. 5, 2001.
McCarty and Whitwell, "Plant Growth Regulators for Fine Turf," Clemson University, South Carolina, archived Sep. 15, 2009. Retrieved from the Internet: < URL: http://www.clemson.edu/extension/horticulture/turf/pest_guidelines/growth regulators.html>, 1 page.
Mccowan, "Turf Herbicide Rx: Add Oil," Agricultural Chemicals, 23(4): 18-21, 1968.
Mccullough et al., "Ethephon and Trinexapac-ethyl Influence Creeping Bentgrass Growth, Quality, and Putting Green Performance," Plant Management Network, 2006. Retrieved from the Internet: <URL: http://www.plantmanagementnetwork.org/publats/research/2006/creeping/>, 7 pages.
Mccullough et al., "Plant Growth Regulator Regimens Reduce Poa annua Populations in Creeping Bentgrass," Plant Management Network, 6 pages, Mar. 4, 2005.
Mccullough, "Turfgrass Growth Regulators For Professional Managers," Extension Agronomist-Weed Science, Georgia Turf, retrieved Aug. 25, 2011. Retrieved from the Internet: <URL: http://commodities.caes.uga.edu/turfgrass/georgiaturf/publicat/PCRP2011/PGR.pdf>, 2 pages.
Meister, Jr., Farm Chemicals, 141(1), pp. 4, 38, 42, 44, 46, 48, 77, 78, 80, 82, 84, 86, 92, 94, 96, Jan. 1978.
Mercier, "Use of the growth regulator paclobutrazol in the management of dollar spot of creeping bentgrass in Minnesota, " Phytoprotection, 80(2):65-70, 1999.
Mergos et al., "Dielectric properties of nanopowder emulsions in paraffin oil," 2011 IEEE International Conference on Dielectric Liquids, Sep. 8, 2011.
Mitchell, "Effect of indoleacetic acid on the growth of some crop plants," Proceedings of the American Society for Horticultural Science, vol. 36, pp. 171-176, Arp. 1939.
Mittler, "Abiotic stress, the field environment and stress combination," TRENDS in Plant Science, 2006, 11(1): 15-19.

Mohr et al., "Abscisic acid influences the susceptibility of Arabidopsis thaliana to Pseudomonas syringae pv. Tomato and Peronospora parasitica," 2003, Functional Plant Biology, 30:461-469.
Mohr et al., "Suppression by ABA of salicylic acid and lignin accumulation and the expression of multiple genes, in Arabidopsis infected with Pseudomonas syringae pv. Tomato," 2007, Funct Integr Genomics, 7:181-191.
Morris, "A Guide to NTEP Turfgrass Ratings," NTEP.org [online], 2011. Retrieved from the Internet: <URL: http://www.ntep.org/reports/ratings.htm>, 5 pages.
Mueller, "Fungicides: QoI Fungicides" Iowa State University, Available from: < URL: http://www.ipm.iastate.edu/ipm/icm/2006/5-22/fungicides.html>, 2 pages.
Mueller, "Fungicides: Triazoles," Intigrated Crop Management, Iowa State University, May 30, 2006. Retrieved from the Internet: < URL: http://www.ipm.iastate.edu/ipm/icm/2006/5-30/fungicides.htm >, 3 pages.
Murphy et al., "Plant Growth Regulators Used in Turfgrass Management," Georgia Turf, Retrieved on Aug. 25, 2011. Retrieved from the Internet: <http://commodities.caes.uga.edu/turfgrass/georgiaturf/WeedMngt/weedcontrol/PGR.htm>, 10 pages.
Murphy, "Turfgrass Growth Regulators For Professional Managers," Extension Agronomist-Weed Science, Georgia Turf, retrieved Aug. 25, 2011. Retrieved from the Internet: <URL: http://commodities.caes.uga.edu/turfgrass/georgiaturf/Publicat/PCRP2009/PGR.09.pdf>, 1 page.
Nagahatenna et al., "Tetrapyrrole-based drought stress signalling," Plant biotechnology journal, May 2015, 13(4):447-459.
Nalewaja et al., "Crop origin oils with grass control herbicides." Proc. North Cent. Weed Control Conf., vol. 38, p. 3, 1983 (Abstract).
Nason et al., "Strobilurin fungicides induce changes in photosynthetic gas exchange that do not improve water use efficiency of plants grown under conditions of water stress," Pest management Science, 2007, 63:1191-1200.
Nelson and Shearer, "2, 4-D and Mycoleptodiscus terrestris for control of Eurasian watermilfoil," Journal of Aquatic Plant Management, 43: 29-34, 2005.
Nemeth et al., "Exogenous salicylic acid increases polyamine content but may decrease drought tolerance in maize," Plant Science, 2002, 162:569-574.
Notice for Mecoprop-P TGAC, Commonwealth of Australia Gazette No. NRA 3, 2 pages, Mar. 6, 2001.
Oregon State University, National Forage & Grasslands Cirriculumn, "Discuss the basics of grass growth," forages.oregonstate.edu [online] <URL: http://forages.oregonstate.edu/nfgc/eo/onlineforagecurriculum/instructormaterials/availabletopics/management/growth> copyright 2008, 6 pages.
Ostmeyer, "The Color Green," Golf Course Management, pp. 40, 44, Aug. 1994.
Palla et al., "Correlation of dispersion stability with surfactant concentration and abrasive particle size for chemical mechanical polishing (cmp) slurries," Journal of dispersion science and technology, 21(5):491-509, 2000.
Pamphlet for Daconil 2787 Flowable Fungicide, Syngenta Crop Protection Canada, Inc., 9 pages, May 2004.
Pamphlet for Daconil Ultrex Fungicide, Syngenta Crop Protection Canada, Inc., 9 pages, May 2004.
Patton and Latin, "Turfgrass Disease Profiles: Rhizoctonia Large Patch," Purdue University, Retrieved from the Internet: < URL: https://www.extension.purdue.edu/extmedia/BP/BP-117-W.pdf> Feb. 2005, 3 pages.
Pavlista, "Paraffin enhances yield and quality of the potato cultivar Atlantic," J. Prod. Agric., 8(1):40- 42, 1995.
PCT International Preliminary Report on Patentability in International Application No. PCT/CA2014/051169, dated Jun. 7, 2016, 5 pages.
PCT International Preliminary Report on Patentability in International Application No. PCT/CA2020/050083, dated Apr. 21, 2021, 5 pages.
PCT International Preliminary Report on Patentability in International Appln. No. PCT/CA2019/050554, dated Nov. 12, 2020, 7 pages.

(56) References Cited

OTHER PUBLICATIONS

PCT International Preliminary Report on Patentability in PCT Appln. No. PCT/CA2018/050997, dated Feb. 18, 2020, 7 pages.
PCT International Search Report and Written Opinion in International Application No. PCT/CA2014/051169, dated Feb. 17, 2015, 3 pages.
PCT International Search Report and Written Opinion in International Application No. PCT/CA2020/050083, dated Apr. 22, 2020, 10 pages.
PCT International Search Report and Written Opinion in International Appln. No. PCT/CA2019/050554, dated Aug. 1, 2019, 8 pages.
PCT International Search Report and Written Opinion in PCT Appln. No. PCT/CA2018/050997, dated Nov. 14, 2018, 12 pages.
Perry, "Ground Covers: Specifications and Costs," California Turfgrass Culture, 21(3):21-22, 1971.
Perry, "Silicone Surface-Active Agents," Dow Corning Corporation, 2005. Retrieved from the Internet: < URL: http://www.dowcorning.com/content/publishedlit/26/1365.pdf>, 12 pages.
Pest Control for Professional Turfgrass Managers 2011, North Carolina State University, retrieved on Sep. 15, 2011. Retrieved from the Internet: < URL: http://www.turffiles.ncsu.edu/PDFFiles/004176/AG408PestControl_Prof- essionals.pdf>, 58 pages.
Pesticide Product Label System (PPLS), Search Results for PureSpray Oil 10E, Approval dates Apr. 21, 2000, Jul. 23, 2002, Sep. 24, 2003, Mar. 5, 2004. EPA Office of Pesticide Programs. Retrieved from the Internet: <http://oaspub.epa.gov/pestlabl/ppls.srchreslt?CompNum=69526&ProdNum=5>, 26 pages.
Phung et al., "Porphyrin biosynthesis control under water stress: sustained porphyrin status correlates with drought tolerance in transgenic rice," Plant physiology, Dec. 1, 2011, 157(4): 1746-1764.
Platte Chemical Co., "Product Information Bulletin: Salvo: A premium broadleaf herbicide for use in corn, small grains, grass pastures, reangeland and other crop and noncrop areas," 6 p. 2001.
Product Bulletin for Caltex, Caltex Australia, retrieved Aug. 2, 2006. Retrieved from the Internet: <URL: http://www.caltex.com.au/products_oil_detail_print.asp?id=229>, 2 pages.
Product Information Sheet for Sylgard 309 Silicone Surfactant, Dow Corning Corporation, 4 pages, May 2004.
Propiconazole Pesticide Information Profile, Extension Toxicology Network, Oct. 1997. Retrieved from the Internet: < URL: http://pmep.cce.cornell.edu/profiles/extoxnet/metiram- propoxur/propiconazole-ext.html>, 6 pages.
PureSpray Spray Oil 10E, Delaware Department of Agriculture Pesticide Database Searches, 2 pages, retrieved Apr. 7, 2005.
Puterka, "Fungal pathogens for arthropod pest control in orchard systems: mycoinsecticidal approach for pear psylla control," BioControl, 44(2): 183-209, 1999.
Quantification of Phosphorus in Water Based Green Pigments, 1 p. 2009.
Quicksheet for SALVO Herbicide, UAP Canada, 4 p. 2006.
Rieke, "Thatchremoval," California Turfgrass Culture, 21(3): 19-20, 1971.
Ross et al., "The Effect of the Plant Growth Regulator Primo on Winter Hardiness Levels, " Prairie Turfgrass Research Centre, retrieved on Aug. 25, 2011. Retrieved from the Internet: < URL: http://www.oldscollege.ca/ptrc/2004_ar/Primohardiness02-05.htm>, 4 pages.
Samoucha et al., "Synergism in fungicide mixtures against Pseudoperonospora cubensis," Phytoparasitica, 16(4):337-342, 1988.
Sarkissian IV et al., "Regulation of mitochondrial activity by indoleacetic acid," Biochim Biophys Acta., 128(3):413-418, Dec. 14, 1966.
Schott et al., "Effects of adjuvants on herbicidal action. III. Effects of petroleum and rapeseed oils on diclofop-methyl action on ryegrass," Agronomie, 11(1):27-34, 1991.
Schutte et al., "Application of Azoxystrobin for Control of Benomyl-Resistant Guignardia citricarpa on 'Valencia' Oranges in South Africa," Plant Dis., 87(7): 784-788, Jul. 2003.

Scotts Canada Home: Killex Concentrate, Retrieved Aug. 2, 2006. Retrieved from the Internet: < URL: http://scottscanada.calindex.cfmleventlProductGuide.product/documentld/30B255B82B>, 2 pages.
Shaposhnikov et al., "Carboxy-substituted phthalocyanine metal complexes," Russian journal of general chemistry, 75(9): 1480-1488, 2005.
Shearman et al., "Colorant effects on dormant buffalograss turf performance, " HortTechnology, 15(2), 244-246, 2005.
Short and Castner, "Turfgrass Insects Sheet 1," University of Florida, Nov. 1992, reviewed Jun. 2005. Retrieved from the Internet: < URL: http://edis.ifas.ufl.edu/in025>, 2 pages.
Short and Castner, "Turfgrass Insects Sheet 2," University of Florida, Nov. 1992, reviewed May 2003. Retrieved from the Internet: < URL: http://edis.ifas.ufl.edu/in026>, 2 pages.
Smitley and Davis, "Black Cutworms," Michigan State University Turfgrass Science, archived on Feb. 12, 2010. Retrieved from the Internet: <URL: http://www.turf.msu.edu/black-cutworms>, 2 pages.
Soomary et al., "Evaluation of Fungicides for Control of the Leaf Spot Disease Caused by Mycosphaerella eumusae on Banana in Mauritius," Food and Agricultural Research Council, Proceedings Fourth Annual Meeting of Agricultural Scientists, pp. 61-65, Feb. 2001.
Specimen Label for AGRI-DEX, Helena Chemical Company, 2 p. 2005.
Specimen Label for Banner MAXX, Syngenta Crop Protection, Inc., 31 pages, May 2004.
Specimen Label for Blendex Vhc, Helena Chemical Company, 2 pages, May 2006.
Specimen Label for Chipco Signature, Bayer CropScience Pty Ltd, 2 pages, May 2004.
Specimen Label for Civitas, Petro-Canada Lubricants, Inc., 9 pages, May 2004.
Specimen Label for Cleary 3336 Plus, Cleary Chemical Corporation, 4 pages, May 2004.
Specimen Label for Fore 80WP Rainshield, Dow AgroSciences, 7 pages. Revised Jan. 8, 2007.
Specimen Label for Grass Greenzit: Permanent Green Pigment for Grass, 2 p. 1998.
Specimen Label for Harmonizer, Petro-Canada Lubricants, Inc., 1 page, May 2004.
Specimen Label for Killex, Scotts, Canada Ltd., 6 pages, Jul. 23, 2001.
Specimen Label for Peptoil, Drexel Chemical Company, 2 pages, May 2004.
Specimen Label for Regreen, Precision Laboratories, Inc. 2 pages, Dec. 10, 2007.
Specimen Label for Rovral Green GT, Bayer CropScienc Inc., 2 pages, Mar. 19, 2009.
Specimen Label for Sil-Fact, Drexel Chemical Company, 1 page, May 2004.
Specimen Label for Sil-MES 100, Drexel Chemical Company, 1 pages, May 2004.
Specimen Label for Surf-Ac 820, Drexel Chemical Company, 1 page, May 2004.
Specimen Label for Trimec Classic, PBI/Gordon Corporation, 2 p. 1973.
Specimen Label for Trimec Southern, PBt/Gordon Corporation, 2 p. 1987.
Srivastava, "Auxins, Plant growth and development: Hormones and environment", Chapter 6, pp. 155-169, Retrieved from https://ebookcentral.proquest.corn, 2002.
STN Database accession No. 1939:39478, 1 page, Dec. 16, 2001.
Sunspray 11N, Safety data sheet 2019, 1 page.
Szulbinski et al., "Electrochemical and photocatalytic properties of water-soluble tin (IV) meso- tetraanilinporphyrin," Journal of electroanalytical chemistry and interfacial electrochemistry, Jul. 10, 1987, 226(1-2):157-170.
Szulbinski et al., "Photoinduced reduction of water by tin (IV) and ruthenium (II) porphyrins," Inorganica chimica acta, Aug. 15, 1986, 118(2):91-97.
Technical Data Sheet for Lambent MFF 159-100, Lambent Technologies Corp., 1 page, May 2004.

(56) References Cited

OTHER PUBLICATIONS

Technical Data Sheet for Lambent MFF-199 Sw, Lambent Technologies Corp., 1 page, May 2004.
Technical Data Sheet for Silsurf A008-UP, Siltech Corporation, 1 page, May 2004.
Technical Information for Lutensol AT types, Basf Se, 10 pages, May 2004.
Technical Sheet for Green Lawnger, Becker Underwood, Inc. 1 page, Nov. 2010.
Templeman, "The effect of some plant growth-substances on dry-matter production in plants," Empire J Exp Agric., 7(1): 76-88, Jan. 1, 1939.
The Seed Site, "Monocots and Dicots," captured Feb. 24, 2010. Retrieved from the Internet: <URL: http://web.archive.org/web/20100224074428/http://theseedsite.co.uk/monocot.html >, 2 pages.
Trathnigg et al., "Molecular characterization of ethoxylates by complementary chromatographic techniques. Evaluation of efficiency and reliability, " Tenside Surf. Det., 40(3), 148-154, 2003.
Tu et al., "Weed control methods handbook: tools and techniques for use in natural areas," The Nature Conservancy, Wildland Invasive Species TEAM, version Apr. 2001, 219 pages.
Turfgrass Pest Control, West Virginia University, retrieved on Aug. 22, 2011. Retrieved from the Internet: < URL: http://www.wvu.edu/.about.exten/infores/pubs/pest/pcertil9.pdf>, 12 pages.
Uchoa et al., "Relationship between structure and photoactivity of porphyrins derived from protoporphyrin IX," Journal of Porphyrins and Phthalocyanines, Sep. 2010, 14(09):832-845.
University of Arkansas, "Turf Tip - MSMA, Fungicide synergism, Buffalograss, Pythium." Retrieved from the Internet: < URL: http://turf.uark.edu/turfhelp/archives/030509.html> Mar. 5, 2009, 3 pages.
Unruh and Brecke, "Plant Growth Retardants for Fine Turf and Roadsides/Utilities," University of Florida, Apr. 1999, reviewed Sep. 2006, retrieved on Aug. 24, 2011. Retrieved from the Internet: <URL: http://edis.ifas.ufl.edu/pdffiles/WG/WG06400.pdf>, 5 pages.
Untiedt et al., "Effects of fungicide and insecticide mixtures on apple tree canopy photosynthesis, dark respiration and carbon economy," Crop Protection, 2004, 23:1001-1006.
Vallad and Goodman et al., "Systemic Acquired Resistance and Induced Systemic Resistance in Conventional Agriculture," Crop Science, 44(6): 1920-1934, 2004.
Van Dam and Kurtz, "A Turfgrass Colorant Study," California Turfgrass Culture, 21(3):17-19, Summer 1971.
Van Haeringen et al., "The Development of Solid Spectral Filters for the Regulation of Plant Growth," Photochemistry and Photobiology, 67(4): 407-413, Apr. 1998.
Vanbibber, "Putting the Nos. to PGRs," Grounds Maintenance, 2008. Retrieved from the Internet: < URL: http://grounds-mag.com/chemicals/ grounds_maintenance_putting_numbers_pgrs/>, 6 pages.
Vandresen et al., "In vitro photodynamic inactivation of conidia of the phytopathogenic fungus Colletotrichum graminicola with cationic porphyrins," Photochemical & Photobiological Sciences, 2016, 15(5):673-681.
Vann et al., "Rhizoctonia Large Patch Disease of Zoysiagrass and Bermudagrass," University of Arkansas Division of Agriculture, <https://www.uaex.edu/publications/PDF/FSA-7527.pdf> Mar. 1, 2007, 2 pages.

Vincelli, "Chemical Control of Turfgrass Diseases 2011," University of Kentucky College of Agriculture, <URL: http://pest.ca.uky.edu/PSEP/Manuals/ppal.pdf>, 24 pages.
Vol'pin et al., "Redox and fungicidal properties of phthalocyanine metal complexes as related to active oxygen," Journal of Inorganic Biochemistry, 81(4): 285-292, 2000.
Walsh et al., "Biology and management of dollar spot (Sclerotinia homoeocarpa); an important disease of turfgrass," HortScience., 34(1): 13-21, 1999.
Wang, "Pesticide Pharmaceutics," China Agriculture Press, pp. 142-143, Aug. 2009, (English translation), 5 pages.
Wicks, "Control of grapevine powdery mildew with mineral oil: an assessment of oil concentration and spray volume," Australian Journal of Grape and Wine Research, 5:61-65, 1999.
Wikipedia, "2,4-Dichlorophenoxyacetic acid," retrieved on Aug. 29, 2006. Retrieved from the Internet: <URL: http://en.wikipedia.orglwikii2%2C4-D>, 3 pages.
Womack et al., "A vegetable oil-based invert emulsion for mycoherbicide delivery," Biological Control, 6(1), 23-28, 1996.
Xia et al., "Pesticides-induced depression of photosynthesis was alleviated by 24- epibrassinolide pretreatment in Cucumis sativus L," Pesticide Biochemistry and Physiology, 2006, 86:42-48.
Yang et al., "Infection of leafy spurge by Alternaria alternata and A. angustiovoidea in the absence of dew," Phytopathology, 83(9): 953-958, 1993.
Yang et al., "Physiological and metabolic effects of 5-aminolevulinic acid for mitigating salinity stress in creeping bentgrass," PLOS One, Dec. 31, 2014, 9(12):e116283, 25 pages.
Yang et al., "Silica-hemin composite nanoparticles as new biocatalyst to highly sensitive determination of glucose in human serum," Analytical sciences, 2004, 20(9):1265-1270.
Youngner et al., "Colorants for Dormant Bermuda and Other Subtropical Grasses," Southern California Turfgrass Culture, 8(1):7-8, 1958.
Youngner, "Gibberellic acid on Zoysia grasses," Southern California Turfgrass Culture, 8:5-6, 1958.
Youngner, "Kikuyugrass, Pennisetum Clandestinum, and Its Control," Southern California Turfgrass Culture, 8(1):1-4, Jan. 1958.
Zhang et al., "Disinfection Effectiveness of Photodynamic Therapy Combined with EDTA on Infected Root Cancals in Vitro," Journal of Oral Science Research, Apr. 2014, 30(10): 317-320, English Abstract.
Zhang et al., "Role of 5-aminolevulinic acid in the salinity stress response of the seeds and seedlings of the medicinal plant Cassia obtusifolia L," Botanical studies, Dec. 2013, 54(1):1-13.
Zhengdong, "Application of SK EnSpray Oil," Pesticide Science and Administration, 28(10):25-29, Dec. 31, 2007.
Chembk.com [online], "C.I. Pigment Green 7," Mar. 28, 2022, retrieved on Aug. 4, 2022, retrieved from URL<https://www.chembk.com/en/chem/C.I.%20Pigment%20Green%207>, 7 pages.
International Search Report and Written Opinion in International Appln. No. PCT/CA2020/050219, dated Nov. 5, 2020, 8 pages.
Mojarrad et al., "A novel porphyrinic photosensitizer based on the molecular complex of meso-tetraphenylporphyrin with 2, 3-dichloro-5, 6-dicyano-1, 4-benzoquinone: higher photocatalytic activity, photooxidative stability and solubility in non- chlorinated solvents, " RSC advances, 2016, 6(103): 100931-100938.

* cited by examiner

PROTOPORPHYRIN IX DERIVATIVES AND USE THEREOF TO IMPROVE THE HEALTH OF PLANTS

CROSS REFERENCE TO RELATED APPLICATIONS

This application is a National Stage application under 35 U.S.C. § 371 of International Application No. PCT/CA2020/050197 filed on Feb. 14, 2020, which claims priority to United-States provisional application No. 62/806,084 filed on Feb. 15, 2019, the content of each of which is incorporated herein by reference in its entirety for all purposes.

FIELD

The technical field generally relates to photosensitizer tetrapyrrole compounds and their use for promoting the health of plants. More particularly, the technical field relates to modified protoporphyrin IX (PP IX) compounds and use thereof for photodynamic inhibition of microbial pathogens, such as fungal or bacterial pathogens, in plants. The modified PP IX compounds can also be used for increasing abiotic stress resistance or tolerance in plants and/or as insecticides to protect plants from plant pests.

BACKGROUND

Photodynamic inhibition of microbial pathogens involves exposing a photosensitive agent to light in order to generate reactive oxygen species (ROS), such as singlet oxygen, which can have detrimental effects on the microbial pathogens. Existing photodynamic inhibition techniques and applications have various shortcomings.

SUMMARY

In one aspect of the present description, there is provided a compound of Formula I:

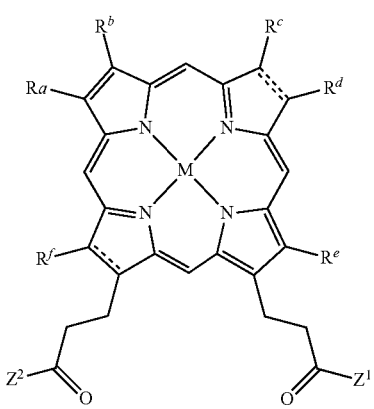

Formula I or an agriculturally acceptable salt thereof, for use in promoting the health of a plant,
wherein:

$Z^1$ and $Z^2$ are each independently $OR^1$ or $NR^2R^3$;

each $R^1$, $R^2$ and $R^3$ is independently H, alkyl, substituted alkyl, aryl, substituted aryl, alkenyl, substituted alkenyl, alkynyl, or substituted alkynyl, wherein:

if $Z^1$ and $Z^2$ are both $OR^1$ then at least one $R^1$ is not H,
if $Z^1$ and $Z^2$ are both $NR^2R^3$ then at least one $R^3$ is not H, and
if one of $Z^1$ and $Z^2$ is $OR^1$ and the other one of $Z^1$ and $Z^2$ is $NR^2R^3$, then at least one of $R^1$ and $R^3$ is not H;

each $R^a$, $R^b$, $R^c$, $R^d$, $R^e$ and $R^f$ is, independently, H, alkyl, substituted alkyl, aryl, substituted aryl, alkenyl, substituted alkenyl, alkynyl or substituted alkynyl;

⁃⁃⁃⁃⁃⁃ is a single bond or a double bond;
====== is a single bond or a double bond; and
M is 2H or a metal species, wherein the substituted alkyl, substituted aryl, substituted alkenyl and substituted alkynyl groups are, independently, substituted with one or more —X, —$R^B$, —$O^-$, =O, —$OR^B$, —$SR^B$, —$S^-$, —$NR^B{}_2$, $Si(R^C)_3$, —$N^+R^B{}_3$, —$NR^B$-(Alk)—$NR^B{}_2$, —$NR^B$-(Alk)-$N^+R^B{}_3$, —$NR^B$-(Alk)-$OR^B$, —$NR^B$-(Alk)-OP(=O)($OR^B$)($O^-$), —$NR^B$-(Alk)-OP(=O)($OR^B$)$_2$, —$NR^B$-(Alk)-$Si(R^C)_3$, —$NR^B$-(Alk)-$SR^B$, —O-(Alk)-$NR^B{}_2$, —O-(Alk)-$N^+R^B{}_3$, —O-(Alk)-$OR^B$, —O-(Alk)-OP(=O)($OR^B$)($O^-$), —O-(Alk)-OP(=O)($OR^B$)$_2$, —O-(Alk)-$Si(R^C)_3$, —O-(Alk)-$SR^B$, =$NR^B$, —$CX_3$, —CN, —OCN, —SCN, —N=C=O, —NCS, —NO, —$NO_2$, =$N_2$, —$N_3$, —NHC(=O)$R^B$, —OC(=O)$R^B$, —NHC(=O)$NR^B{}_2$, —S(=O)$_2$—, —S(=O)$_2$OH, —S(=O)$_2R^B$, —OS(=O)$_2OR^B$, —S(=O)$_2NR^B{}_2$, —S(=O)$R^B$, —OP(=O)($OR^B$)($O^-$), —OP(=O)($OR^B$)$_2$, —P(=O)($OR^B$)$_2$, —P(=O)($O^-$)$_2$, —P(=O)(OH)$_2$, —P(O)($OR^B$)($O^-$), —C(=O)$R^B$, —C(=O)X, —C(S)$R^B$, —C(O)$OR^B$, —C(O)—, —C(S)$OR^B$, —C(O)$SR^B$, —C(S)$SR^B$, —C(O)$NR^B{}_2$, —C(S)$NR^B{}_2$ or —C(=$NR^B$)$NR^B{}_2$;

each X is independently a halogen: F, Cl, Br or I;

each $R^B$ is independently H, alkyl, aryl, arylalkyl, a heterocycle, an alkyloxy group such as poly(ethyleneoxy), PEG or poly(methyleneoxy), a capped poly(ethyleneoxy), capped PEG or capped polymethyleneoxy, or a protecting group;

the capped poly(ethyleneoxy), capped PEG and capped poly(methyleneoxy) groups being each independently capped with alkyl, aryl, arylalkyl, alkenyl, alkynyl, CO(alkyl), CO(aryl), CO(arylalkyl), CO(alkenyl) or CO(alkynyl);

each $R^C$ is independently alkyl, aryl, arylalkyl, O(alkyl), O(aryl), O(arylalkyl), or O(tri-substituted silyl);

each tri-substituted silyl is independently substituted with three functional groups selected from alkyl, alkenyl, alkynyl, aryl and arylalkyl; and each Alk is independently alkylene, alkenylene, or alkynylene.

In another aspect of the present description, there is provided a compound of Formula I:

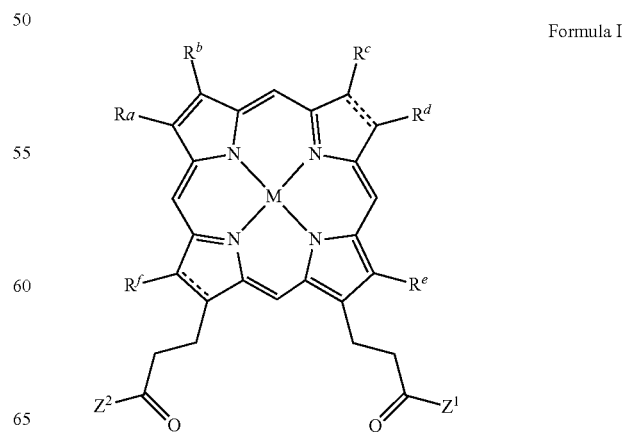

Formula I or an agriculturally acceptable salt thereof, for use in promoting the health of a plant,
wherein:
one of $Z^1$ and $Z^2$ is $OR^1$; and
the other one of $Z^1$ and $Z^2$ is $NR^2R^3$, $NR^2$—$(CH_2)_n$—$NR^4R^5$, $NR^2$—$(CH_2)_n$—$N^+R^4R^5R^6$ $Y^-$, $NR^2$—$(CH_2)_n$—$O(PO_3H)^-$ $W^+$, $NR^2$—$(CH_2)_n$—$Si(R^7)_3$, $NR^2$—$(CH_2)_n$—$SR^8$, $NR^2$—$(CH_2)_n$—$NR^4$—$(CH_2)_p$—$NR^9R^{10}$, $NR^2$—$(CH_2)_n$—$NR^4$—$(CH_2)_p$—$N^+R^9R^{10}R^{11}$ $Y^-$, $NR^2$—$(CH_2)_n$—$NR^4$—$(CH_2)_p$—$O(PO_3H)^-$ $W^+$, $NR^2$—$(CH_2)_n$—$NR^4$—$(CH_2)_p$—$Si(R^7)_3$, $NR^2$—$(CH_2)_n$—$NR^4$—$(CH_2)_p$—$SR^8$, $O(CH_2)_n$—$NR^4R^5$, $O(CH_2)_n$—$N^+R^4R^5R^6$ $Y^-$, $O(CH_2)_n$—$O(PO_3H)^-$ $W^+$, $O(CH_2)_n$—$Si(R^7)_3$, $O(CH_2)_n$—$SR^8$, $O(CH_2)_n$—$NR^4$—$(CH_2)_p$—$NR^9R^{10}$, $O(CH_2)_n$—$NR^4$—$(CH_2)_p$—$N^+R^9R^{10}R^{11}$ $Y^-$, $O(CH_2)_n$—$NR^4$—$(CH_2)_p$—$O(PO_3H)^-$ $W^+$ or $O(CH_2)_n$—$NR^4$—$(CH_2)_p$—$Si(R^7)_3$;
or
$Z^1$ is $NR^2R^3$, $NR^2$—$(CH_2)_n$—$NR^4R^5$, $NR^2$—$(CH_2)_n$—$N^+R^4R^5R^6$ $Y^-$, $NR^2$—$(CH_2)_n$—$O(PO_3H)^-$ $W^+$, $NR^2$—$(CH_2)_n$—$Si(R^7)_3$, $NR^2$—$(CH_2)_n$—$SR^8$, $NR^2$—$(CH_2)_n$—$NR^4$—$(CH_2)_p$—$NR^9R^{10}$, $NR^2$—$(CH_2)_n$—$NR^4$—$(CH_2)_p$—$N^+R^9R^{10}R^{11}$ $Y^-$, $NR^2$—$(CH_2)_n$—$NR^4$—$(CH_2)_p$—$O(PO_3H)^-$ $W^+$, $NR^2$—$(CH_2)_n$—$NR^4$—$(CH_2)_p$—$Si(R^7)_3$, $NR^2$—$(CH_2)_n$—$NR^4$—$(CH_2)_p$—$SR^8$, $O(CH_2)_n$—$NR^4R^5$, $O(CH_2)_n$—$N^+R^4R^5R^6$ $Y^-$, $O(CH_2)_n$—$O(PO_3H)^-$ $W^+$, $O(CH_2)_n$—$Si(R^7)_3$, $O(CH_2)_n$—$SR^8$, $O(CH_2)_n$—$NR^4$—$(CH_2)_p$—$NR^9R^{10}$, $O(CH_2)_n$—$NR^4$—$(CH_2)_p$—$N^+R^9R^{10}R^{11}$ $Y^-$, $O(CH_2)_n$—$NR^4$—$(CH_2)_p$—$O(PO_3H)^-$ $W^+$ or $O(CH_2)_n$—$NR^4$—$(CH_2)_p$—$Si(R^7)_3$; and
$Z^2$=$Z^1$;
each $R^1$ and $R^2$ is, independently, H, alkyl, substituted alkyl, aryl, substituted aryl, alkenyl, substituted alkenyl, alkynyl or substituted alkynyl;
$R^3$ is alkyl, substituted alkyl, aryl, substituted aryl, alkenyl, substituted alkenyl, alkynyl or substituted alkynyl;
each $R^4$, $R^6$, $R^8$, $R^9$, $R^{10}$ and $R^{11}$ is, independently, H, alkyl, substituted alkyl, aryl, substituted aryl, alkenyl, substituted alkenyl, alkynyl, substituted alkynyl or —$(CH_2)_q$—$(CH_2CH_2O)_m$—$R^{13}$;
$R^5$ is alkyl, substituted alkyl, aryl, substituted aryl, alkenyl, substituted alkenyl, alkynyl, substituted alkynyl or —$(CH_2)_q$—$(CH_2CH_2O)_m$—$R^{13}$;
$R^7$ is alkyl, O(alkyl) or O(tri-substituted silyl);
$R^{13}$ is H, alkyl, substituted alkyl, aryl, substituted aryl, alkenyl, substituted alkenyl, alkynyl, substituted alkynyl, CO(alkyl), CO(substituted alkyl), CO(alkenyl), CO(substituted alkenyl), CO(alkynyl) or CO(substituted alkynyl);
$W^+$ is an agriculturally acceptable cation;
$Y^-$ is an agriculturally acceptable anion;
n is an integer selected from 1 to 16;
p is an integer selected from 1 to 16;
m is an integer selected from 1 to 100;
q is an integer selected from 0 to 16;
each $R^a$, $R^b$, $R^c$, $R^d$, $R^e$ and $R^f$ is, independently, H, alkyl, substituted alkyl, aryl, substituted aryl, alkenyl, substituted alkenyl, alkynyl or substituted alkynyl;
====== is a single bond or a double bond;
====== is a single bond or a double bond; and
M is 2H or a metal species,
wherein each substituted alkyl, substituted aryl, substituted alkenyl and substituted alkynyl groups are, independently, substituted with one or more OH, F, Cl, Br, I, CN and $N_3$.
In yet another aspect of the present description, there is provided a compound of Formula I-B1:

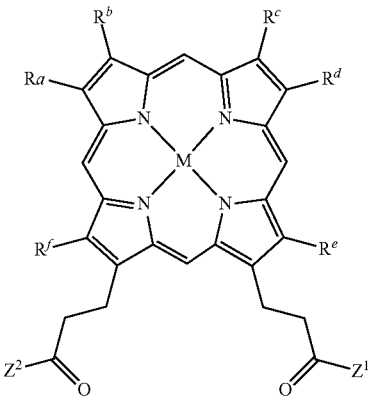

Formula I-B1 or an agriculturally acceptable salt thereof, for use in promoting the health of a plant, wherein:
one of $Z^1$ and $Z^2$ is $NR^2R^3$; and
the other one of $Z^1$ and $Z^2$ is $OR^1$;
or
$Z^1$=$NR^2R^3$; and
$Z^2$=$Z^1$;
each $R^1$ and $R^2$ is, independently, H, alkyl or substituted alkyl;
$R^3$ is alkyl or substituted alkyl;
each $R^a$, $R^b$, $R^c$, $R^d$, $R^e$ and $R^f$ is, independently, H, alkyl, substituted alkyl, alkenyl, substituted alkenyl, alkynyl or substituted alkynyl; and
M is 2H or a metal species,
wherein the substituted alkyl, substituted alkenyl and substituted alkynyl groups are, independently, substituted with one or more OH, F, Cl, Br, I, CN and $N_3$.
In yet another aspect of the present description, there is provided a compound of Formula I-B1:

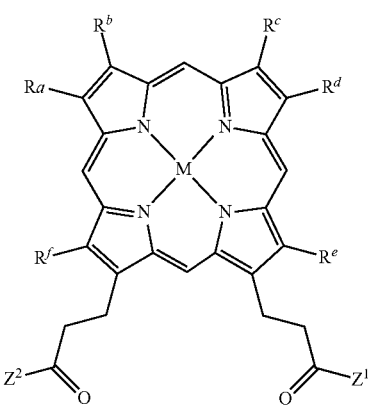

Formula I-B1 or an agriculturally acceptable salt thereof, for use in promoting the health of a plant, wherein:
one of $Z^1$ and $Z^2$ is $NR^2$—$(CH_2)_n$—$NR^4R^5$ or O—$(CH_2)_n$—$NR^4R^5$; and the other one of $Z^1$ and $Z^2$ is $OR^1$;
or
$Z^1$=$NR^2$—$(CH_2)_n$—$NR^4R^5$ or O—$(CH_2)_n$—$NR^4R^5$; and $Z^2$=$Z^1$;
$R^5$ is alkyl, substituted alkyl or —$(CH_2)_p$—$NR^9R^{10}$;
each $R^1$, $R^2$, $R^4$, $R^9$ and $R^{10}$ is, independently, H, alkyl or substituted alkyl;

n is an integer selected from 1 to 16;

p is an integer selected from 1 to 16;

each $R^a$, $R^b$, $R^c$, $R^d$, $R^e$ and $R^f$ is, independently, H, alkyl, substituted alkyl, alkenyl, substituted alkenyl, alkynyl or substituted alkynyl; and M is 2H or a metal species, wherein the substituted alkyl, substituted alkenyl and substituted alkynyl groups are, independently, substituted with one or more OH, F, Cl, Br, I, CN and $N_3$.

In yet another aspect of the present description, there is provided a compound of Formula I-B1:

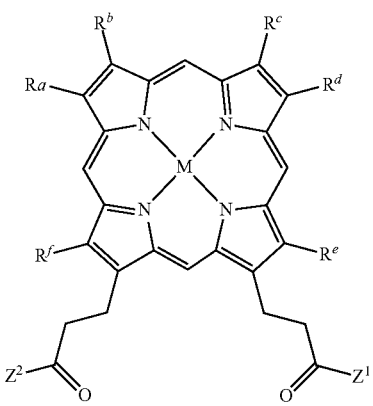

Formula I-B1 or an agriculturally acceptable salt thereof, for use in promoting the health of a plant, wherein:

one of $Z^1$ and $Z^2$ is $NR^2$—$(CH_2)_n$—$Si(R^7)_3$, O—$(CH_2)_n$—$Si(R^7)_3$, $NR^2$—$(CH_2)_n$—$SR^8$ or O—$(CH_2)_n$—$SR^8$; and the other one of $Z^1$ and $Z^2$ is $OR^1$;

or $Z^1$=$NR^2$—$(CH_2)_n$—$Si(R^7)_3$, O—$(CH_2)_n$—$Si(R^7)_3$, $NR^2$—$(CH_2)_n$—$SR^8$ or O—$(CH_2)_n$—$SR^8$; and $Z^2$=$Z^1$;

each $R^1$ and $R^2$ is, independently, H, alkyl or substituted alkyl;

$R^7$ is alkyl, O(alkyl) or O(trisubstituted silyl);

$R^8$ is H, alkyl, substituted alkyl or —$(CH_2)_q$—$(CH_2CH_2O)_m$—$R^{13}$;

$R^{13}$ is H, alkyl, substituted alkyl, alkenyl, substituted alkenyl, alkynyl, substituted alkynyl, CO(alkyl), CO(substituted alkyl), CO(alkenyl), CO(substituted alkenyl), CO(alkynyl) or CO(substituted alkynyl);

n is an integer selected from 1 to 16;

m is an integer selected from 1 to 100;

q is an integer selected from 0 to 16;

each $R^a$, $R^b$, $R^c$, $R^d$, $R^e$ and $R^f$ is, independently, H, alkyl, substituted alkyl, alkenyl, substituted alkenyl, alkynyl or substituted alkynyl; and M is 2H or a metal species, wherein the substituted alkyl, substituted alkenyl and substituted alkynyl groups are, independently, substituted with one or more OH, F, Cl, Br, I, CN and $N_3$.

In yet another aspect of the present description, there is provided a compound of Formula I-B1:

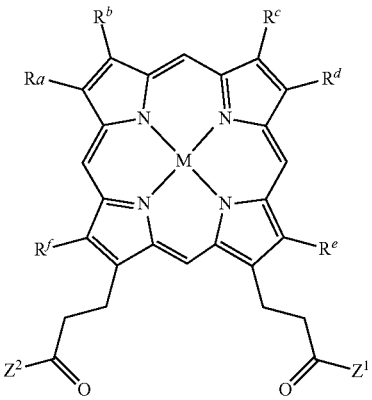

Formula I-B1 or an agriculturally acceptable salt thereof, for use in promoting the health of a plant, wherein:

one of $Z^1$ and $Z^2$ is $NR_2$—$(CH_2)_n$—OP=O(OH)$_2$ or O—$(CH_2)_n$—OP=O(OH)$_2$, $NR_2$—$(CH_2)_n$—OP=O(OH)O$^-$ W$^+$ or O—$(CH_2)_n$—OP=O(OH)O$^-$ W$^+$; and the other one of $Z^1$ and $Z^2$ is $OR^1$;

or $Z^1$ =$NR_2$—$(CH_2)_n$—OP=O(OH)$_2$ or O—$(CH_2)_n$—OP=O(OH)$_2$, $NR_2$—$(CH_2)_n$—OP=O(OH)O$^-$ W$^+$ or O—$(CH_2)_n$—OP=O(OH)O$^-$ W$^+$; and $Z^2$=$Z$;

each $R^1$ and $R^2$ is, independently, H, alkyl or substituted alkyl;

n is an integer selected from 1 to 16;

W$^+$ is an agriculturally acceptable cation;

each $R^a$, $R^b$, $R^c$, $R^d$, $R^e$ and $R^f$ is, independently, H, alkyl, substituted alkyl, alkenyl, substituted alkenyl, alkynyl or substituted alkynyl; and M is 2H or a metal species, wherein the substituted alkyl, substituted alkenyl and substituted alkynyl groups are, independently, substituted with one or more OH, F, Cl, Br, I, CN and $N_3$.

In yet another aspect of the present description, there is provided a compound of Formula I-B1:

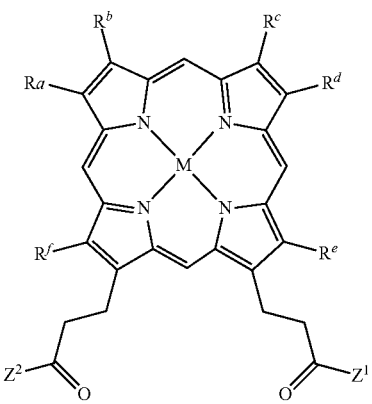

Formula I-B1 or an agriculturally acceptable salt thereof, for use in promoting the health of a plant, wherein:

one of $Z^1$ and $Z^2$ is $NR^2$—$(CH_2)_n$—$NR^4R^5R^{6+}$ Y$^-$ or O—$(CH_2)_n$—$NR^4R^5R^{6+}$ Y$^-$; and the other one of $Z^1$ and $Z^2$ is $OR^1$;

or $Z^1$=NR$^2$—(CH$_2$)$_n$—NR$^4$R$^5$R$^{6+}$ Y$^-$ or O—(CH$_2$)$_n$—NR$^4$R$^5$R$^{6+}$ Y$^-$; and $Z^2$=$Z^1$;

each R$^1$ and R$^2$ is, independently, H, alkyl or substituted alkyl;

each R$^4$, R$^5$ and R$^6$ is, independently, alkyl or substituted alkyl;

n is an integer selected from 1 to 16;

Y$^-$ is an agriculturally acceptable anion;

each R$^a$, R$^b$, R$^c$, R$^d$, R$^e$ and R$^f$ is, independently, H, alkyl, substituted alkyl, alkenyl, substituted alkenyl, alkynyl or substituted alkynyl; and M is 2H or a metal species, wherein the substituted alkyl, substituted alkenyl and substituted alkynyl groups are, independently, substituted with one or more OH, F, Cl, Br, I, CN and N$_3$.

In yet another aspect of the present description, there is provided a compound of Formula I-B1:

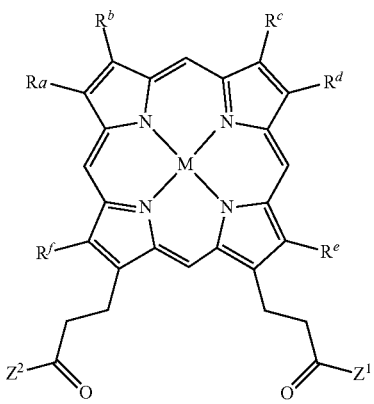

Formula I-B1 or an agriculturally acceptable salt thereof, for use in promoting the health of a plant, wherein:

one of Z$^1$ and Z$^2$ is NR$^2$—(CH$_2$CH$_2$O)$_m$—R$^{13}$ or O—(CH$_2$CH$_2$O)$_m$—R$^{13}$; and the other one of Z$^1$ and Z$^2$ is OR$^1$;

or $Z^1$=NR$^2$—(CH$_2$CH$_2$O)$_m$—R$^{13}$ or O—(CH$_2$CH$_2$O)$_m$—R$^{13}$; and $Z^2$=Z;

each R$^1$ and R$^2$ is, independently, H, alkyl or substituted alkyl;

R$^{13}$ is H, alkyl, substituted alkyl, alkenyl, substituted alkenyl, alkynyl, substituted alkynyl, CO(alkyl), CO(substituted alkyl), CO(alkenyl), CO(substituted alkenyl), CO(alkynyl) or CO(substituted alkynyl);

m is an integer selected from 1 to 100;

each R$^a$, R$^b$, R$^c$, R$^d$, R$^e$ and R$^f$ is, independently, H, alkyl, substituted alkyl, alkenyl, substituted alkenyl, alkynyl or substituted alkynyl; and M is 2H or a metal species, wherein the substituted alkyl, substituted alkenyl and substituted alkynyl groups are, independently, substituted with one or more OH, F, Cl, Br, I, CN and N$_3$.

In yet another aspect of the present description, there is provided a compound of Formula I-B1:

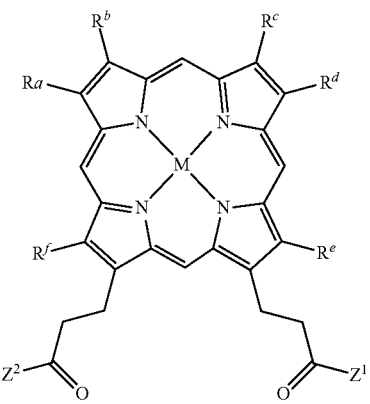

Formula I-B1 or an agriculturally acceptable salt thereof, for use in promoting the health of a plant, wherein:

one of Z$^1$ and Z$^2$ is a natural amino acid attached to the compound by its amino group bonded to the alpha carbon; and the other one of Z$^1$ and Z$^2$ is OR$^1$;

or

Z$^1$ is a natural amino acid attached to the compound by its amino group bonded to the alpha carbon; and $Z^2$=$Z^1$;

each R$^1$ and R$^2$ is, independently, H, alkyl or substituted alkyl;

each R$^a$, R$^b$, R$^c$, R$^d$, R$^e$ and R$^f$ is, independently, H, alkyl, substituted alkyl, alkenyl, substituted alkenyl, alkynyl or substituted alkynyl; and M is 2H or a metal species, wherein the substituted alkyl, substituted alkenyl and substituted alkynyl groups are, independently, substituted with one or more OH, F, Cl, Br, I, CN and N$_3$.

The present description also provides a composition for use in promoting the health of a plant, the composition comprising at least one compound as defined herein, or an agriculturally acceptable salt thereof, and a carrier fluid.

The present description also provides a method for promoting the health of a plant, comprising: applying to the plant a compound as defined herein or an agriculturally acceptable salt thereof, or a composition as defined herein; and exposing the plant to light.

Promoting the health of the plant can include at least one of preventing or inhibiting growth of a microbial pathogen of the plant (e.g., a fungus or a bacterial pathogen), increasing resistance of the plant to one or more abiotic stress, and controlling a pest of the plant (e.g., a noxious insect or corresponding larva).

DETAILED DESCRIPTION

Some microbial pathogens, such as Gram-negative bacteria and certain types of fungi have a cellular membrane that is difficult to penetrate. More specifically, these microbial pathogens sometimes have an impermeable outer cell membrane that contains endotoxins and can block small molecules such as antibiotics, dyes and detergents, thereby protecting the sensitive inner membrane and cell wall. It can therefore be challenging to use photodynamic therapy to inhibit growth of certain microbial pathogens in plants because the photosensitizer compounds tend to not achieve good penetration inside the cell wall. It can also be challenging to increase resistance of plants to damage caused by abiotic stresses.

In some scenarios, photodynamic inhibition of microbial pathogens that are present on plants can be achieved by applying a photosensitizer compound. The photosensitizer compound reacts to light by generating reactive oxygen species (ROS). In other scenarios, a photosensitizer compound can be used to increase resistance of plants to damage caused by one or more abiotic stress.

Some of the compounds of the present description are photosensitizer compounds that can be derived from the protoporphyrin IX (hereinafter "PP IX") scaffold. The compounds derived from PP IX can also be referred to as "modified PP IX". Some of the compounds of the present description are photosensitizer compounds that have a scaffold similar to that of PP IX, but that are not necessarily derived from PP IX. In some scenarios, these compounds can be used to improve the health of plants. That is, depending on the compound and/or mode of application, the compounds of the present description can be applied to plants to photodynamically inhibit microbial pathogens on plants, to increase resistance of plants to damage caused by one or more abiotic stress and/or to be used as insecticides.

Definitions

Unless stated otherwise, the following terms and phrases as used herein are intended to have the following meanings.

When trade names are used herein, it is intended to independently include the tradename product and the active ingredient(s) of the tradename product.

As used herein, the phrase "a compound of Formula I" means a compound of Formula I or an agriculturally acceptable salt thereof. With respect to isolatable intermediates, the phrase "a compound of Formula (number)" means a compound of that formula and salts thereof, and optionally agriculturally acceptable salts thereof.

The term "Alkyl", as used herein, means a hydrocarbon containing primary, secondary, tertiary or cyclic carbon atoms. For example, and without being limiting, an alkyl group can have 1 to 20 carbon atoms (i.e, $C_1$-$C_{20}$ alkyl), 1 to 8 carbon atoms (i.e., $C_1$-$C_8$ alkyl), 1 to 6 carbon atoms (i.e., $C_1$-$C_6$ alkyl) or 1 to 4 carbon atoms (i.e., $C_1$-$C_4$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

The term "Alkenyl", as used herein, means a hydrocarbon containing primary, secondary, tertiary or cyclic carbon atoms with at least one site of unsaturation, i.e. a carbon-carbon $sp^2$ double bond. For example, and without being limiting, an alkenyl group can have 2 to 20 carbon atoms (i.e., $C_2$-$C_{20}$ alkenyl), 2 to 8 carbon atoms (i.e., $C_2$-$C_8$ alkenyl), 2 to 6 carbon atoms (i.e., $C_2$-$C_6$ alkenyl) or 2 to 4 carbon atoms (i.e., $C_2$-$C_4$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

The term "Alkynyl", as used herein, means a hydrocarbon containing primary, secondary, tertiary or cyclic carbon atoms with at least one site of unsaturation, i.e. a carbon-carbon, sp triple bond. For example, and without being limiting, an alkynyl group can have 2 to 20 carbon atoms (i.e., $C_2$-$C_{20}$ alkynyl), 2 to 8 carbon atoms (i.e., $C_2$-$C_8$ alkynyl), 2 to 6 carbon atoms (i.e., $C_2$-$C_6$ alkynyl) or 2 to 4 carbon atoms (i.e., $C_2$-$C_4$ alkynyl). Examples of suitable alkynyl groups include, but are not limited to, acetylenic (—C≡CH) and propargyl (—$CH_2$C≡CH).

The term "Alkoxy", as used herein, is interchangeable with the term "O(Alkyl)", in which an "Alkyl" group as defined above is attached to the parent molecule via an oxygen atom. For example, and without being limiting, the alkyl portion of an O(Alkyl) group can have 1 to 20 carbon atoms (i.e, $C_1$-$C_{20}$ alkyl), 1 to 8 carbon atoms (i.e., $C_1$-$C_8$ alkyl), 1 to 6 carbon atoms (i.e., $C_1$-$C_6$ alkyl) or 1 to 4 carbon atoms (i.e., $C_1$-$C_4$ alkyl). Examples of suitable Alkoxy or O(Alkyl) groups include, but are not limited to, methoxy (—$OCH_3$ or —OMe), ethoxy (—$OCH_2CH_3$ or —OEt) and t-butoxy (—O—$C(CH_3)_3$ or —OtBu). Similarly, "O(alkenyl)", "O(alkynyl)" and the corresponding substituted groups will be understood by a person skilled in the art.

The term "Acyl", as used herein, is meant to encompass several functional moieties such as "C=O(Alkyl)", "C=O(Alkenyl)", "C=O(Alkynyl)" and their corresponding substituted groups, in which an "Alkyl", "Alkenyl" and "Alkynyl" groups are as defined above and attached to an O, N, S of a parent molecule via a C=O group. For example, and without being limiting, the alkyl portion of a C=O(Alkyl) group can have 1 to 20 carbon atoms (i.e, $C_1$-$C_{20}$ alkyl), 1 to 8 carbon atoms (i.e., $C_1$-$C_8$ alkyl), 1 to 6 carbon atoms (i.e., $C_1$-$C_6$ alkyl) or 1 to 4 carbon atoms (i.e., $C_1$-$C_4$ alkyl). Examples of suitable Acyl groups include, but are not limited to, formyl (i.e., a carboxyaldehyde group), acetyl, trifluoroacetyl, propionyl, and butanoyl. A person skilled in the art will understand that a corresponding definition applies for "C=O(Alkenyl)" and "C=O(Alkynyl)" moieties. In the present description, "C=O(Alkyl)", "C=O(Alkenyl)", "C=O(Alkynyl)" can also be written as "CO(Alkyl)", "CO(Alkenyl) and "CO(Alkynyl)", respectively.

The term "Alkylene", as used herein, means a saturated, branched or straight chain or cyclic hydrocarbon radical having two monovalent radical centers derived by the removal of two hydrogen atoms from the same or two different carbon atoms of a parent alkane. For example, and without being limiting, an alkylene group can have 1 to 20 carbon atoms, 1 to 10 carbon atoms, 1 to 6 carbon atoms or 1 to 4 carbon atoms. Typical alkylene radicals include, but are not limited to, methylene (—$CH_2$—), 1,1-ethyl (—CH($CH_3$)—), 1,2-ethyl (—$CH_2CH_2$—), 1,1-propyl (—CH($CH_2CH_3$)—), 1,2-propyl (—$CH_2$CH($CH_3$)—), 1,3-propyl (—$CH_2CH_2CH_2$—) and 1,4-butyl (—$CH_2CH_2CH_2CH_2$—).

The term "Alkenylene", as used herein, means an unsaturated, branched or straight chain or cyclic hydrocarbon radical having two monovalent radical centers derived by the removal of two hydrogen atoms from the same or two different carbon atoms of a parent alkene. For example, and without being limiting, and alkenylene group can have 1 to 20 carbon atoms, 1 to 10 carbon atoms, 1 to 6 carbon atoms or 1 to 4 carbon atoms. Typical alkenylene radicals include, but are not limited to, 1,2-ethylene (—CH=CH—).

The term "Alkynylene", as used herein, means an unsaturated, branched or straight chain or cyclic hydrocarbon radical having two monovalent radical centers derived by the removal of two hydrogen atoms from the same or two different carbon atoms of a parent alkyne. For example, and without being limiting, an alkynylene group can have 2 to 20 carbon atoms, 2 to 10 carbon atoms, 2 to 6 carbon atoms or 2 to 4 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡C—).

The term "Aryl", as used herein, means an aromatic hydrocarbon radical derived by the removal of one hydrogen atom from a single carbon atom of a parent aromatic ring system. For example, and without being limiting, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene and biphenyl.

The term "Arylalkyl", as used herein, means an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. For example, and without being limiting, the arylalkyl group can include 7 to 20 carbon atoms, e.g., the alkyl moiety is 1 to 6 carbon atoms and the aryl moiety is 6 to 14 carbon atoms.

The term "Arylalkenyl", as used herein, means an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups described herein, and the alkenyl portion of the arylalkenyl can include, for example, any of the alkenyl groups described herein. The arylalkenyl group can include 8 to 20 carbon atoms, e.g., the alkenyl moiety is 2 to 6 carbon atoms and the aryl moiety is 6 to 14 carbon atoms.

The term "Arylalkynyl", as used herein, means an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. For example, and without being limiting, the arylalkynyl group can include 8 to 20 carbon atoms, e.g., the alkynyl moiety is 2 to 6 carbon atoms and the aryl moiety is 6 to 14 carbon atoms.

The term "heterocycle", as used herein, means a group including a covalently closed ring wherein at least one atom forming the ring is a heteroatom. For example, and without being limiting, heterocyclic rings can be formed by three, four, five, six, seven, eight, nine, or more than nine atoms. Any number of those atoms can be heteroatoms (i.e., a heterocyclic ring can include one, two, three, four, five, six, seven, eight, nine, or more than nine heteroatoms). In heterocyclic rings including two or more heteroatoms, those two or more heteroatoms can be the same or different from one another. Heterocycles can be substituted. Binding to a heterocycle can be at a heteroatom or via a carbon atom. It should also be understood that in the present description, the term "heterocycle" also encompasses "heteroaryl" groups.

The term "protecting group", as used herein, means a moiety of a compound that masks or alters the properties of a functional group or the properties of the compound as a whole. The chemical substructure of a protecting group can greatly vary. One function of a protecting group is to serve as an intermediate in the synthesis of the parental active substance. Chemical protecting groups and strategies for protection/deprotection are well known in the art. See: "Protective Groups in Organic Chemistry", Theodora W. Greene (John Wiley & Sons, Inc., New York, 1991).

The term "substituted", as used herein in reference to alkyl, alkylene, alkoxy, alkenyl, alkynyl, alkenylene, aryl, alkynylene, etc., for example "substituted alkyl", "substituted alkylene", "substituted alkoxy"—"or substituted O(Alkyl)", "substituted alkenyl", "substituted alkynyl", "substituted alkenylene", "substituted aryl" and "substituted alkynylene", unless otherwise indicated, means alkyl, alkylene, alkoxy, alkenyl, alkynyl, alkenylene, aryl and alkynylene, respectively, in which one or more hydrogen atoms are each independently replaced with a non-hydrogen substituent.

Typical non-hydrogen substituents include, but are not limited to, —X, —R$^B$, —O$^-$, =O, —OR$^B$, —SR$^B$, —S$^-$, —NR$^B_2$, Si(R$^C$)$_3$, —N$^+$R$^B_3$, —NR$^b$-(Alk)-NR$^B_2$, —NR$^B$-(Alk)-N$^+$R$^B_3$, —NR$^B$-(Alk)-OR$^B$, —NR$^B$-(Alk)-OP(=O)(OR$^B$)(O$^-$), —NR$^B$-(Alk)-OP(=O)(OR$^B$)$_2$, —NR$^B$-(Alk)-Si(R$^C$)$_3$, —NR$^B$-(Alk)-SR$^B$, —O-(Alk)-NR$^B_2$, —O-(Alk)-N$^+$R$^B_3$, —O-(Alk)-OR$^B$, —O-(Alk)-OP(=O)(OR$^B$)(O$^-$), —O-(Alk)-OP(=O)(OR$^B$)$_2$, —O-(Alk)-Si(R$^C$)$_3$, —O-(Alk)-SR$^B$, =NR$^B$, —CX$_3$, —CN, —OCN, —SCN, —N=C=O, —NCS, —NO, —NO$_2$, =N$_2$, —N$_3$, —NHC(=O)R$^B$, —OC(=O)R$^B$, —NHC(=O)NR$^B_2$, —S(=O)$_2$—, —S(=O)$_2$OH, —S(=O)$_2$R$^B$, —OS(=O)$_2$OR$^B$, —S(=O)$_2$NR$^B_2$, —S(=O)R$^B$, —OP(=O)(OR$^B$)(O$^-$), —OP(=O)(OR$^B$)$_2$, —P(=O)(OR$^B$)$_2$, —P(=O)(O$^-$)$_2$, —P(=O)(OH)$_2$, —P(O)(OR$^B$)(O$^-$), —C(=O)R$^B$, —C(=O)X, —C(S)R$^B$, —C(O)OR$^B$, —C(O)O$^-$, —C(S)OR$^B$, —C(O)SR$^B$, —C(S)SR$^B$, —C(O)NR$^B_2$, —C(S)NR$^B_2$ or —C(=NR$^B$)NR$^B_2$ where each X is independently a halogen: F, C, Br, or I; each R$^B$ is independently H, alkyl, aryl, arylalkyl, a heterocycle, an alkyloxy group such as poly(ethyleneoxy), PEG or poly(methyleneoxy), or a protecting group; each R$^C$ is independently alkyl, O(alkyl) or O(tri-substituted silyl); and each Alk is independently alkylene, substituted alkylene, alkenylene, substituted alkenylene, alkynylene or substituted alkynylene. Unless otherwise indicated, when the term "substituted" is used in conjunction with groups such as arylalkyl, which have two or more moieties capable of substitution, the substituents can be attached to the aryl moiety, the alkyl moiety, or both.

Is should also be understood that the term "tri-substituted silyl" refers to a silyl group that is independently substituted with three functional groups selected from alkyl, alkenyl, alkynyl, aryl and arylalkyl. Non-limiting examples of tri-substituted silyl groups include trimethylsilyl and dimethylphenylsilyl.

The term "PEG" or "poly(ethylene glycol)", as used herein, is meant to encompass any water-soluble poly(ethylene oxide). Typically, substantially all, or all monomeric subunits are ethylene oxide subunits, though the PEG can contain distinct end capping moieties or functional groups. PEG chains of the present description can include one of the following structures: —(CH$_2$CH$_2$O)$_m$— or —(CH$_2$CH$_2$O)$_{m-1}$CH$_2$CH$_2$—, depending on if the terminal oxygen has been displaced, where m is an integer, optionally selected from 1 to 100, 1 to 50, 1 to 30, 5 to 30, 5 to 20 or 5 to 15. The PEG can be capped with an "end capping group" that is generally a non-reactive carbon-containing group attached to a terminal oxygen or other terminal atom of the PEG. Non-limiting examples of end capping groups can include alkyl, substituted alkyl, aryl, substituted aryl, alkenyl, substituted alkenyl, alkynyl, substituted alkynyl, CO(alkyl), CO(substituted alkyl), CO(alkenyl), CO(substituted alkenyl), CO(alkynyl) or CO(substituted alkynyl).

The term "natural amino acid", as used herein refers to the twenty natural amino acids. More specifically, the natural amino acid can be selected from the group consisting of: Alanine (Ala), Glycine (Gly), Isoleucine (Ile), Leucine (Leu), Proline (Pro), Valine (Val), Phenylalanine (Phe), Tryptophan (Trp), Tyrosine (Tyr), Aspartic acid (Asp), Glutamic acid (Glu), Arginine (Arg), Histidine (His), Lysine (Lys), Serine (Ser), Threonine (Thr), Cysteine (Cys), Methionine (Met), Asparagine (Asn) and Glutamine (Gln). The natural amino acids (except for Glycine) bear an asymmetric carbon (the alpha-carbon) that is of (S) configuration (also referred to as L-amino acids). It should be understood that the expression "natural amino acid attached to the compound by its amino group bonded to the alpha-carbon", as used herein, means that a hydrogen of the amino group bonded to the alpha-carbon is removed and replaced by a bond between the amino acid and the rest of the compound.

A person skilled in the art will recognize that substituents and other moieties of the compounds of the present description should be selected in order to provide an agriculturally useful compound which can be formulated into an acceptably stable agricultural composition that can be applied to plants. The definitions and substituents for various genus and subgenus of the compounds of the present description are described and illustrated herein. It should be understood by a person skilled in the art that any combination of the definitions and substituents described herein should not result in an inoperable species or compound. It should also be understood that the phrase "inoperable species or compound" means compound structures that violate relevant scientific principles (such as, for example, a carbon atom connecting to more than four covalent bonds) or compounds too unstable to permit isolation and formulation into agriculturally acceptable compositions.

Selected substituents of the compounds of the present description can be present to a recursive degree. In this context, "recursive substituent" means that a substituent may recite another instance of itself. Because of the recursive nature of such substituents, theoretically, a large number of compounds can be present in any given implementation. For example, $R^x$ includes a $R^y$ substituent. $R^y$ can be R. R can be WP. $V^3$ can be $W^4$ and $W^4$ can be R or include substituents including $R^y$. A person skilled in the art of organic chemistry understands that the total number of such substituents is to be reasonably limited by the desired properties of the compound intended. Such properties include, by way of example and not limitation, physical properties such as molecular weight, solubility or log P, application properties such as activity against the intended target, possibility of application to plants, and practical properties such as ease of synthesis. Typically, each recursive substituent can independently occur 20, 19, 18, 17, 16, 15, 14, 13, 12, 11, 10, 9, 8, 7, 6, 5, 4, 3, 2, 1, or 0, times in a given implementation. For example, each recursive substituent can independently occur 3 or fewer times in a given embodiment. Recursive substituents are an intended aspect of the compounds of the present description. A person skilled in the art of organic chemistry understands the versatility of such substituents.

The term "agriculturally acceptable salt", as used herein, refers to salts that exhibit pesticidal activity (i.e., that are active against one or more biotic stress) or that can improve resistance of a plant to one or more abiotic stress. The term also refers to salts that are or can be converted in plants, water or soil to a compound or salt that exhibits pesticidal activity or that can improve resistance of a plant to one or more abiotic stress. The "agriculturally acceptable salt" can be an agriculturally acceptable cation or agriculturally acceptable anion. Non-limiting examples of agriculturally acceptable cations can include cations derived from alkali or alkaline earth metals and cations derived from ammonia and amines. For example, agriculturally acceptable cations can include sodium, potassium, magnesium, alkylammonium and ammonium cations. Non-limiting examples of agriculturally acceptable anions can include halide, phosphate, alkylsulfate and carboxylate anions. For example, agriculturally acceptable anions can include chloride, bromide, methylsulfate, ethylsulfate, acetate, lactate, dimethyl phosphate or polyalkoxylated phosphate anions.

The term "optionally substituted", as used herein in reference to a particular moiety of the compounds of the present description, means a moiety wherein all substituents are hydrogen or wherein one or more of the hydrogens of the moiety can be replaced by substituents such as those listed under the definition of the term "substituted" or as otherwise indicated.

It will be understood that all enantiomers, diastereomers, and racemic mixtures, tautomers, polymorphs, and pseudopolymorphs of compounds within the scope of the formulae and compositions described herein and their agriculturally acceptable salts thereof, are embraced by the present description. All mixtures of such enantiomers and diastereomers are also within the scope of the present description.

A compound of the present description and its agriculturally acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. Pseudopolymorphs of the compounds of the present description may exist due to differences in crystal packing (packing pseudopolymorphism) or due to differences in packing between different conformers of the same molecule (conformational pseudopolymorphism). The description and depiction of the compounds of the present description is intended to include all polymorphs and pseudopolymorphs of the compounds and their agriculturally acceptable salts.

A compound of the present description and its agriculturally acceptable salts may also exist as an amorphous solid. As used herein, an amorphous solid is a solid in which there is no long-range order of the positions of the atoms in the solid. The description and depiction of the compounds of the present description is intended to include all amorphous forms of the compounds and their agriculturally acceptable salts.

The modifier "about" used in connection with a quantity is inclusive of the stated value and has the meaning dictated by the context. For example, the modifier "about" can include the degree of error associated with the measurement of the quantity.

For agricultural use (i.e., for application to plants), salts of the compounds of the present description are agriculturally acceptable salts. However, salts which are not agriculturally acceptable can also find use, for example, in the preparation or purification of an agriculturally acceptable compound. All salts, whether or not they are agriculturally acceptable salts, are therefore to be understood as within the scope of the present description.

It will be understood that the compounds described herein can be in their un-ionized, ionized, as well as zwitterionic form, and in combinations with various amounts of water (e.g., stoichiometric amounts of water) such as in hydrates.

Whenever a compound described herein is substituted with more than one of the same designated group, e.g., "$R^1$" or "$R^2$", then it will be understood that the groups may be the same or different, i.e., each group is independently selected. For example, in the expression "$Si(OR^7)_3$ with each $R^7$ being independently alkyl or aryl", it is understood that each $R^7$ can independently be selected from alkyl groups and aryl groups. $Si(OR^7)_3$ therefore includes both symmetrical groups where all three $R^7$ are the same and asymmetrical groups where at least one $R^7$ group is different from the other two $R^7$ groups, or where each $R^7$ group is different. It is also understood that this applies to all $R^q$ or $Z^q$ groups defined herein (e.g., q being selected from 1 to 17, from a to f or from A to C). A group "$Z^1$" will be understood to be necessarily the same as another group "$Z^2$" only when it is explicitly stated that "$Z^1=Z^2$".

The compounds described herein can also exist as tautomeric forms in certain cases. Although only one delocalized resonance structure will typically be depicted, all such forms are contemplated within the scope of the present description. For example, various tautomers can exist for the tetrapyrole ring systems described herein, and all their possible tautomeric forms are within the scope of the present description.

The term "growing medium", as used herein, refers to any soil (of any composition) or soil-free (e.g., hydroponic) medium that is suitable for growing and cultivating a plant. The growing medium can further include any naturally occurring and/or synthetic substance(s) that are suitable for growing and cultivating the plant. The phrase "any surface of the growing medium" or "a surface of the growing medium", as used herein, refers to a surface that is directly exposed to natural and/or simulated light and/or weather.

The term "applying", as used herein, refers to contacting a surface of the growing medium with at least one compound of the present description (e.g., combinations, compositions, solutions, emulsions including at least one compound of the present description), by any means known in the art (e.g., pouring, root bathing, soil drenching, drip irrigation, etc.), or contacting an area that is beneath the surface of the growing medium with at least one compound of the present description (e.g., by soil injection), or any combination thereof, or directly contacting the plant with at least one compound of the present description (e.g., spraying).

The term "crop plant", as used herein, refers to a non-woody plant, which is grown, tended to, and harvested in a cycle of one year or less as source of foodstuffs and/or energy. Non-limiting examples of crop plants include sugar cane, wheat, rice, corn (maize), potatoes, sugar beets, barley, sweet potatoes, cassava, soybeans, tomatoes, and legumes (beans and peas). The crop plant can be a monocot or a dicot.

The term "woody plant", as used herein, refers to a woody perennial plant having a single stem or trunk, and bearing lateral branches at some distance from the ground (e.g., a tree). The woody plant can be a deciduous tree, an evergreen tree (e.g., a coniferous) or a shrub. Non-limiting examples of woody plants include maple trees, citrus trees, apple trees, pear trees, oak trees, ash trees, pine trees, and spruce trees.

The term "turf grass", as used herein, refers to a cultivated grass that provides groundcover, for example a turf or lawn that is periodically cut or mowed to maintain a consistent height. Grasses belong to the Poaceae family, which is subdivided into six subfamilies, three of which include common turf grasses: the Festucoideae subfamily of cool-season turf grasses; and the Panicoideae and Eragrostoideae subfamiles of warm-season turf grasses. A limited number of species are in widespread use as turf grasses, generally meeting the criteria of forming uniform soil coverage and tolerating mowing and traffic. In general, turf grasses have a compressed crown that facilitates mowing without cutting off the growing point. In the present context, the term "turf grass" includes areas in which one or more grass species are cultivated to form relatively uniform soil coverage, including blends that are a combination of different cultivars of the same species, or mixtures that are a combination of different species and/or cultivars.

Non-limiting examples of turf grasses include: bluegrasses (e.g., Kentucky bluegrass), bentgrasses (e.g., creeping bentgrass), Redtop, fescues (e.g., red fescue), ryegrasses (e.g., annual ryegrass), wheatgrasses (e.g., crested wheatgrass), beachgrass, Brome grasses (e.g., Arizona Brome), cattails (e.g., sand cattail), Alkaligrass (*Puccinellia distans*), crested dog's-tail (*Cynosurus cristatus*), bermudagrass (*Cynodon* spp. such as *Cynodon dactylon*), hybrid bermudagrass (e.g., tifdwarf bermudagrass), Zoysiagrasses (e.g., *Zoysia japonica*), St. Augustinegrass (e.g., Bitter Blue St. Augustinegrass), Centipedegrass (*Eremochloa ophiuroides*), Carpetgrass (*Axonopus fissifolius*), Bahiagrass (*Paspalum notatum*), Kikuyugrass (*Pennisetum clandestinum*), Buffalograss (*Buchloe dactyloides*), Seashore *paspalum* (*Paspalum vaginatum*), Blue Grama (*Bouteloua gracilis*), Black Grama (*Bouteloua eriopoda*), Sideoats Grama (*Bouteloua curtipendula*), *Sporobolus* spp. (e.g., Alkali Sacaton), Sand Dropseed (*Sporobolus cryptandrus*), Prairie Dropseed (*Sporobolus heterolepis*), *Hordeum* spp. (e.g., California Barley), Common Barley, Meadow Barley, *Alopecurus* spp. (e.g., Creeping Foxtail and Meadow Foxtail), *Stipa* spp. (e.g., Needle & Thread), *Elymus* spp. (e.g., Blue Wildrye), Buffelgrass (*Cenchrus ciliaris*), Big Quaking Grass (*Briza maxima*), Big Bluestem (*Andropogon gerardii*), Little Bluestem (*Schizachyruim scoparium*), Sand Bluestem (*Andropogon hallii*), Deergrass (*Muhlenbergia rigens*), Eastern Gamagrass (*Tripsacum dactyloides*), Galleta (*Hilaria jamesi*), Tufted Hairgrass (*Deschampsia caespitosa*), Indian Rice Grass (*Oryzopsis hymenoides*), Indian Grass (*Sorghastrum nutans*), Sand Lovegrass (*Eragrostis trichodes*); Weeping Lovegrass (*Eragrostis curvula*), California Melic (*Melica californica*), Prairie Junegrass (*Koeleria pyramidata*), Prairie Sandreed (*Calamovilfa longifolia*), Redtop (*Agrostis alba*), Reed Canarygrass (*Phalaris arundinacea*), Sloughgrass (*Spartina pectinata*), Green Sprangletop (*Leptochloa dubia*), Bottlebush Squirreltail (*Sitanion hystrix*), *Panicum* Switchgrass (*virgatum*), and Purple Threeawn (*Aristida purpurea*).

The phrase "promoting the health of a plant", as used herein, includes at least one of controlling a disease, condition, or injury caused by a pest of a plant and increasing abiotic stress resistance or tolerance in a plant. In other words, the phrase "promoting the health of a plant" includes at least one of "controlling infection of a plant by one or more biotic agent", "controlling infestation of a plant by one or more insect" and "increasing resistance of a plant to one or more abiotic stress".

The phrase "controlling infection of a plant by a biotic agent", as used herein, means to diminish, ameliorate, or stabilize the infection and/or any other existing unwanted condition or side effect that is caused by the association of a microbial pathogen or infestation of an insect on the plant. The microbial pathogen can include fungi, bacteria (gram positive or gram negative), viruses, viroids, virus-like organisms, phytoplasma, etc.

The term "abiotic stress", as used herein, refers to environmental conditions that negatively impact growth, development, yield and yield quality of crop and other plants. below optimum levels. Non-limiting examples of abiotic stresses include, for example: photooxidative conditions, drought (water deficit), excessive watering (flooding, and submergence), extreme temperatures (chilling, freezing and heat), extreme levels of light (high and low), radiation (UV-B and UV-A), salinity due to excessive $Na^+$ (sodicity), chemical factors (e.g., pH), mineral (metal and metalloid) toxicity, deficiency or excess of essential nutrients, gaseous pollutants (ozone, sulfur dioxide), wind, mechanical factors, and other stressors.

As used herein, the term "increasing stress resistance" (and the like) refers to an increase in the ability of a plant to survive or thrive in stress conditions. Enhanced resistance or tolerance can be specific for a particular stressor, e.g., drought, excess water, nutrient deficiency, salt, cold, shade or heat, or multiple stressors. In some scenarios, increased resistance to one or more abiotic stresses can be exemplified by the reduction in degradation of quality of the plant, as compared to an untreated plant subjected to the same stress. In other scenarios, increased resistance to one or more abiotic stress can be exemplified by maintained or improved plant quality, as compared to an untreated plant subjected to the same stress.

Photosensitizer Compounds

As discussed above, photosensitizer compounds can be used to enable photodynamic inhibition of biotic agents (i.e., microbial pathogens and/or insects) that are present on plants. The photosensitizer compounds react to light by generating reactive oxygen species (ROS).

Depending on the type of ROS generated, photosensitizers can be classified into two classes, namely Type I photosensitizers and Type II photosensitizers. On the one hand, Type I photosensitizers form short lived free radicals through electron abstraction or transfer from a substrate when excited at an appropriate wavelength in the presence of oxygen. On the other hand, Type photosensitizers form a highly reactive oxygen state known as "singlet oxygen", also referred to herein as "reactive singlet oxygen species". Singlet oxygen species are generally relatively long lived and can have a large radius of action.

It should be understood that the photosensitizer compound can be metallated or non-metallated. When metallated, as can be the case for various nitrogen-bearing macrocyclic compounds that are complexed with a metal, the metal can be selected to generate either a Type I or a Type photosensitizer in response to light exposure. For example, when porphyrin photosensitizer compounds are metallated with copper, the ROS that are generated are typically Type I photosensitizers. When the same porphyrin photosensitizer compounds are metallated with magnesium, the ROS that are generated are typically Type photosensitizers. Both Type I and Type photosensitizers can be used to enable photodynamic inhibition of biotic agents that are present on plants or to protect a plant from abiotic stress.

It should be understood that the term "singlet oxygen photosensitizer", as used herein, refers to a compound that produces reactive singlet oxygen species when excited by light. In other words, the term "singlet oxygen photosensitizer" refers to a photosensitizer in which the Type II process defined above is dominant compared to the Type I process.

Protoporphyrin IX (PP IX) is an organic compound, which is one of the most common porphyrins in nature. PP IX is a deeply colored pigment that is not very soluble even in basic water. PP IX is encountered in nature in the form of its iron complexes. When complexed with ferrous iron, the molecule is called heme. Other iron complexes have also been synthesized, for example with Fe(III) or Fe(IV). PP IX is a largely planar tetrapyrrole having a 20-carbon atom macrocyclic ring, each pyrrole being linked to two other pyrroles of the macrocyclic ring by a one-carbon bridge. It will be understood that by "tetrapyrrole", it is meant four pyrrole-like rings. As used herein, a "pyrrole-like" ring is a five-atom ring with four carbon atoms and one nitrogen atom. In the depiction of PP IX below, the carbons of the macrocyclic ring are numbered from 1 to 20. In the chemical structure of PP IX, two carboxylic acid-bearing moieties are provided at the C13 ($CH_2CH_2COOH$) and C17 ($CH_2CH_2COOH$) positions.

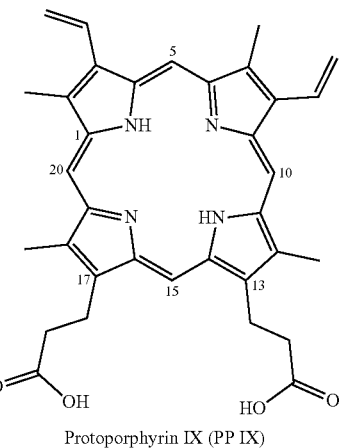

Protoporphyrin IX (PP IX)

The compounds of the present description include photosensitizer compounds based on or similar to the PP IX scaffold above, that are of general Formula I represented below, or an agriculturally acceptable salt thereof. In what follows, the term "photosensitizer compound" refers to one or more compounds of Formula I. In other words, the term "photosensitizer compound" can refer to one compound of Formula I or to a combination or mixture of two or more compounds of Formula I.

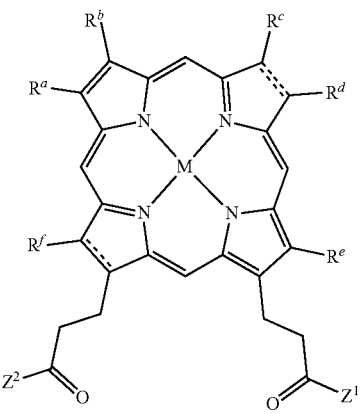

Formula I

In one aspect, there is provided a compound of Formula I, or an agriculturally acceptable salt thereof, wherein:

$Z^1$ and $Z^2$ are each independently $OR^1$ or $NR^2R^3$;

each $R^1$, $R^2$ and $R^3$ is independently H, alkyl, substituted alkyl, aryl, substituted aryl, alkenyl, substituted alkenyl, alkynyl, or substituted alkynyl, wherein:

if $Z^1$ and $Z^2$ are both $OR^1$ then at least one $R^1$ is not H, if $Z^1$ and $Z^2$ are both $NR^2R^3$ then at least one $R^3$ is not H, and if one of $Z^1$ and $Z^2$ is $OR^1$ and the other one of $Z^1$ and $Z^2$ is $NR^2R^3$, then at least one of $R^1$ and $R^3$ is not H;

each $R^a$, $R^b$, $R^c$, $R^d$, $R^e$ and $R^f$ is, independently, H, alkyl, substituted alkyl, aryl, substituted aryl, alkenyl, substituted alkenyl, alkynyl or substituted alkynyl;

===== is a single bond or a double bond;

===== is a single bond or a double bond; and

M is 2H or a metal species, wherein the substituted alkyl, substituted aryl, substituted alkenyl and substituted alkynyl groups are, independently, substituted with one or more —X, —$R^B$, —$O^-$, =O, —$OR^B$, —$SR^B$, —$S^-$, —$NR^B{}_2$, $Si(R^C)_3$, —$N^+R^B{}_3$, —$NR^B$-(Alk)-$NR^B{}_2$, —$NR^B$-(Alk)-$N^+R^B{}_3$, —$NR^B$-(Alk)-$OR^B$, —$NR^B$-(Alk)-OP(=O)($OR^B$)($O^-$), —$NR^B$-(Alk)-OP(=O)($OR^B$)$_2$, —$NR^B$-(Alk)-$Si(R^C)_3$, —$NR^B$-(Alk)-$SR^B$, —O-(Alk)-$NR^B{}_2$, —O-(Alk)-$N^+R^B{}_3$, —O-(Alk)-$OR^B$, —O-(Alk)-OP(=O)($OR^B$)($O^-$), —O-(Alk)-OP(=O)($OR^B$)$_2$, —O-(Alk)-$Si(R^C)_3$, —O-(Alk)-$SR^B$, =$NR^B$, —$CX_3$, —CN, —OCN, —SCN, —N=C=O, —NCS, —NO, —$NO_2$, =$N_2$, —$N_3$, —NHC(=O)$R^B$, —OC(=O)$R^B$, —NHC(=O)$NR^B{}_2$, —S(=O)$_2$—, —S(=O)$_2$OH, —S(=O)$_2R^B$, —OS(=O)$_2OR^B$, —S(=O)$_2NR^B{}_2$, —S(=O)$R^B$, —OP(=O)($OR^B$)($O^-$), —OP(=O)($OR^B$)$_2$, —P(=O)($OR^B$)$_2$, —P(=O)($O^-$)$_2$, —P(=O)(OH)$_2$, —P(O)($OR^B$)($O^-$), —C(=O)$R^B$, —C(=O)X, —C(S)$R^B$, —C(O)$OR^B$, —C(O)—, —C(S)$OR^B$, —C(O)$SR^B$, —C(S)$SR^B$, —C(O)$NR^B{}_2$, —C(S)$NR^B{}_2$ or —C(=$NR^B$)$NR^B{}_2$;

each X is independently a halogen: F, Cl, Br or I;

each $R^B$ is independently H, alkyl, aryl, arylalkyl, a heterocycle, an alkyloxy group such as poly(ethyleneoxy), PEG or poly(methyleneoxy), a capped poly(ethyleneoxy), capped PEG or capped polymethyleneoxy, or a protecting group;

the capped poly(ethyleneoxy), capped PEG and capped poly(methyleneoxy) groups being each independently capped with alkyl, aryl, arylalkyl, alkenyl, alkynyl, CO(alkyl), CO(aryl), CO(arylalkyl), CO(alkenyl) or CO(alkynyl);

each $R^C$ is independently alkyl, aryl, arylalkyl, O(alkyl), O(aryl), O(arylalkyl), or O(tri-substituted silyl);

each tri-substituted silyl is independently substituted with three functional groups selected from alkyl, alkenyl, alkynyl, aryl and arylalkyl; and each Alk is independently alkylene, alkenylene, or alkynylene.

In some implementations, the compound of Formula I is such that:

one of $Z^1$ and $Z^2$ is $OR^1$; and the other one of $Z^1$ and $Z^2$ is $NR^2R^3$, $NR^2$—$(CH_2)_n$—$NR^4R^5$, $NR^2$—$(CH_2)_n$—$N^+R^4R^5R^6$ $Y^-$, $NR^2$—$(CH_2)_n$—O(PO$_3$H)$^-$ $W^+$, $NR^2$—$(CH_2)_n$—Si($R^7$)$_3$, $NR^2$—$(CH_2)_n$—$SR^8$, $NR^2$—$(CH_2)_n$—$NR^4$—$(CH_2)_p$—$NR^9R^{10}$, $NR^2$—$(CH_2)_n$—$NR^4$—$(CH_2)_p$—$N^+R^9R^{10}R^{11}$ $Y^-$, $NR^2$—$(CH_2)_n$—$NR^4$—$(CH_2)_p$—O(PO$_3$H)$^-$ $W^+$, $NR^2$—$(CH_2)_n$—$NR^4$—$(CH_2)_p$—Si($R^7$)$_3$, $NR^2$—$(CH_2)_n$—$NR^4$—$(CH_2)_p$—$SR^8$, $O(CH_2)_n$—$NR^4R^5$, $O(CH_2)_n$—$N^+R^4R^5R^6$ $Y^-$, $O(CH_2)_n$—O(PO$_3$H)$^-$ $W^+$, $O(CH_2)_n$—Si($R^7$)$_3$, $O(CH_2)_n$—$SR^8$, $O(CH_2)_n$—$NR^4$—$(CH_2)_p$—$NR^9R^{10}$, $O(CH_2)_n$—$NR^4$—$(CH_2)_p$—$N^+R^9R^{10}R^{11}$ $Y^-$, $O(CH_2)_n$—$NR^4$—$(CH_2)_p$—O(PO$_3$H)$^-$ $W^+$ or $O(CH_2)_n$—$NR^4$—$(CH_2)_p$—Si($R^7$)$_3$;

or $Z^1$ is $NR^2R^3$, $NR^2$—$(CH_2)_n$—$NR^4R^5$, $NR^2$—$(CH_2)_n$—$N^+R^4R^5R^6$ $Y^-$, $NR^2$—$(CH_2)_n$—O(PO$_3$H)$^-$ $W^+$, $NR^2$—$(CH_2)_n$—Si($R^7$)$_3$, $NR^2$—$(CH_2)_n$—$SR^8$, $NR^2$—$(CH_2)_n$—$NR^4$—$(CH_2)_p$—$NR^9R^{10}$, $NR^2$—$(CH_2)_n$—$NR^4$—$(CH_2)_p$—$N^+R^9R^{10}R^{11}$ $Y^-$, $NR^2$—$(CH_2)_n$—$NR^4$—$(CH_2)_p$—O(PO$_3$H)$^-$ $W^+$, $NR^2$—$(CH_2)_n$—$NR^4$—$(CH_2)_p$—Si($R^7$)$_3$, $NR^2$—$(CH_2)_n$—$NR^4$—$(CH_2)_p$—$SR^8$, $O(CH_2)_n$—$NR^4R^5$, $O(CH_2)_n$—$N^+R^4R^5R^6$ $Y^-$, $O(CH_2)_n$—O(PO$_3$H)$^-$ $W^+$, $O(CH_2)_n$—Si($R^7$)$_3$, $O(CH_2)_n$—$SR^8$, $O(CH_2)_n$—$NR^4$—$(CH_2)_p$—$NR^9R^{10}$, $O(CH_2)_n$—$NR^4$—$(CH_2)_p$—$N^+R^9R^{10}R^{11}$ Y $O(CH_2)_n$—$NR^4$—$(CH_2)_p$—O(PO$_3$H)$^-$ $W^+$ or $O(CH_2)_n$—$NR^4$—$(CH_2)_p$—Si($R^7$)$_3$; and $Z^2$=$Z^1$;

each $R^1$ and $R^2$ is, independently, H, alkyl, substituted alkyl, aryl, substituted aryl, alkenyl, substituted alkenyl, alkynyl or substituted alkynyl;

$R^3$ is alkyl, substituted alkyl, aryl, substituted aryl, alkenyl, substituted alkenyl, alkynyl or substituted alkynyl;

each $R^4$, $R^6$, $R^8$, $R^9$, $R^{10}$ and $R^{11}$ is, independently, H, alkyl, substituted alkyl, aryl, substituted aryl, alkenyl, substituted alkenyl, alkynyl, substituted alkynyl or —$(CH_2)_q$—$(CH_2CH_2O)_m$—$R^{13}$;

$R^5$ is alkyl, substituted alkyl, aryl, substituted aryl, alkenyl, substituted alkenyl, alkynyl, substituted alkynyl or —$(CH_2)_q$—$(CH_2CH_2O)_m$—$R^{13}$;

$R^7$ is alkyl, O(alkyl) or O(tri-substituted silyl);

$R^{13}$ is H, alkyl, substituted alkyl, aryl, substituted aryl, alkenyl, substituted alkenyl, alkynyl, substituted alkynyl, CO(alkyl), CO(substituted alkyl), CO(alkenyl), CO(substituted alkenyl), CO(alkynyl) or CO(substituted alkynyl);

$W^+$ is an agriculturally acceptable cation;

$Y^-$ is an agriculturally acceptable anion;

n is an integer selected from 1 to 16;

p is an integer selected from 1 to 16;

m is an integer selected from 1 to 100;

q is an integer selected from 0 to 16;

each $R^a$, $R^b$, $R^c$, $R^d$, $R^e$ and $R^f$ is, independently, H, alkyl, substituted alkyl, aryl, substituted aryl, alkenyl, substituted alkenyl, alkynyl or substituted alkynyl;

===== is a single bond or a double bond;

===== is a single bond or a double bond; and

M is 2H or a metal species, wherein each substituted alkyl, substituted aryl, substituted alkenyl and substituted alkynyl groups are, independently, substituted with one or more OH, F, Cl, Br, I, CN and $N_3$.

In some implementations, $Z^1=Z^2=NR^2R^3$. In other implementations, $Z^1$ is $NR^2R^3$ and $Z^2$ is OH, or $Z^1$ is OH and $Z^2$ is $NR^2R^3$. $R^3$ can for example be alkyl or substituted alkyl.

In some implementations, ====== is a double bond and/or ====== is a double bond. More specifically: in some scenarios, ====== is a double bond and ====== is a double bond. In other scenarios, ====== is a double bond and ====== is a single bond. In yet other scenarios, ====== is a single bond and ====== is a double bond. In yet other scenarios, ====== is a single bond and ====== is a single bond.

In some implementations, each $R^a$, $R^b$, $R^c$, $R^d$, $R^e$ and $R^f$ is, independently, alkyl or alkenyl. In a non-limiting example, $R^a$, $R^c$, $R^e$ and $R^f$ are methyl while $R^b$ and $R^d$ are vinyl.

In some implementations, M is 2H. In some implementations, M is a metal species selected from the group consisting of Mg, Zn, Pd, Sn, Al, Pt, Si, Ge, Ga, In, Cu, Co, Fe and Mn. It should be understood that when a metal species is mentioned without its degree of oxidation, all suitable oxidation states of the metal species are to be considered, as would be understood by a person skilled in the art. In other implementations, M is a metal species selected from the group consisting of Mg(II), Zn(II), Pd(II), Sn(IV), Al(III), Pt(II), Si(IV), Ge(IV), Ga(III) and In(III). In yet other implementations, M is a metal species selected from the group consisting of Cu(II), Co(II), Fe(II) and Mn(II). In yet other implementations, M is a metal species selected from the group consisting of Cu(II), Co(III), Fe(III) and Mn(III).

In some implementations, each $R^1$, $R^2$, $R^4$, $R^6$, $R^8$, $R^9$, $R^{10}$ and $R^{11}$ is, independently, H, alkyl or substituted alkyl. In some implementations, each $R^3$ and $R^5$ is, independently, alkyl or substituted alkyl. In some implementations, $R^{13}$ is H, alkyl, substituted alkyl, CO(alkyl) or CO(substituted alkyl).

In some implementations, the compound of Formula I is selected such that at least one of the following is true: $R^1$ is H, $R^2$ is H, $R^3$ is alkyl, $R^4$ is H or alkyl, $R^5$ is alkyl, $R^6$ is alkyl, $R^7$ is O(tri-substituted silyl), $R^8$ is H or alkyl, $R^9$ is alkyl, $R^{10}$ is alkyl, $R^{11}$ is alkyl and $R^{13}$ is H, alkyl, alkenyl, CO(alkyl) or CO(alkenyl).

In some implementations, $W^+$ is selected from the group consisting of sodium, potassium, magnesium and ammonium cations. In some implementations, $Y^-$ is selected from the group consisting of chloride, bromide, phosphate, dimethylphosphate, methylsulfate, ethylsulfate, acetate and lactate.

In some implementations, n is an integer selected from 1 to 16, or from 1 to 12, or from 1 to 8, or from 1 to 6, or from 1 to 4, or from 2 to 4. Similarly, in some implementations, p is an integer selected from 1 to 16, or from 1 to 12, or from 1 to 8, or from 1 to 6, or from 1 to 4, or from 2 to 4. Regarding the PEG moieties, m is an integer that can be selected from 1 to 100, or from 1 to 80, or from 1 to 60, or from 1 to 50, or from 1 to 30, or from 1 to 20, or from 1 to 10, or from 5 to 30, or from 5 to 20, or from 5 to 10. Still regarding PEG moieties, q is an integer that can be selected from 0 to 16, or from 0 to 8, or from 0 to 4, or from 0 to 2.

In some implementations, q=1. In other implementations, 1=0.

In some implementations, $Z^1$ is $NR^2R^3$, $NR^2$—$(CH_2)_n$—$NR^4R^5$, $NR^2$—$(CH_2)_n$—$N^+R^4R^5R^6$ $Y^-$, $NR^2$—$(CH_2)_n$—$O(PO_3H)^-$ $W^+$, $NR^2$—$(CH_2)_n$—$Si(R^7)_3$, $NR^2$—$(CH_2)_n$—$SR^8$, $NR^2$—$(CH_2)_n$—$NR^4$—$(CH_2)_p$—$NR^9R^{10}$, $NR^2$—$(CH_2)_n$—$NR^4$—$(CH_2)_p$—$N^+R^9R^{10}R^{11}$ $Y^-$, $NR^2$—$(CH_2)_n$—$NR^4$—$(CH_2)_p$—$O(PO_3H)^-$ $W^+$, $NR^2$—$(CH_2)_n$—$NR^4$—$(CH_2)_p$—$Si(R^7)_3$, $NR^2$—$(CH_2)_n$—$NR^4$—$(CH_2)_p$—$SR^8$, $O(CH_2)_n$—$NR^4R^5$, $O(CH_2)_n$—$N^+R^4R^5R^6$ $Y^-$, $O(CH_2)_n$—$O(PO_3H)^-$ $W^+$, $O(CH_2)_n$—$Si(R^7)_3$, $O(CH_2)_n$—$SR^8$, $O(CH_2)_n$—$NR^4$—$(CH_2)_p$—$NR^9R^{10}$, $O(CH_2)_n$—$NR^4$—$(CH_2)_p$—$N^+R^9R^{10}R^{11}$ $Y^-$, $O(CH_2)_n$—$NR^4$—$(CH_2)_p$—$O(PO_3H)^-$ $W^+$ or $O(CH_2)_n$—$NR^4$—$(CH_2)_p$—$Si(R^7)_3$; and $Z^2=Z^1$.

In some implementations, one of $Z^1$ and $Z^2$ is $NR^2R^3$, $NR^2$—$(CH_2)_n$—$NR^4R^5$, $NR^2$—$(CH_2)_n$—$N^+R^4R^5R^6$ $Y^-$, $NR^2$—$(CH_2)_n$—$O(PO_3H)^-$ $W^+$, $NR^2$—$(CH_2)_n$—$Si(R^7)_3$, $NR^2$—$(CH_2)_n$—$SR^8$ or $NR^2$—$(CH_2)_n$—$NR^4$—$(CH_2)_p$—$NR^9R^{10}$; and the other one of $Z^1$ and $Z^2$ is $OR^1$; or $Z^1$ is $NR^2R^3$, $NR^2$—$(CH_2)_n$—$NR^4R^5$, $NR^2$—$(CH_2)_n$—$N^+R^4R^5R^6$ $Y^-$, $NR^2$—$(CH_2)_n$—$O(PO_3H)^-$ $W^+$, $NR^2$—$(CH_2)_n$—$Si(R^7)_3$, $NR^2$—$(CH_2)_n$—$SR^8$ or $NR^2$—$(CH_2)_n$—$NR^4$—$(CH_2)_p$—$NR^9R^{10}$; and $Z^2=Z^1$.

In some implementations, one of $Z^1$ and $Z^2$ is $NR^2R^3$, $NR^2$—$(CH_2)_n$—$NR^4R^5$, $NR^2$—$(CH_2)_n$—$N^+R^4R^5R^6$ $Y^-$, $NR^2$—$(CH_2)_n$—$O(PO_3H)^-$ $W^+$, $NR^2$—$(CH_2)_n$—$Si(R^7)_3$, $NR^2$—$(CH_2)_n$—$SR^8$ or $NR^2$—$(CH_2)_n$—$NR^4$—$(CH_2)_p$—$NR^9R^{10}$; and the other one of $Z^1$ and $Z^2$ is $OR^1$.

In some implementations, $Z^1$ is $NR^2R^3$, $NR^2$—$(CH_2)_n$—$NR^4R^5$, $NR^2$—$(CH_2)_n$—$N^+R^4R^5R^6$ $Y^-$, $NR^2$—$(CH_2)_n$—$O(PO_3H)^-$ $W^+$, $NR^2$—$(CH_2)_n$—$Si(R^7)_3$, $NR^2$—$(CH_2)_n$—$SR^8$ or $NR^2$—$(CH_2)_n$—$NR^4$—$(CH_2)_p$—$NR^9R^{10}$; and $Z^2=Z^1$.

In another aspect, there is provided a compound of Formula I-B1:

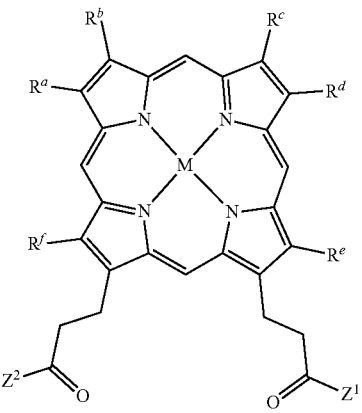

Formula I-B1 or an agriculturally acceptable salt thereof, for use in promoting the health of a plant, wherein:
one of $Z^1$ and $Z^2$ is $NR^2R^3$; and
the other one of $Z^1$ and $Z^2$ is $OR^1$;
or
$Z^1=NR^2R^3$; and
$Z^2=Z^1$;
each $R^1$ and $R^2$ is, independently, H, alkyl or substituted alkyl;
$R^3$ is alkyl or substituted alkyl;
each $R^a$, $R^b$, $R^c$, $R^d$, $R^e$ and $R^f$ is, independently, H, alkyl, substituted alkyl, alkenyl, substituted alkenyl, alkynyl or substituted alkynyl; and
M is 2H or a metal species,
wherein the substituted alkyl, substituted alkenyl and substituted alkynyl groups are, independently, substituted with one or more OH, F, Cl, Br, I, CN and $N_3$.

In some implementations, $R^1$ is H, $R^2$ is H and/or $R^3$ is alkyl. $R^3$ can for example be a $(C_1-C_{12})$alkyl, a $(C_1-C_8)$alkyl or a $(C_1-C_4)$alkyl. In some implementations, one of $Z^1$ and $Z^2$ is $NR^2R^3$; and the other one of $Z^1$ and $Z^2$ is $OR^1$. In other implementations, $Z^1 = NR^2R^3$; and $Z^2 = Z^1$.
In some implementations, the compound of Formula I-B1 is:
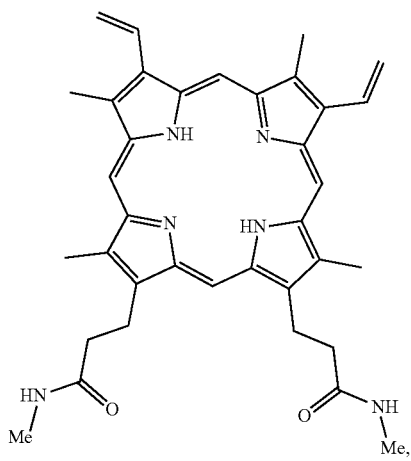
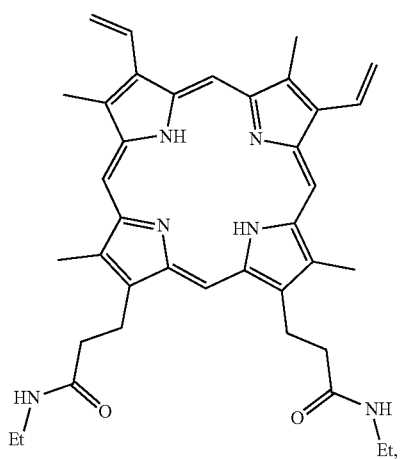
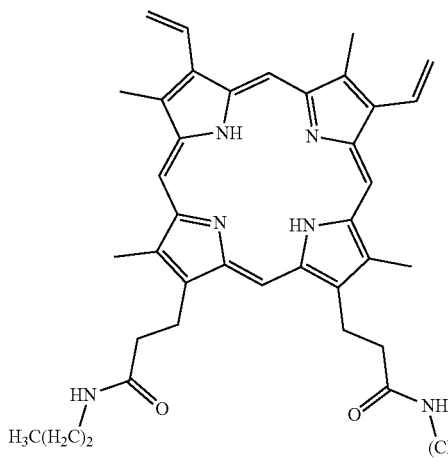
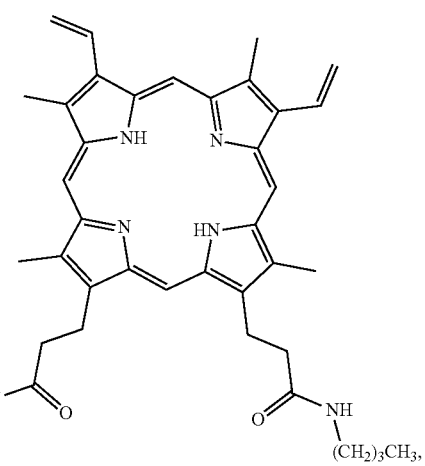
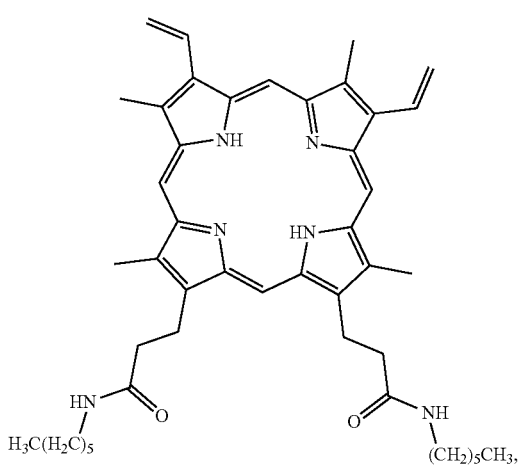
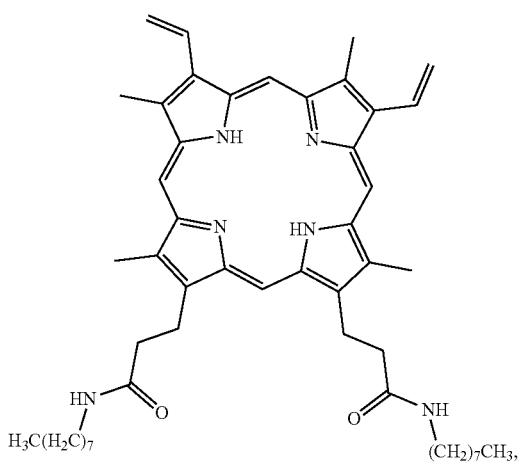

-continued
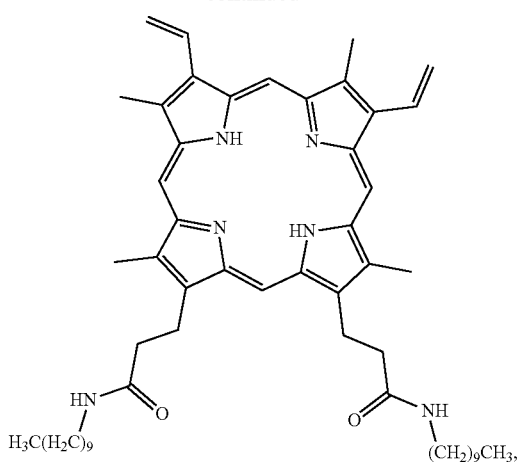
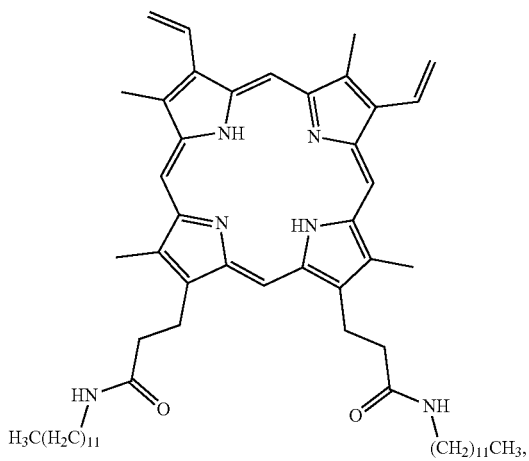
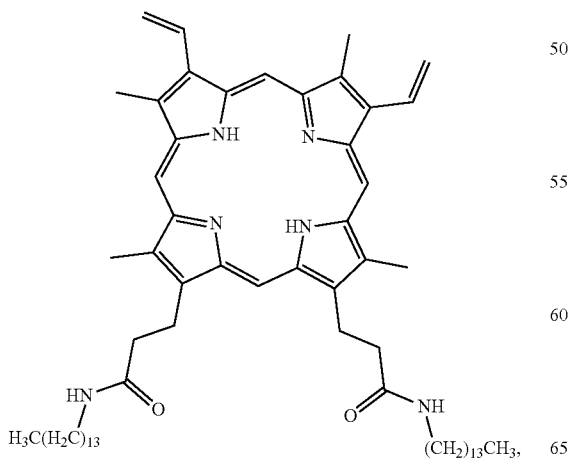
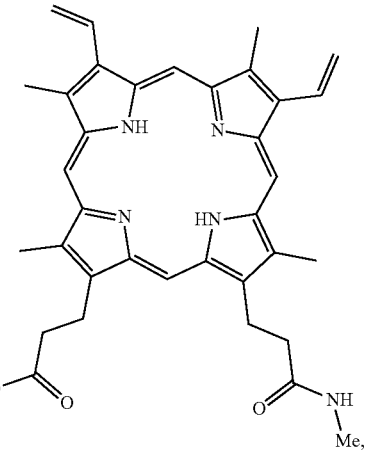
or an agriculturally acceptable salt thereof.
In some implementations, the compound of Formula I-B1 is:
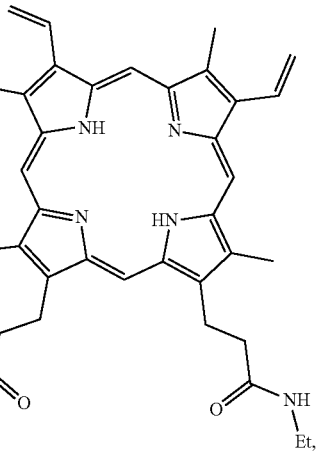

27
-continued
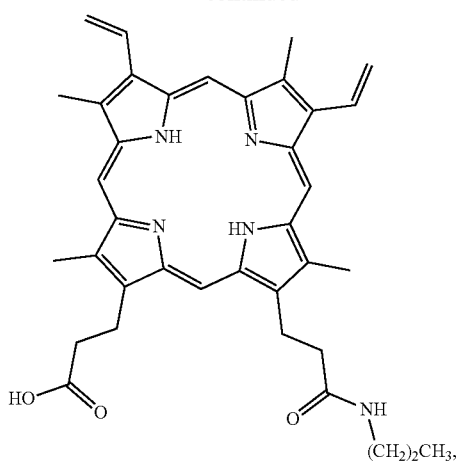
28
-continued
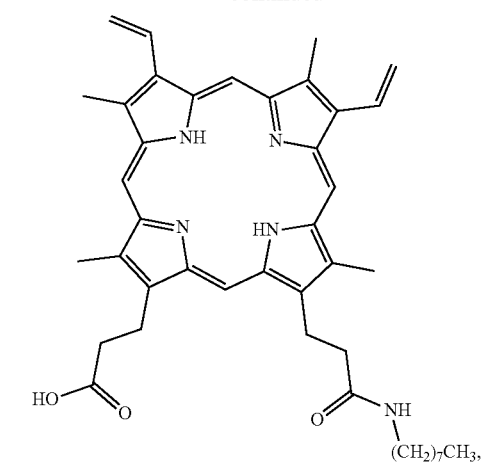
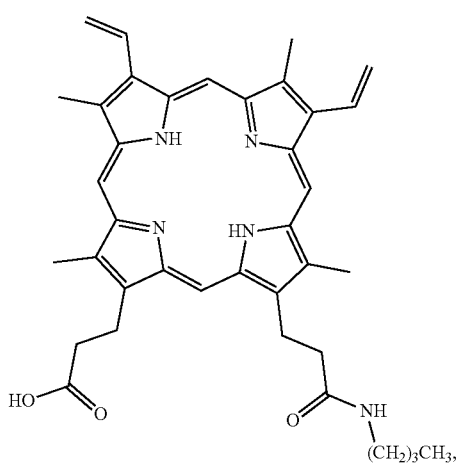
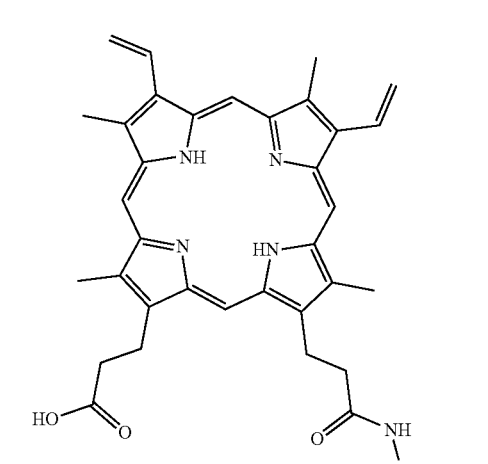
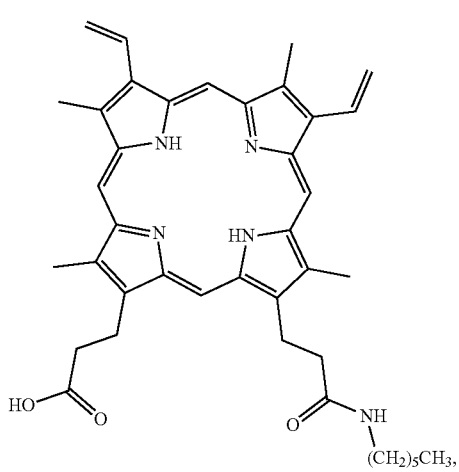
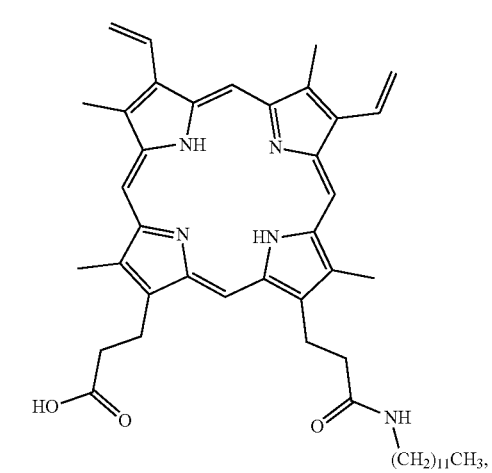

-continued
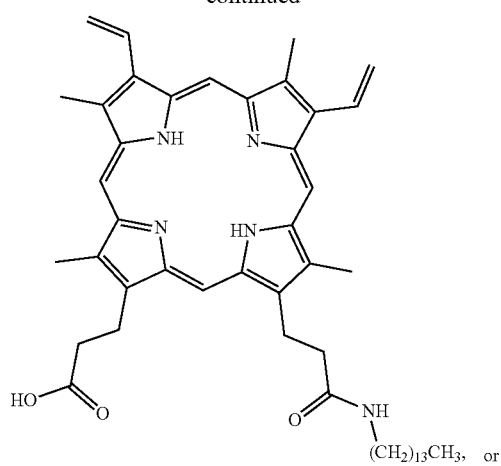
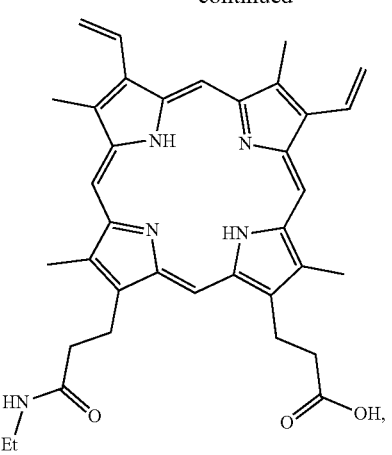
or
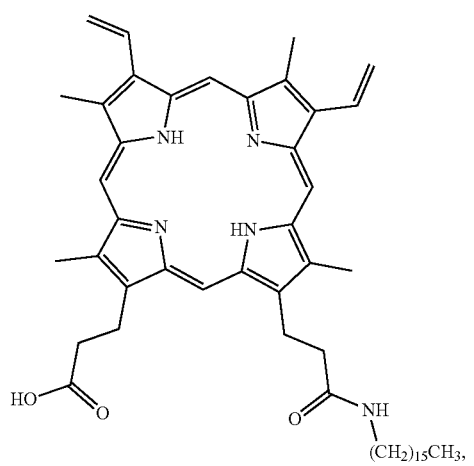
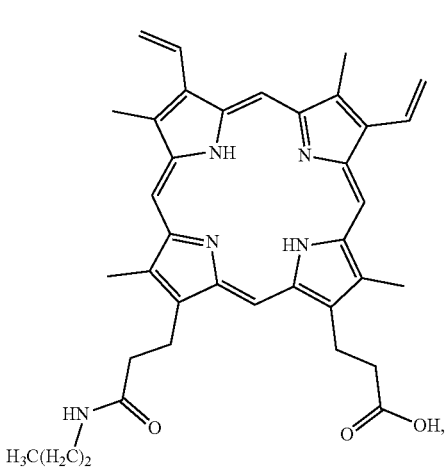
or an agriculturally acceptable salt thereof.
In some implementations, the compound of Formula I-B1 is:
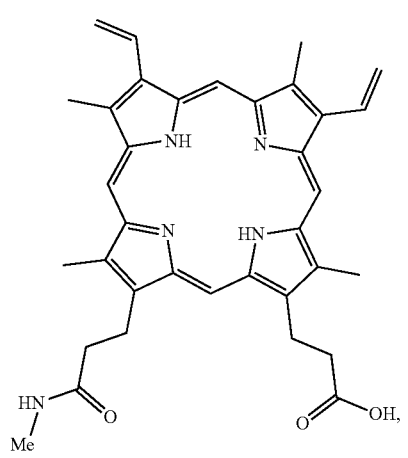
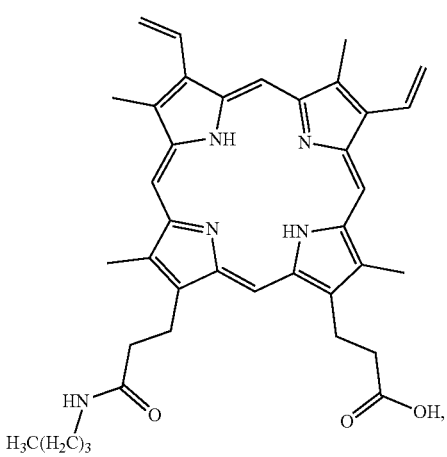

31
-continued
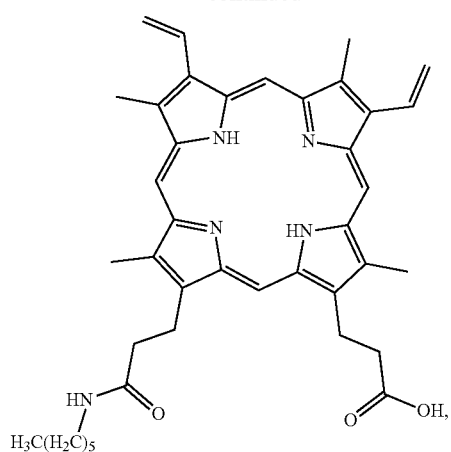
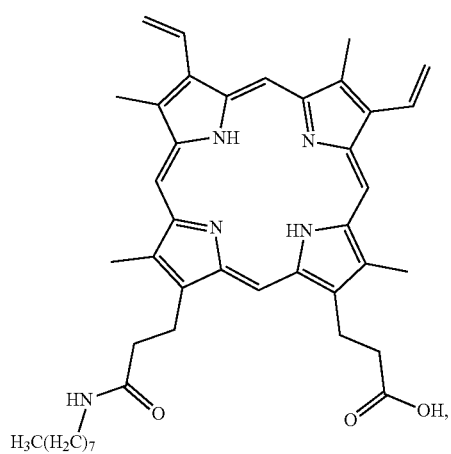
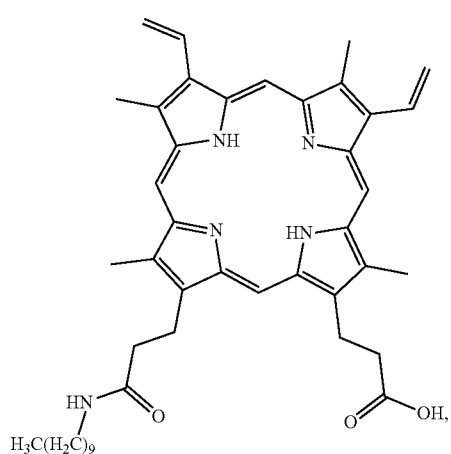
32
-continued
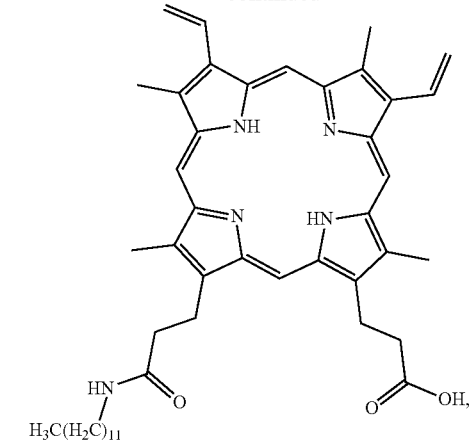
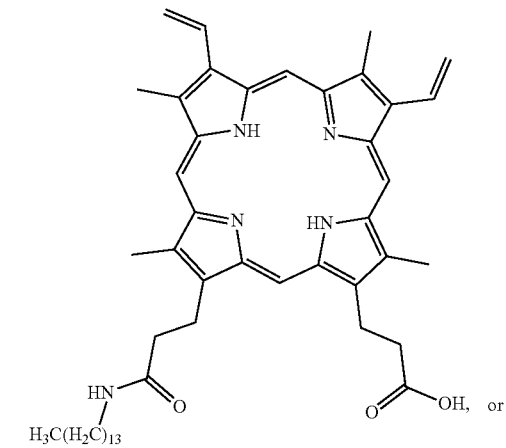
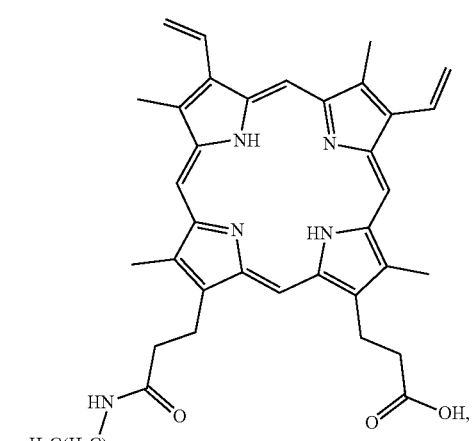
or an agriculturally acceptable salt thereof.
In another aspect, there is provided a compound of Formula I-B1:

Formula I-B1

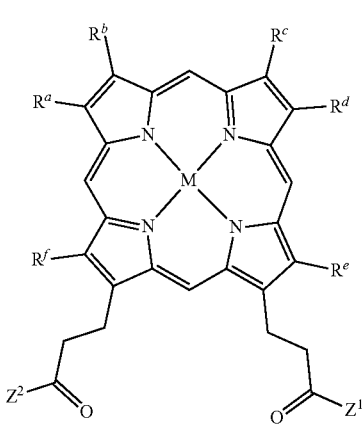

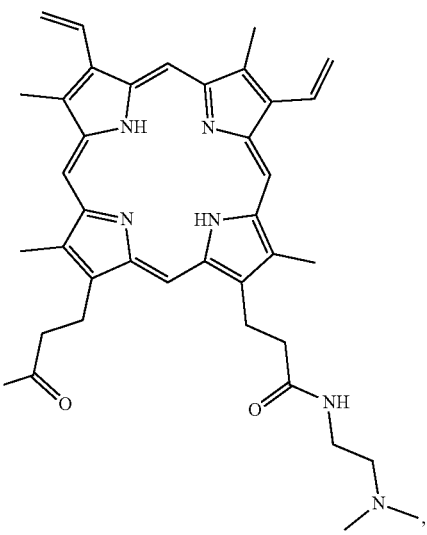

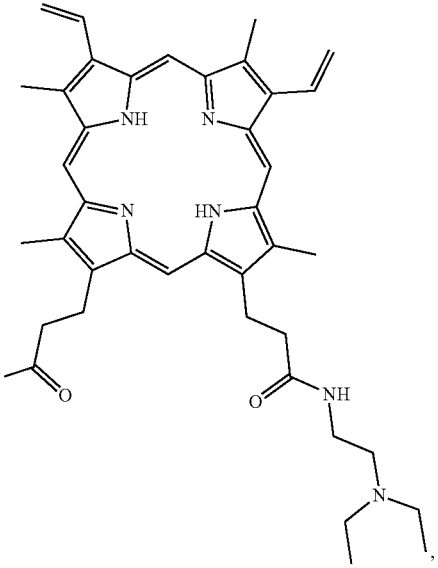

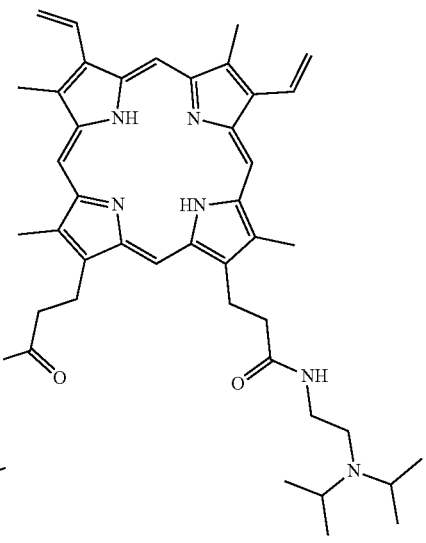

or an agriculturally acceptable salt thereof, for use in promoting the health of a plant, wherein:

one of $Z^1$ and $Z^2$ is $NR^2-(CH_2)_n-NR^4R^5$ or $O-(CH_2)_n-NR^4R^5$; and the other one of $Z^1$ and $Z^2$ is $OR^1$;

or $Z^1=NR^2-(CH_2)_n-NR^4R^5$ or $O-(CH_2)_n-NR^4R^5$; and $Z^2=Z^1$;

$R^5$ is alkyl, substituted alkyl or $-(CH_2)_p-NR^9R^{10}$;

each $R^1$, $R^2$, $R^4$, $R^9$ and $R^{10}$ is, independently, H, alkyl or substituted alkyl;

n is an integer selected from 1 to 16;

p is an integer selected from 1 to 16;

each $R^a$, $R^b$, $R^c$, $R^d$, $R^e$ and $R^f$ is, independently, H, alkyl, substituted alkyl, alkenyl, substituted alkenyl, alkynyl or substituted alkynyl; and M is 2H or a metal species, wherein the substituted alkyl, substituted alkenyl and substituted alkynyl groups are, independently, substituted with one or more OH, F, Cl, Br, I, CN and $N_3$.

In some implementations, $R^1$ is H, $R^2$ is H and/or $R^4$ is H or alkyl. In some implementations, $R^4$ is H and $R^5$ is alkyl. In some implementations, $R^4$ and $R^5$ are alkyl. $R^4$ and/or $R^5$ can for example each independently be a $(C_1-C_{12})$alkyl, a $(C_1-C_8)$alkyl or a $(C_1-C_4)$alkyl. In some implementations, $R^5$ is $-(CH_2)_p-NR^9R^{10}$. In some implementations, $R^9$ and $R^{10}$ are alkyl, or $R^9$ is H and $R^{10}$ is alkyl. $R^9$ and/or $R^{10}$ can for example each independently be a $(C_1-C_{12})$alkyl, a $(C_1-C_8)$alkyl or a $(C_1-C_4)$alkyl.

In some implementations, n is an integer selected from 1 to 16, or from 1 to 12, or from 1 to 8, or from 1 to 6, or from 1 to 4, or from 2 to 4. In some implementations, p is an integer selected from 1 to 16, or from 1 to 12, or from 1 to 8, or from 1 to 6, or from 1 to 4, or from 2 to 4.

In some implementations, one of $Z^1$ and $Z^2$ is $NR^2-(CH_2)_n-NR^4R^5$; and the other one of $Z^1$ and $Z^2$ is $OR^1$. In other implementations, $Z^1=NR^2-(CH_2)_n-NR^4R^5$; and $Z^2=Z^1$.

In some implementations, the compound of Formula I-B1 is:

-continued
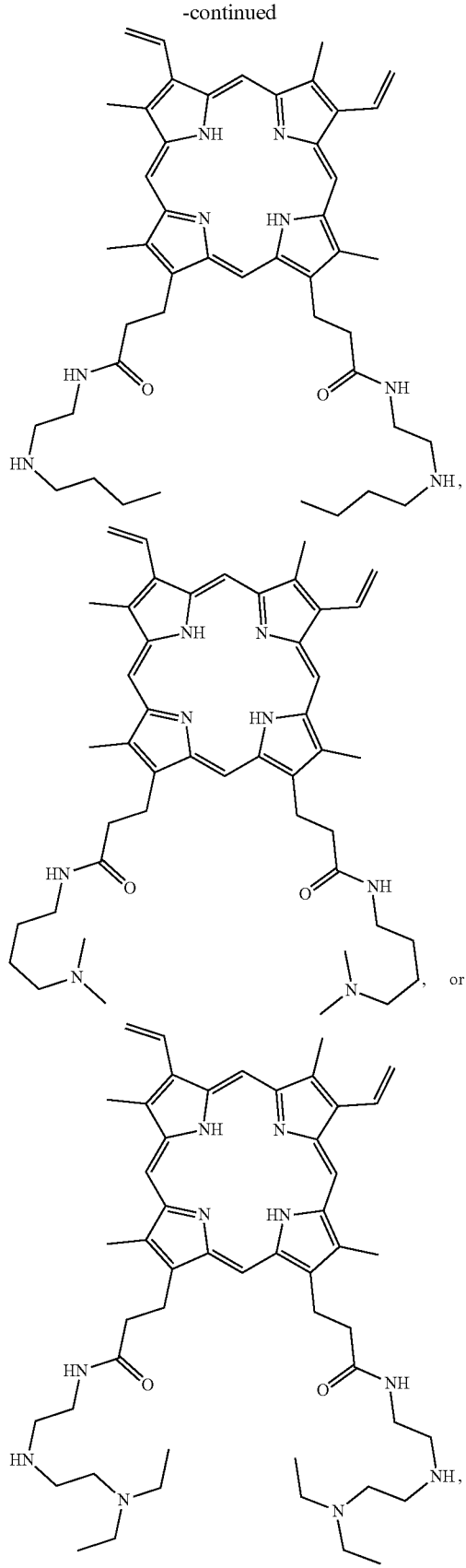
or an agriculturally acceptable salt thereof.
In some implementations, the compound of Formula I-B1 is:
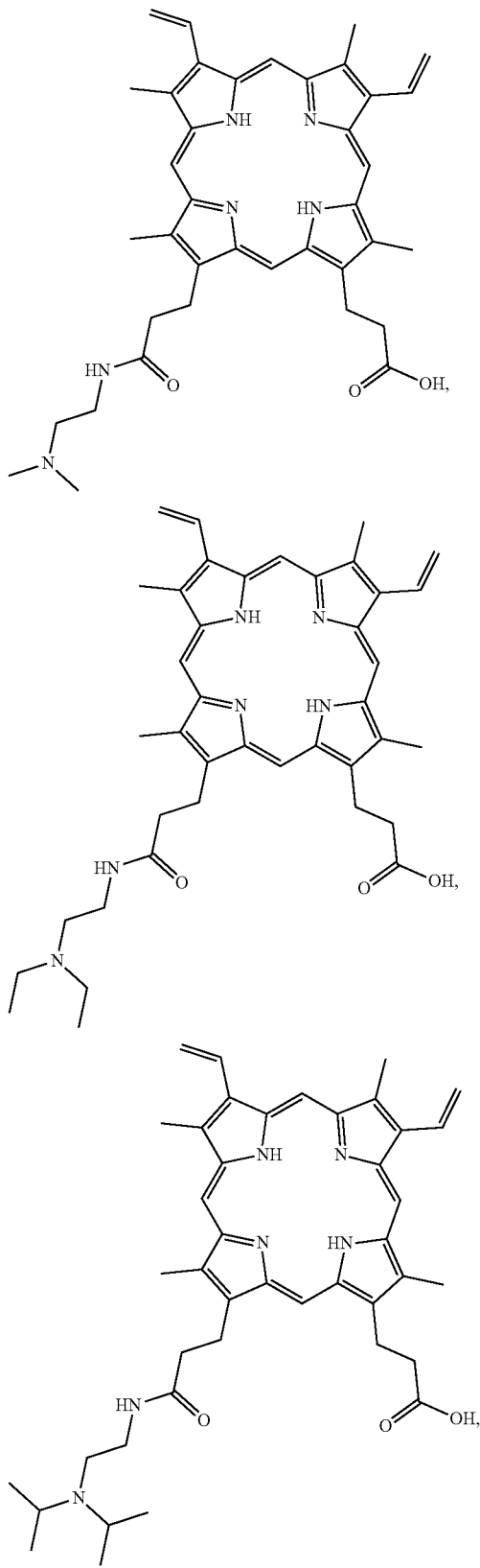

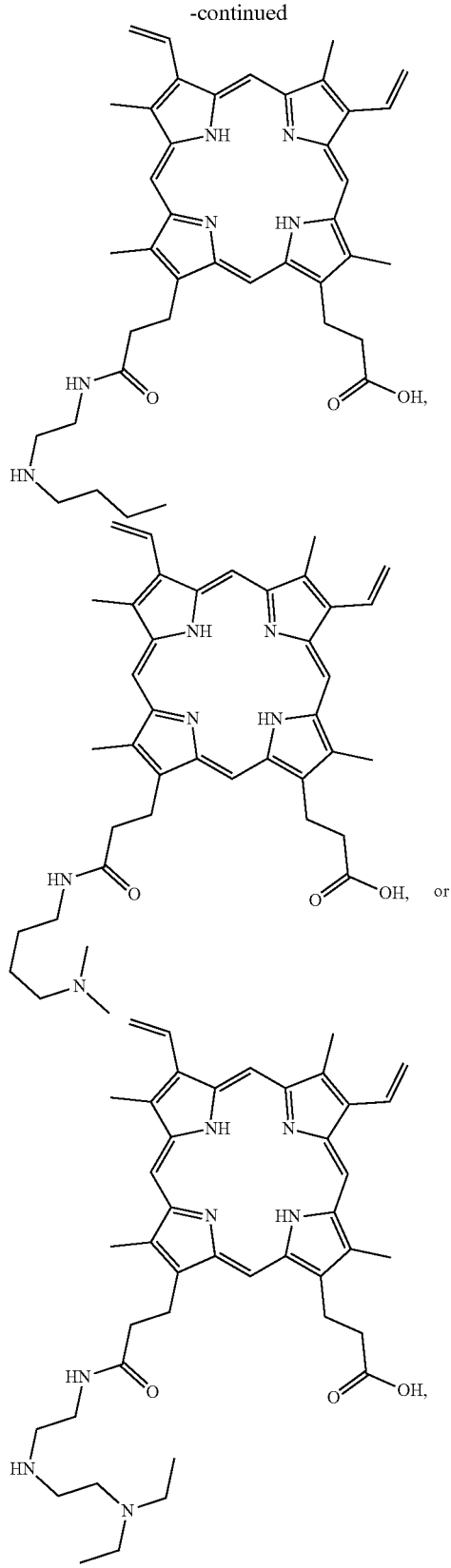
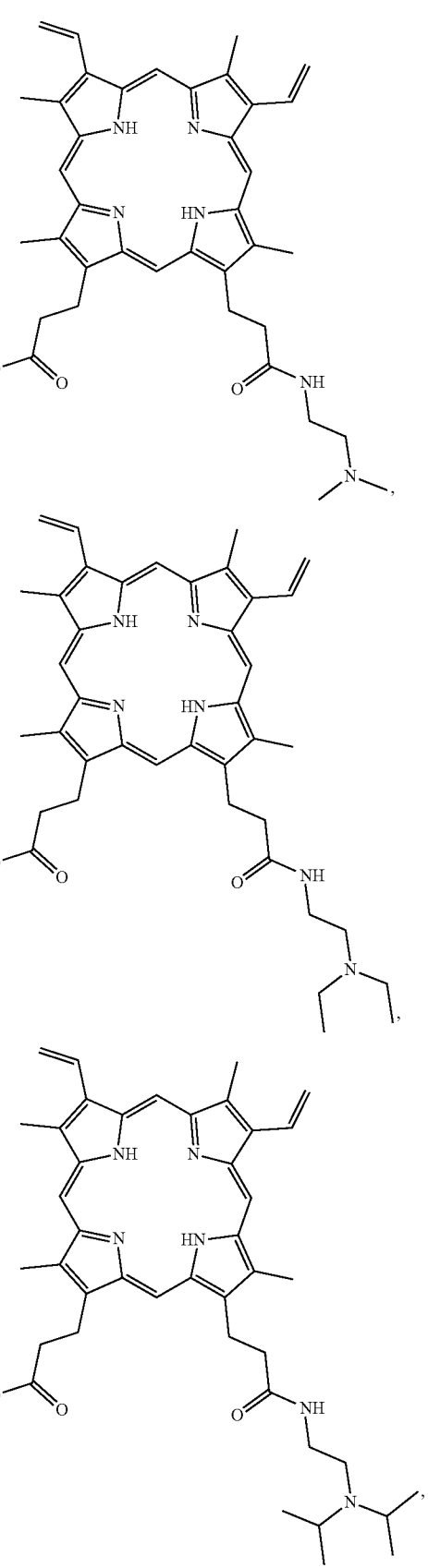
or an agriculturally acceptable salt thereof.
In some implementations, the compound of Formula I-B1 is:

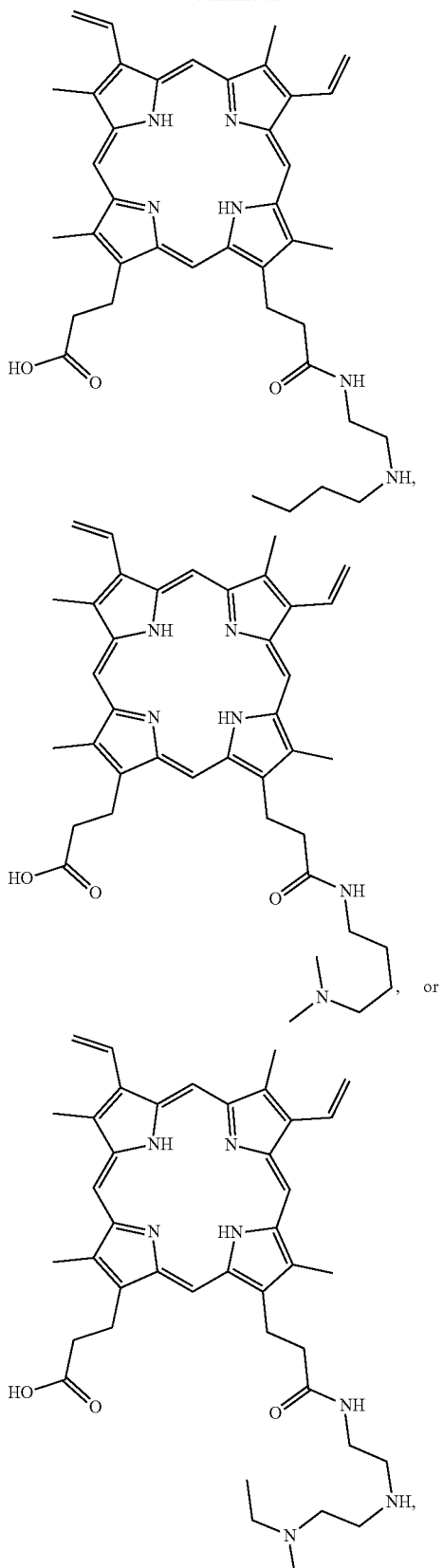

or an agriculturally acceptable salt thereof.

In another aspect, there is provided a compound of Formula I-B1:

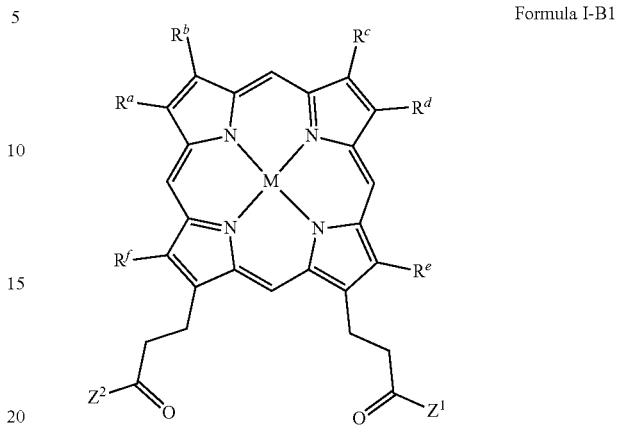

Formula I-B1 or an agriculturally acceptable salt thereof, for use in promoting the health of a plant, wherein:
one of $Z^1$ and $Z^2$ is $NR^2-(CH_2)_n-Si(R^7)_3$, $O-(CH_2)_n-Si(R^7)_3$, $NR^2-(CH_2)_n-SR^8$ or $O-(CH_2)_n-SR^8$; and
the other one of $Z^1$ and $Z^2$ is $OR^1$;
or
$Z^1=NR^2-(CH_2)_n-Si(R^7)_3$, $O-(CH_2)_n-Si(R^7)_3$, $NR^2-(CH_2)_n-SR^8$ or $O-(CH_2)_n-SR^8$; and
$Z^2=Z^1$;
each $R^1$ and $R^2$ is, independently, H, alkyl or substituted alkyl;
$R^7$ is alkyl, O(alkyl) or O(trisubstituted silyl);
$R^8$ is H, alkyl, substituted alkyl or $-(CH_2)_q-(CH_2CH_2O)_m-R^{13}$;
$R^{13}$ is H, alkyl, substituted alkyl, alkenyl, substituted alkenyl, alkynyl, substituted alkynyl, CO(alkyl), CO(substituted alkyl), CO(alkenyl), CO(substituted alkenyl), CO(alkynyl) or CO(substituted alkynyl);
n is an integer selected from 1 to 16;
m is an integer selected from 1 to 100;
q is an integer selected from 0 to 16;
each $R^a$, $R^b$, $R^c$, $R^d$, $R^e$ and $R^f$ is, independently, H, alkyl, substituted alkyl, alkenyl, substituted alkenyl, alkynyl or substituted alkynyl; and
M is 2H or a metal species,
wherein the substituted alkyl, substituted alkenyl and substituted alkynyl groups are, independently, substituted with one or more OH, F, Cl, Br, I, CN and $N_3$.

In some implementations, $R^1$ is H and/or $R^2$ is H. In some implementations, $R^7$ is alkyl, O(alkyl) or O(tri-substituted silyl). The alkyl groups for $R^1$, $R^2$ and $R^7$ can each independently be a $(C_1-C_{12})$alkyl, a $(C_1-C_8)$alkyl or a $(C_1-C_4)$ alkyl. In some implementations, $R^8$ is $-(CH_2)_q-(CH_2CH_2O)_m-R^{13}$. $R^{13}$ can be H and m can be an integer selected from 1 to 20. In some implementations, n is an integer selected from 1 to 16, or from 1 to 12, or from 1 to 8, or from 1 to 6, or from 1 to 4, or from 2 to 4. In some implementations, q is an integer selected from 0 to 16, or from 1 to 8, or from 0 to 4, or from 0 to 2. In some implementations, q=1. In other implementations, q=0.

In some implementations, one of $Z^1$ and $Z^2$ is $NR^2-(CH_2)_n-Si(R^7)_3$, $O-(CH_2)_n-Si(R^7)_3$, $NR^2-(CH_2)_n-SR^8$ or $O-(CH_2)_n-SR^8$; and the other one of $Z^1$ and $Z^2$ is $OR^1$. In other implementations, $Z^1=NR^2-(CH_2)_n-Si(R^7)_3$, $O-(CH_2)_n-Si(R^7)_3$, $NR^2-(CH_2)_n-SR^8$ or $O-(CH_2)_n-SR^8$; and $Z^2=Z^1$.

In some implementations, the compound of Formula I-B1 is:
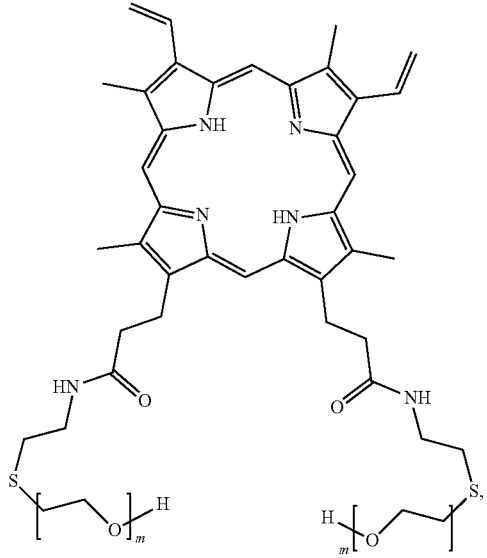
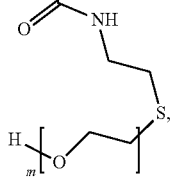
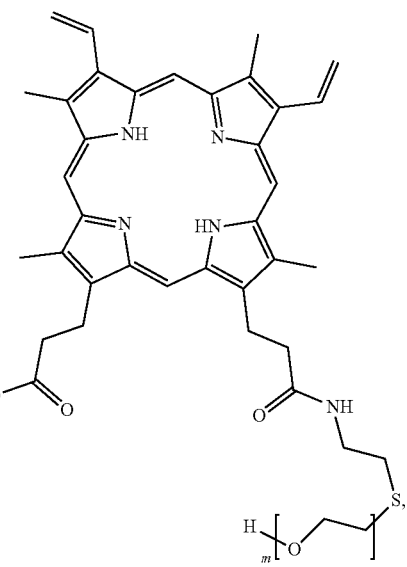
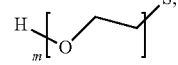
or an agriculturally acceptable salt thereof,
wherein m is an integer selected from 4 to 15.
In some implementations, the compound of Formula I-B1 is:
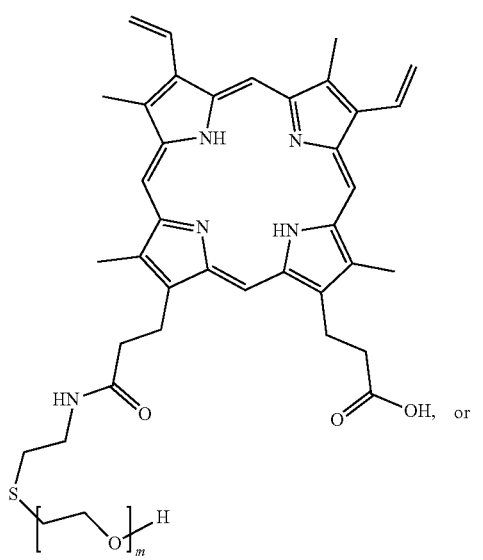
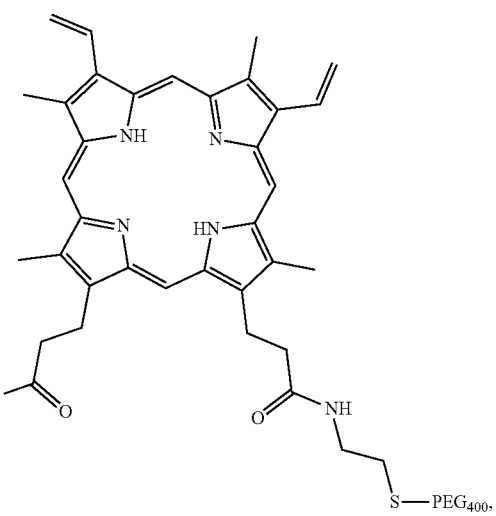

or an agriculturally acceptable salt thereof.
In some implementations, the compound of Formula I-B1 is:
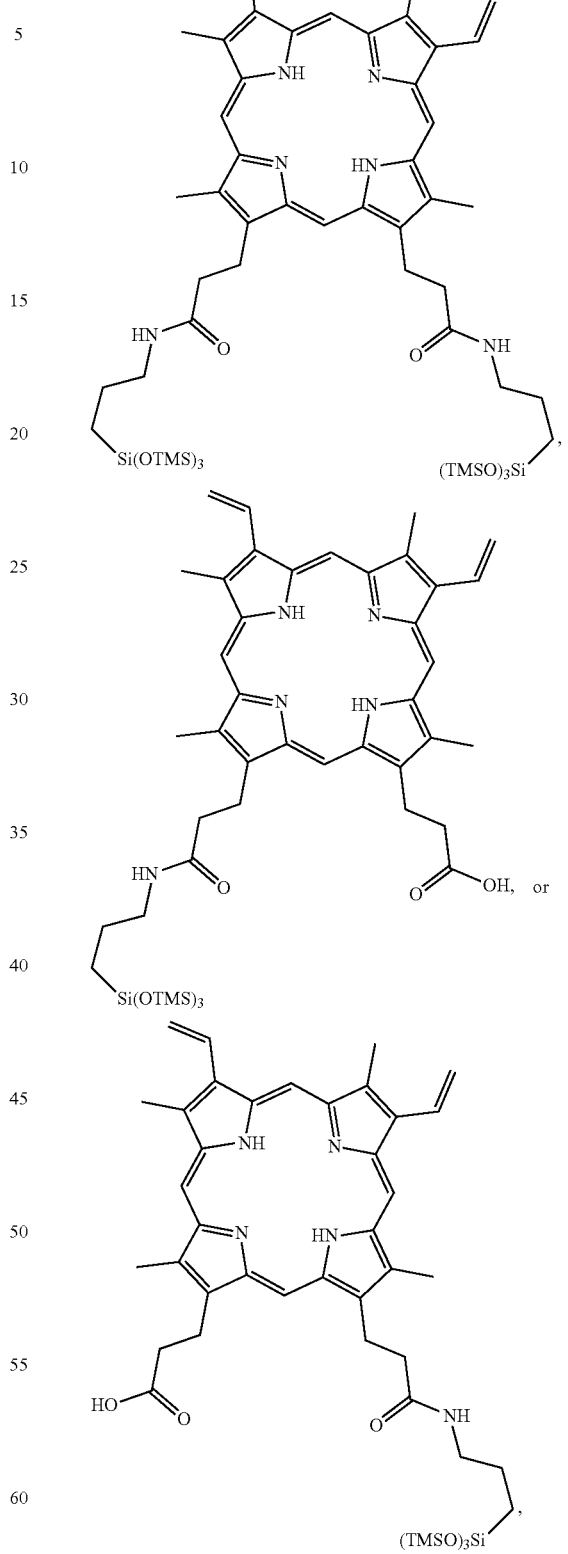
or an agriculturally acceptable salt thereof.
In another aspect, there is provided a compound of Formula I-B1:

Formula I-B1

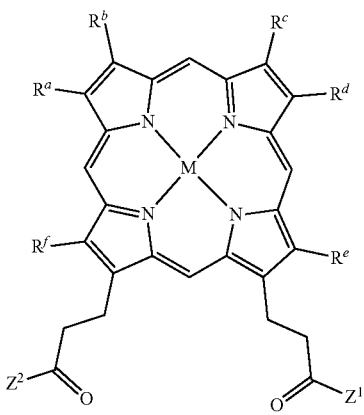

or an agriculturally acceptable salt thereof, for use in promoting the health of a plant, wherein:

one of $Z^1$ and $Z^2$ is $NR_2$—$(CH_2)_n$—$OP$=$O(OH)_2$ or $O$—$(CH_2)_n$—$OP$=$O(OH)_2$, $NR_2$—$(CH_2)_n$—$OP$=$O(OH)O^-$ $W^+$ or $O$—$(CH_2)_n$—$OP$=$O(OH)O^-$ $W^+$; and the other one of $Z^1$ and $Z^2$ is $OR^1$;

or $Z^1$=$NR_2$—$(CH_2)_n$—$OP$=$O(OH)_2$ or $O$—$(CH_2)_n$—$OP$=$O(OH)_2$, $NR_2$—$(CH_2)_n$—$OP$=$O(OH)O^-$ $W^+$ or $O$—$(CH_2)_n$—$OP$=$O(OH)O^-$ $W^+$; and $Z^2$=$Z^1$;

each $R^1$ and $R^2$ is, independently, H, alkyl or substituted alkyl;

n is an integer selected from 1 to 16;

$W^+$ is an agriculturally acceptable cation;

each $R^a$, $R^b$, $R^c$, $R^d$, $R^e$ and $R^f$ is, independently, H, alkyl, substituted alkyl, alkenyl, substituted alkenyl, alkynyl or substituted alkynyl; and M is 2H or a metal species, wherein the substituted alkyl, substituted alkenyl and substituted alkynyl groups are, independently, substituted with one or more OH, F, Cl, Br, I, CN and $N_3$.

In some implementations, $R^1$ is H and/or $R^2$ is H. In some implementations, n is an integer selected from 1 to 16, or from 1 to 12, or from 1 to 8, or from 1 to 6, or from 1 to 4, or from 2 to 4. $W^+$ can be selected from the group consisting of sodium, potassium, magnesium and ammonium cations.

In some implementations, one of $Z^1$ and $Z^2$ is $NR_2$—$(CH_2)_n$—$OP$=$O(OH)_2$ or $O$—$(CH_2)_n$—$OP$=$O(OH)_2$, $NR_2$—$(CH_2)_n$—$OP$=$O(OH)O^-$ $W^+$ or $O$—$(CH_2)_n$—$OP$=$O(OH)O^-$ $W^+$; and the other one of $Z^1$ and $Z^2$ is $OR^1$. In other implementations, $Z^1$=$NR_2$—$(CH_2)_n$—$OP$=$O(OH)_2$ or $O$—$(CH_2)_n$—$OP$=$O(OH)_2$, $NR_2$—$(CH_2)_n$—$OP$=$O(OH)O^-$ $W^+$ or $O$—$(CH_2)_n$—$OP$=$O(OH)O^-$ $W^+$; and $Z^2$=$Z^1$.

In some implementations, the compound of Formula I-B1 is:

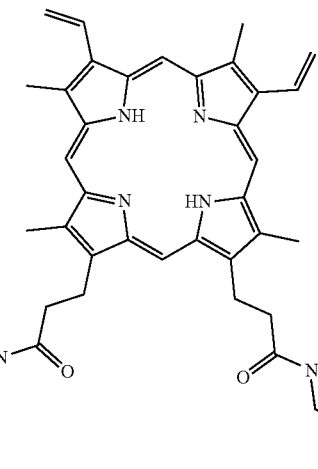

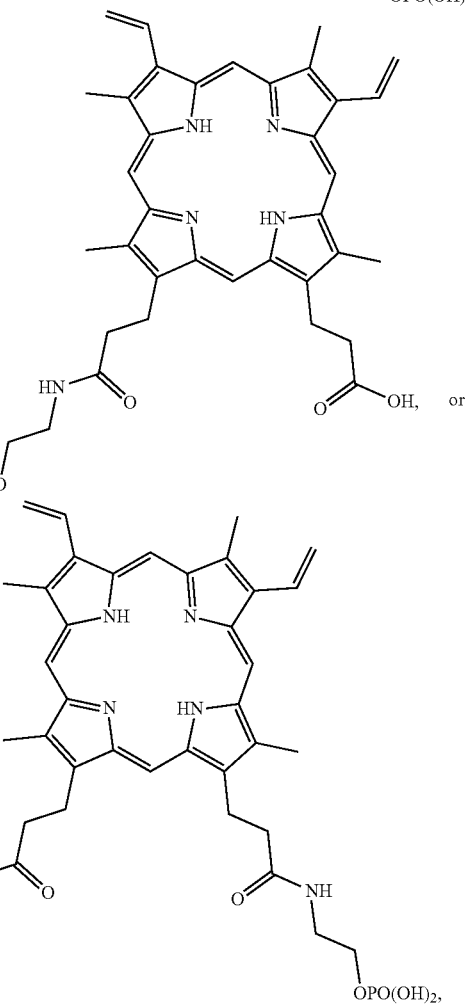

or an agriculturally acceptable salt thereof.

In some implementations, the compound of Formula I-B1 is:

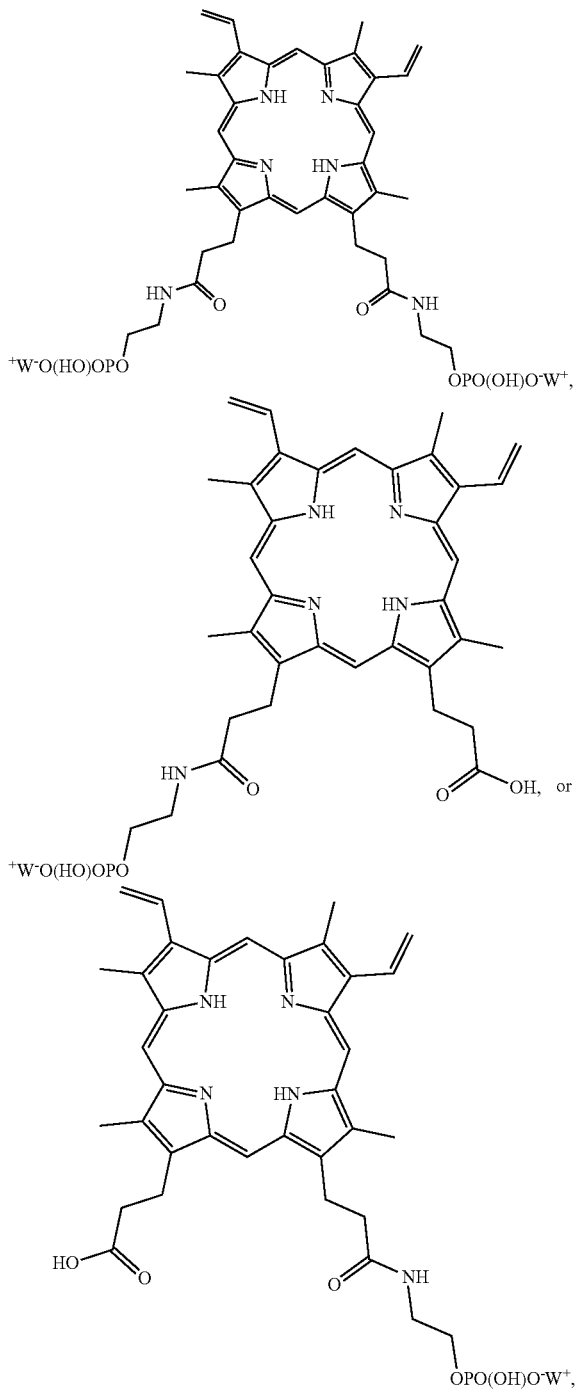

or an agriculturally acceptable salt thereof, wherein W+ is a cation that can be selected from the group consisting of: of sodium, potassium, magnesium, ammonium and alkylammonium cations. For example, W+ can be an n-octylammonium cation.

In another aspect, there is provided a compound of Formula I-B1:

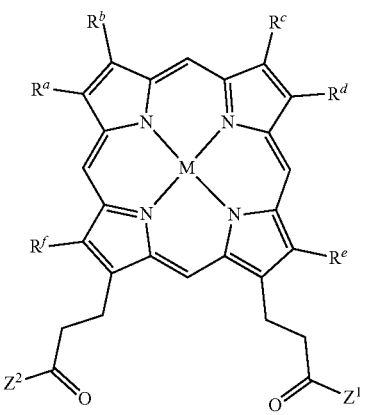

Formula I-B1 or an agriculturally acceptable salt thereof, for use in promoting the health of a plant, wherein:

one of $Z^1$ and $Z^2$ is $NR^2—(CH_2)_n—NR^4R^5R^{6+}$ $Y^-$ or $O—(CH_2)_n—NR^4R^5R^{6+}$ $Y^-$; and the other one of $Z^1$ and $Z^2$ is $OR^1$;

or $Z^1=NR^2—(CH_2)_n—NR^4R^5R^{6+}$ $Y^-$ or $O—(CH_2)_n—NR^4R^5R^{6+}$ $Y^-$; and $Z^2=Z^1$;

each $R^1$ and $R^2$ is, independently, H, alkyl or substituted alkyl;

each $R^4$, $R^5$ and $R^6$ is, independently, alkyl or substituted alkyl;

n is an integer selected from 1 to 16;

$Y^-$ is an agriculturally acceptable anion;

each $R^a$, $R^b$, $R^c$, $R^d$, $R^e$ and $R^f$ is, independently, H, alkyl, substituted alkyl, alkenyl, substituted alkenyl, alkynyl or substituted alkynyl; and M is 2H or a metal species, wherein the substituted alkyl, substituted alkenyl and substituted alkynyl groups are, independently, substituted with one or more OH, F, Cl, Br, I, CN and $N_3$.

In some implementations, $R^1$ is H and/or $R^2$ is H. In some implementations, n is an integer selected from 1 to 16, or from 1 to 12, or from 1 to 8, or from 1 to 6, or from 1 to 4, or from 2 to 4. In some implementations, $R^4$, $R^5$ and $R^6$ are alkyl and optionally $R^4=R^5=R^6$. In some implementations, $Y^-$ is selected from the group consisting of chloride, bromide, phosphate, dimethylphosphate, methylsulfate, ethylsulfate, acetate and lactate.

In some implementations, one of $Z^1$ and $Z^2$ is $NR^2—(CH_2)_n—NR^4R^5R^{6+}$ $Y^-$ or $O—(CH_2)_n—NR^4R^5R^{6+}$ $Y^-$; and the other one of $Z^1$ and $Z^2$ is $OR^1$. In other implementations, $Z^1=NR^2—(CH_2)_n—NR^4R^5R^{6+}$ $Y^-$ or $O—(CH_2)_n—NR^4R^5R^{6+}$ $Y^-$; and $Z^2=Z^1$.

In some implementations, the compound of Formula I-B1 is:

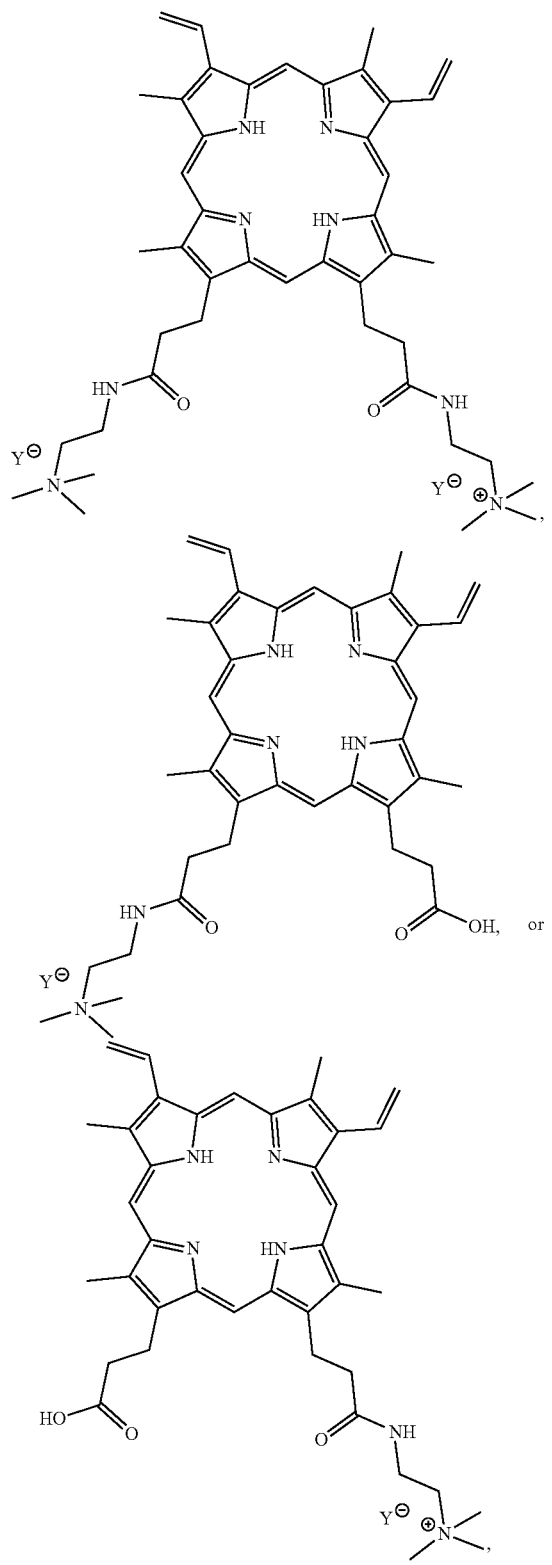

wherein Y⁻ is an agriculturally acceptable anion that can be selected from the group consisting of: chloride, bromide, phosphate, dimethylphosphate, methylsulfate, ethylsulfate, acetate, citrate, tartrate and lactate.

In another aspect, there is provided a compound of Formula I-B1:

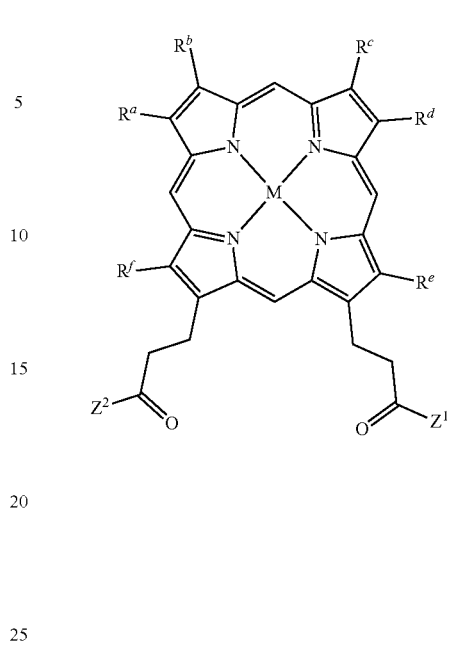

Formula I-B1 or an agriculturally acceptable salt thereof, for use in promoting the health of a plant, wherein:

one of $Z^1$ and $Z^2$ is $NR^2—(CH_2CH_2O)_m—R^{13}$ or $O—(CH_2CH_2O)_m—R^{13}$; and the other one of $Z^1$ and $Z^2$ is $OR^1$;

or $Z^1=NR^2—(CH_2CH_2O)_m—R^{13}$ or $O—(CH_2CH_2O)_m—R^{13}$; and $Z^2=Z^1$;

each $R^1$ and $R^2$ is, independently, H, alkyl or substituted alkyl;

$R^{13}$ is H, alkyl, substituted alkyl, alkenyl, substituted alkenyl, alkynyl, substituted alkynyl, CO(alkyl), CO(substituted alkyl), CO(alkenyl), CO(substituted alkenyl), CO(alkynyl) or CO(substituted alkynyl);

m is an integer selected from 1 to 100;

each $R^a$, $R^b$, $R^c$, $R^d$, $R^e$ and $R^f$ is, independently, H, alkyl, substituted alkyl, alkenyl, substituted alkenyl, alkynyl or substituted alkynyl; and M is 2H or a metal species, wherein the substituted alkyl, substituted alkenyl and substituted alkynyl groups are, independently, substituted with one or more OH, F, Cl, Br, I, CN and $N_3$.

In some implementations, $R^1$ is H and/or $R^{12}$ is H. In some implementations, m is an integer selected from 5 to 100, or from 5 to 80, or from 5 to 50, or from 5 to 20, or from 5 to 10. In some implementations, $R^{13}$ is H, alkyl, alkenyl, CO(alkyl) or CO(alkenyl).

In some implementations, one of $Z^1$ and $Z^2$ is $NR^2—(CH_2CH_2O)_m—R^{13}$ or $O—(CH_2CH_2O)_m—R^{13}$; and the other one of $Z^1$ and $Z^2$ is $OR^1$. In other implementations, $Z^1=NR^2—(CH_2CH_2O)_m—R^{13}$ or $O—(CH_2CH_2O)_m—R^{13}$; and $Z^2=Z^1$.

In some implementations, the compound of Formula I-B1 is:

51
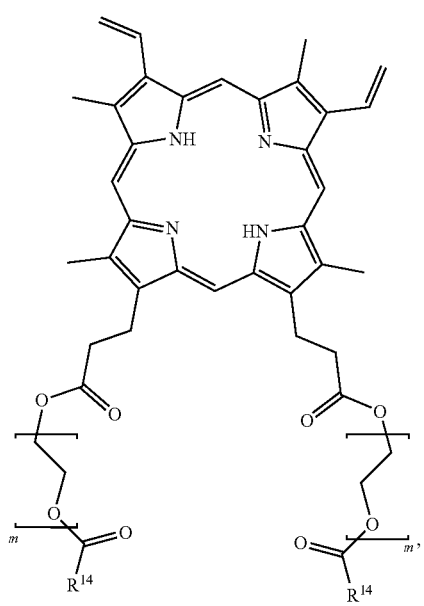
52
-continued
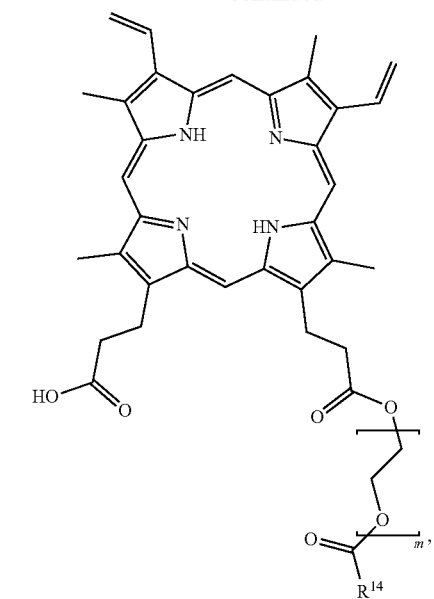
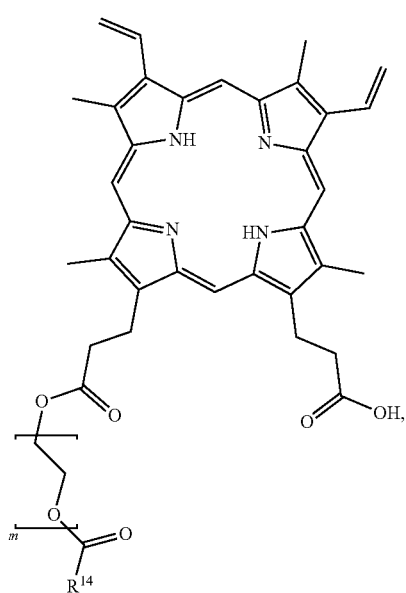
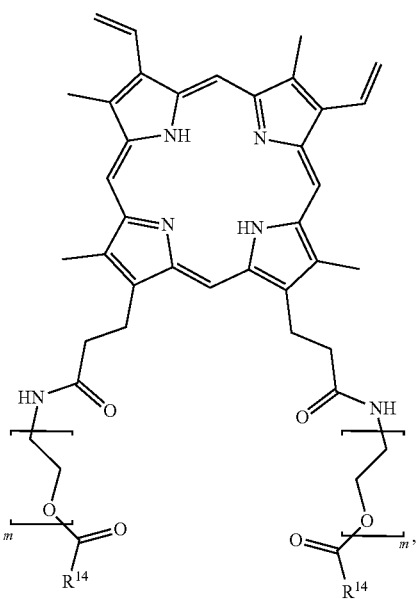

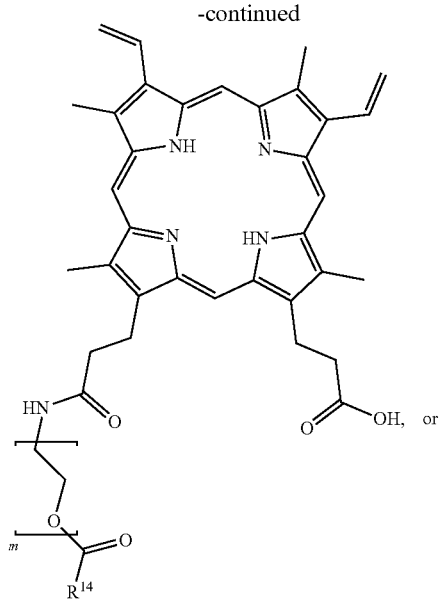

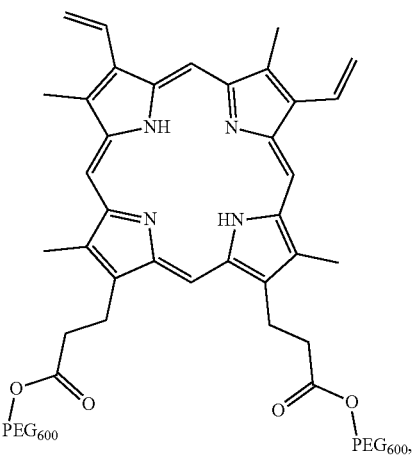

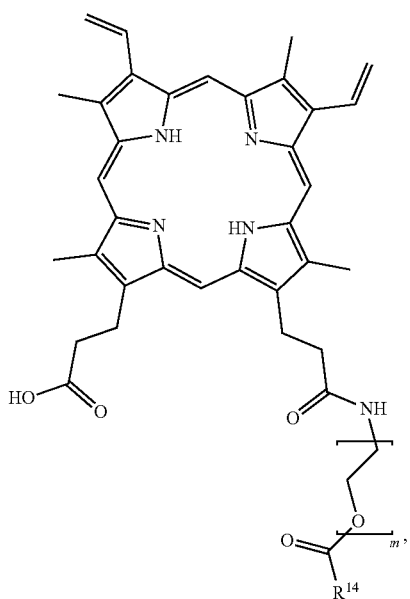

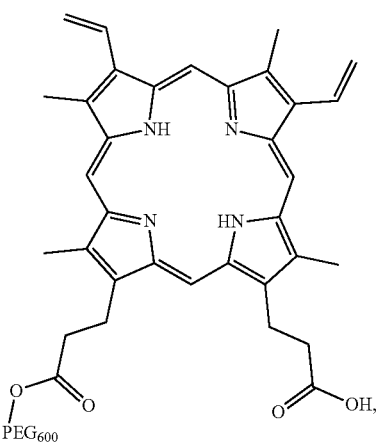

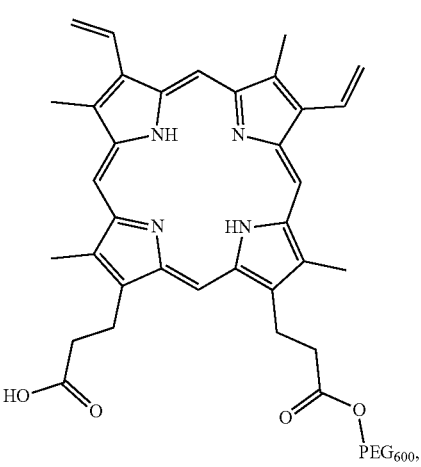

or an agriculturally acceptable salt thereof, wherein m is an integer selected from 1 to 100; and $R^{14}$ is alkyl, alkenyl, alkynyl, substituted alkyl, substituted alkenyl or substituted alkynyl.

In some implementations, m is an integer selected from 5 to 20 and $(CH_2CH_2O)_m COR^{14}$ is $PEG_{600}$-oleate, $PEG_{400}$-oleate, $PEG_{600}$-allyl or $PEG_{400}$-allyl.

In some implementations, $R^{13}$ is H. In some implementations, $(CH_2CH_2O)_m R^{13}$ is $PEG_{600}$ or $PEG_{400}$.

In some implementations, the compound of Formula I-B1 is:

-continued

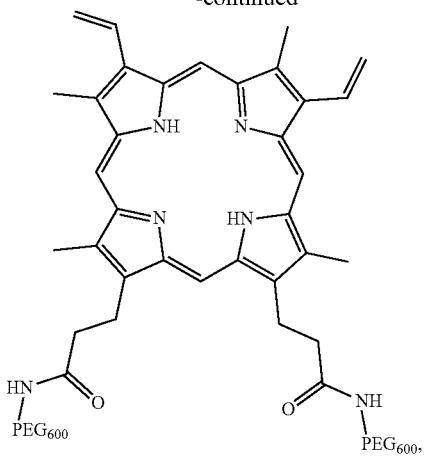

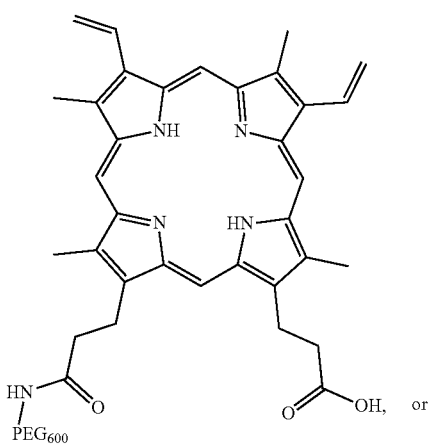

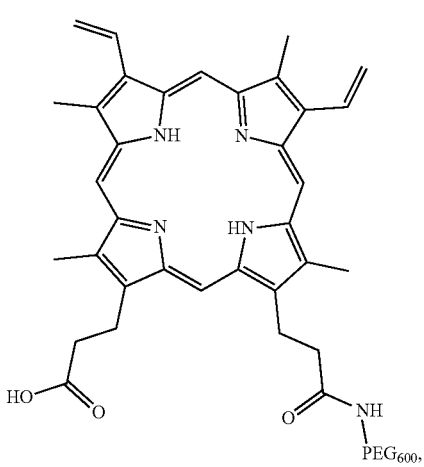

or an agriculturally acceptable salt thereof.

In yet another aspect of the present description, a compound of Formula I-B1 is provided:

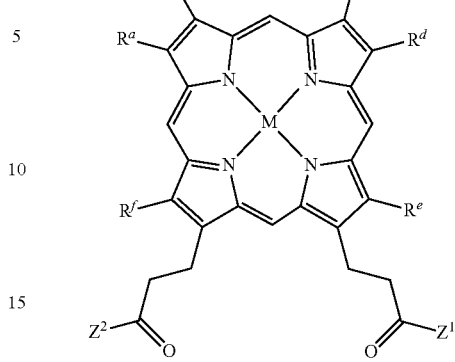

Formula I-B1 or an agriculturally acceptable salt thereof, for use in promoting the health of a plant, wherein:

one of $Z^1$ and $Z^2$ is a natural amino acid attached to the compound by its amino group bonded to the alpha carbon; and the other one of $Z^1$ and $Z^2$ is $OR^1$;

or $Z^1$ is a natural amino acid attached to the compound by its amino group bonded to the alpha carbon; and $Z^2=Z^1$;

each $R^1$ and $R^2$ is, independently, H, alkyl or substituted alkyl;

each $R^a$, $R^b$, $R^c$, $R^d$, $R^e$ and $R^f$ is, independently, H, alkyl, substituted alkyl, alkenyl, substituted alkenyl, alkynyl or substituted alkynyl; and M is 2H or a metal species, wherein the substituted alkyl, substituted alkenyl and substituted alkynyl groups are, independently, substituted with one or more OH, F, Cl, Br, I, CN and $N_3$.

In some implementations, one of $Z^1$ and $Z^2$ is a natural amino acid attached to the compound by its amino group bonded to the alpha carbon; and the other one of $Z^1$ and $Z^2$ is $OR^1$.

In other implementations, $Z^1$ is a natural amino acid attached to the compound by its amino group bonded to the alpha carbon; and $Z^2=Z^1$.

In some implementations, $Z^1$ is one of the natural amino acids and $Z^2$ is OH; $Z^2$ is one of the natural amino acids and $Z^1$ is OH; or $Z^1$ is one of the natural amino acids and $Z^2=Z^1$.

In some implementations, $Z^1$ is Glycine, L-Alanine or L-Valine and $Z^2$ is OH; $Z^2$ is Glycine, L-Alanine or L-Valine and $Z^1$ is OH; or $Z^1$ is Glycine, L-Alanine or L-Valine and $Z^2=Z^1$.

In some implementations, the compound of Formula I-B1 is:

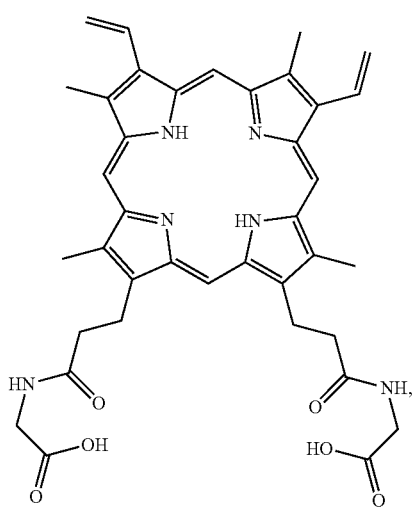
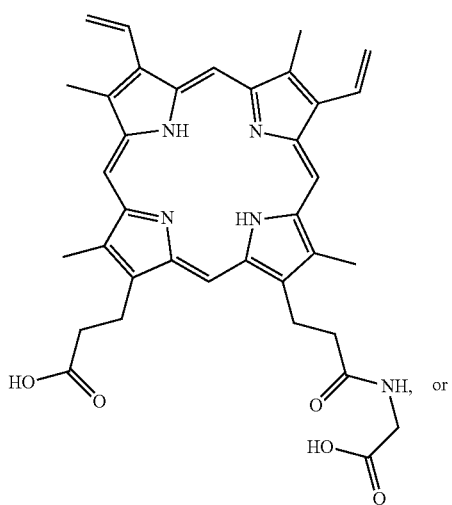
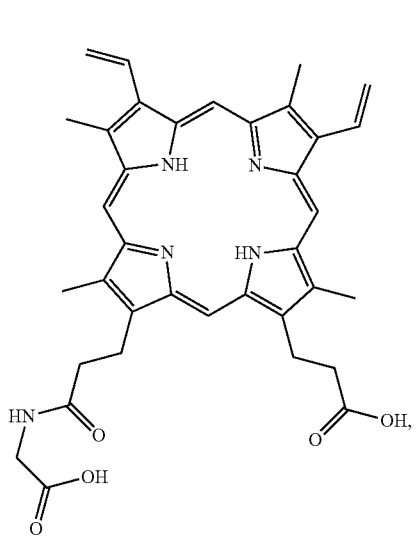
or an agriculturally acceptable salt thereof.
In some implementations, the compound of Formula I-B1 is:
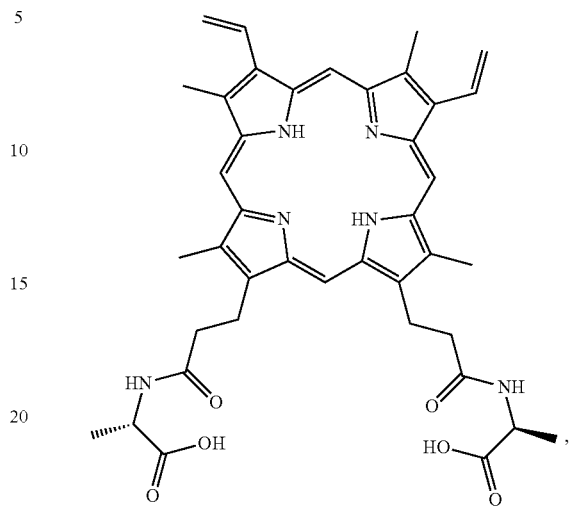
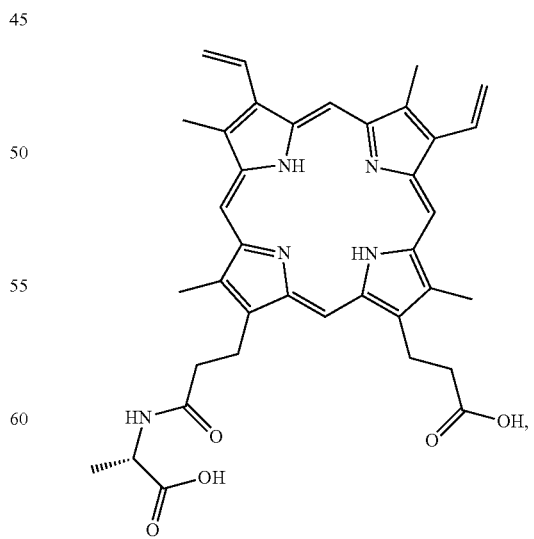
or an agriculturally acceptable salt thereof.

In some implementations, the compound of Formula I-B1 is:

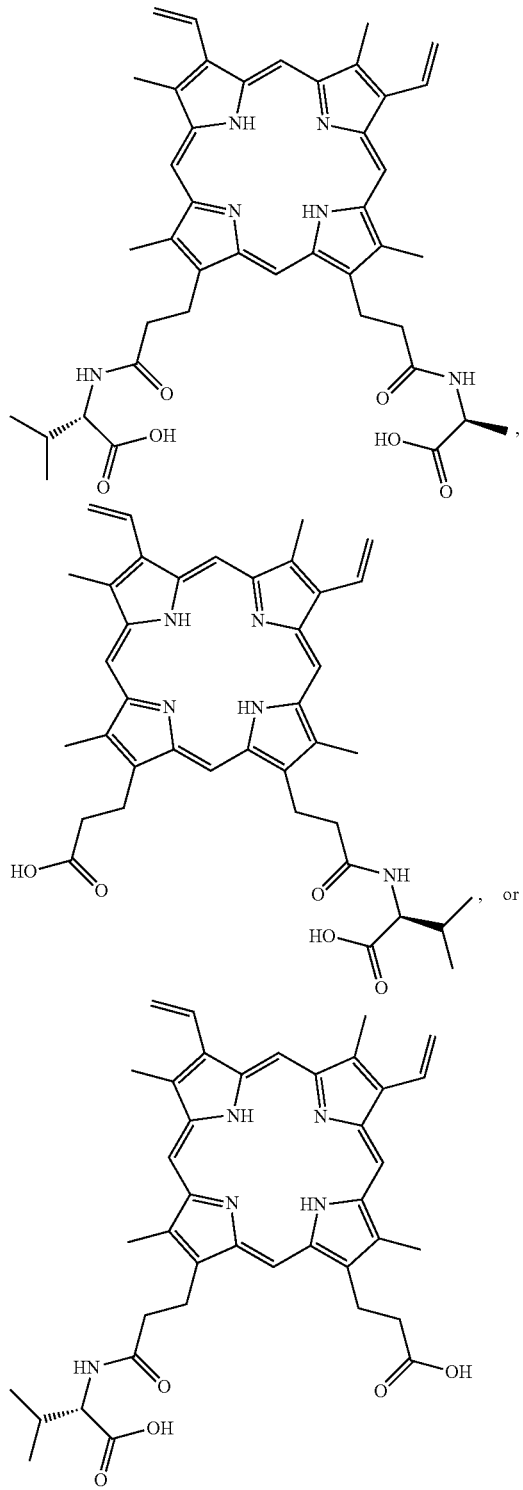

or an agriculturally acceptable salt thereof.
In some implementations, the compound of Formula I-B1 is:

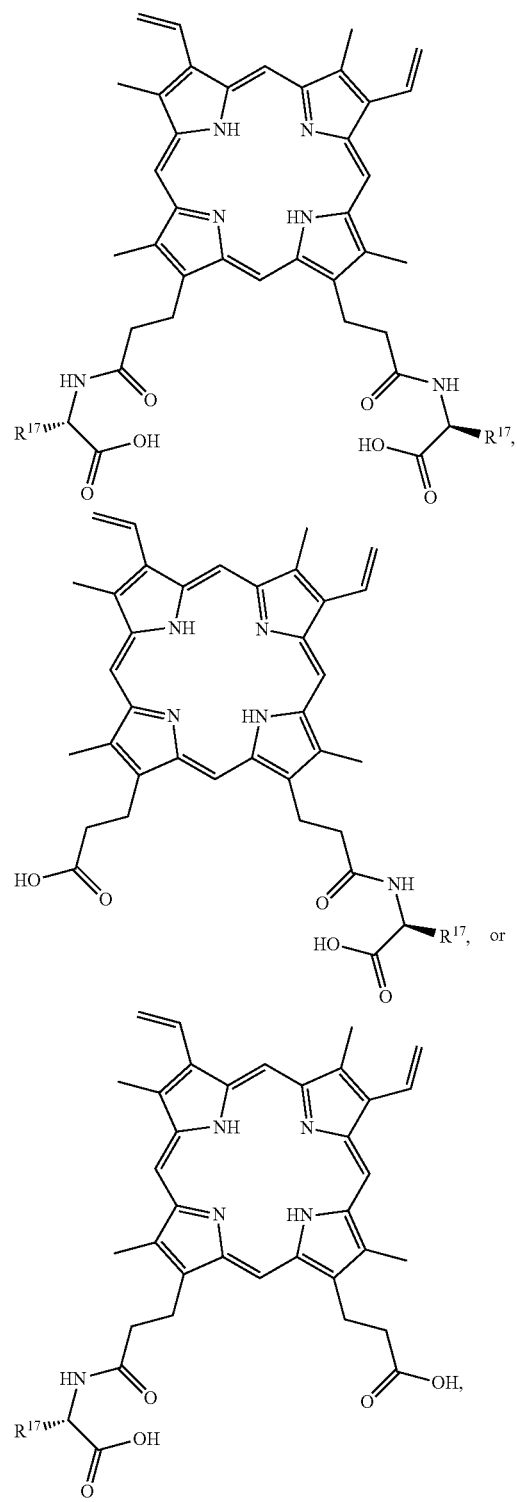

or an agriculturally acceptable salt thereof, wherein $R^{17}$ is the side chain of one of the twenty natural amino acids.

Synthesis of the Photosensitizer Compounds

In another aspect, there is provided a method of manufacture of the compounds described herein, comprising reacting one of the compounds of Formula II, or a salt thereof, with a corresponding amine or an alcohol.

For example, a compound of Formula II can first be reacted with a coupling agent (e.g., DCC, EDC etc.) before being reacted with an amine, as shown in the scheme below, to give a mixture of mono and bis substituted amide compounds.

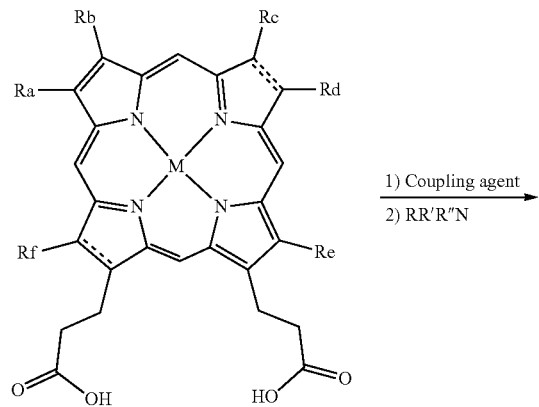

1) Coupling agent
2) RR'R"N →

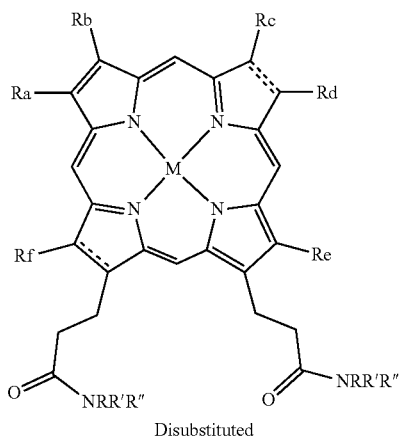

Disubstituted

In another example, the compound of Formula II can be esterified using esterification methods known in the art.

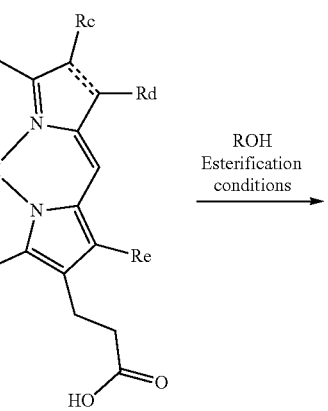

ROH
Esterification
conditions
→

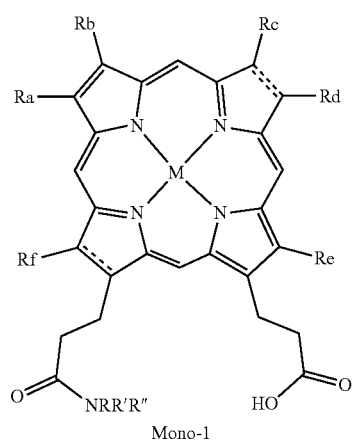

Mono-1

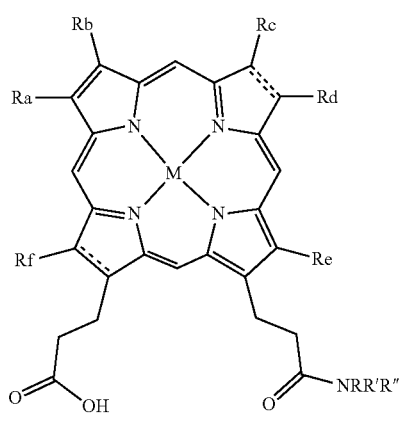

Mono-2

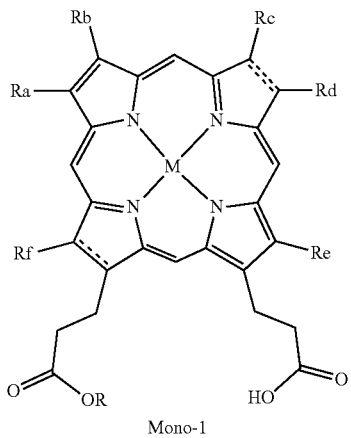

Mono-1

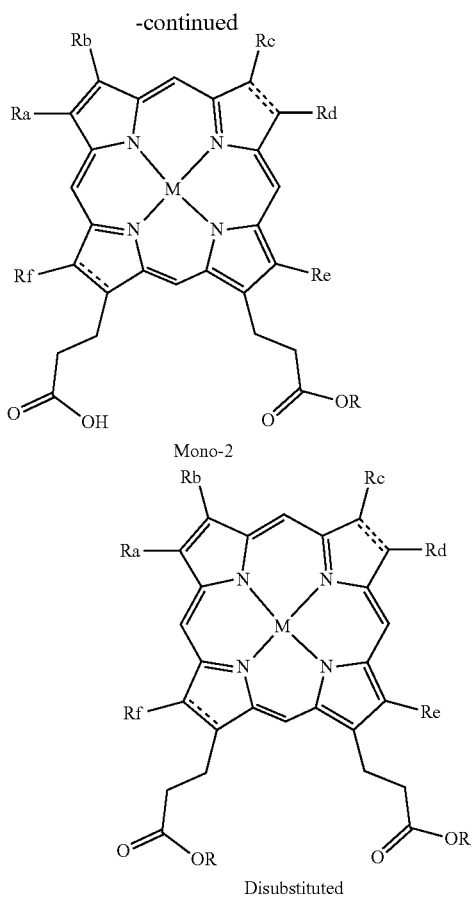

Mono-2

Disubstituted

Examples of such reactions can be found in the Examples section.

Chelating Agent

In some implementations, the photosensitizer compound can be applied to a plant in combination with a chelating agent (also referred to herein as a permeabilizing agent). In some scenarios, the photosensitizer compound reacts to light by generating ROS, while the chelating agent can increase the overall impact of suppression of the growth of the microbial pathogen, for example by increasing the permeability of the outer membrane of the microbial pathogen to the photosensitizer. It should be understood that the term "chelating agent", as used herein, refers generally to a compound that can form several chelating bonds to one or several metals or ions.

In some implementations, the chelating agent can include at least one carboxylic group, at least one hydroxyl group, at least one phenol group and/or at least one amino group or an agriculturally acceptable salt thereof. In some implementations, the chelating agent can include an aminocarboxylic acid compound or an agriculturally acceptable salt thereof. The aminocarboxylic acid or agriculturally acceptable salt thereof can include an amino polycarboxylic acid or an agriculturally acceptable salt thereof. For example, the amino polycarboxylic acid can include two amino groups and two alkylcarboxyl groups bound to each amino group. The alkylcarboxyl groups can be methylcarboxyl groups.

In some implementations, the chelating agent is selected from the group consisting of: an aminopolycarboxylic acid, an aromatic or aliphatic carboxylic acid, an amino acid, a phosphonic acid, and a hydroxycarboxylic acid or an agriculturally acceptable salt thereof.

In some implementations, the methods and compositions described herein include one or more aminopolycarboxylic acid chelating agents. Examples of aminopolycarboxylic acid chelating agents include, without limitation, ethylenediaminetetraacetic acid (EDTA), diethylenetriaminepentaacetic acid (DTPA), hydroxyethylenediaminetriacetic acid (HEDTA), and ethylenediaminedisuccinate (EDDS), cyclohexanediaminetetraacetic acid (CDTA), N-(2-hydroxyethyl) ethylenediaminetriacetic acid (EDTA-OH) glycol ether diaminetetraacetic acid (GEDTA), alanine diacetic acid (ADA), alkoyl ethylene diamine triacetic acids (e.g., lauroyl ethylene diamine triacetic acids (LED3A)), aspartic acid diacetic acid (ASDA), aspartic acid monoacetic acid, diamino cyclohexane tetraacetic acid (CDTA), 1,2-diaminopropanetetraacetic acid (DPTA-OH), 1,3-diamino-2-propanoltetraacetic acid (DTPA), diethylene triamine pentam ethylene phosphonic acid (DTPMP), diglycolic acid, dipicolinic acid (DPA), ethanolamine diacetic acid, ethanol diglycine (EDG), ethylenediaminediglutaric acid (EDDG), ethylenediaminedi(hydroxyphenylacetic acid (EDDHA), ethylenediaminedipropionic acid (EDDP), ethylenediaminedisuccinate (EDDS), ethylenediaminemonosuccinic acid (EDMS), ethylenediaminetetraacetic acid (EDTA), ethylenediaminetetrapropionic acid (EDTP), and ethyleneglycolaminoethylestertetraacetic acid (EGTA) and agriculturally acceptable salts (for example, the sodium salts, calcium salts and/or potassium salts) thereof.

One non-limiting example of chelating agent is ethylenediaminetetraacetic acid (EDTA) or an agriculturally acceptable salt thereof. The aminocarboxylate salt can for example be a sodium or calcium salt.

Another non-limiting example of chelating agent is polyaspartic acid or an agriculturally acceptable salt thereof (i.e., a polyaspartate), such as sodium polyaspartate. The molecular weight of the polyaspartate salt can for example be between 2,000 and 3,000.

The chelating agent can thus be a polymeric compound, which can include aspartate units, carboxylic groups, and other features found in polyaspartates. The polyaspartate can be a co-polymer that has alpha and beta linkages, which may be in various proportions (e.g., 30% alpha, 70% beta, randomly distributed along the polymer chain). One non-limiting example of a sodium polyaspartate is Baypure® DS 100.

Other non-limiting examples of chelating agents include EDDS (ethylenediamine-N,N'-disuccinic acid), IDS (iminodisuccinic acid (N-1,2-dicarboxyethyl)-D,L-aspartic acid), isopropylamine, triethanolamine, triethylamine, ammonium hydroxide, tetrabutylammonium hydroxide, hexamine, GLDA (L-glutamic acid N,N-diacetic acid), or agriculturally acceptable salts thereof. The chelating agent can be metallated or non-metallated. In some implementations, IDS can be used as a tetrasodium salt of IDS (e.g., tetrasodium iminodisuccinate), which can be Baypure® CX100. In some implementations, EDDS can be used as a trisodium salt of EDDS. In some implementations, GLDA can be used as a tetrasodium salt of GLDA.

In some implementations, the chelating agent can include one or more amino acid chelating agents. Examples of amino acid chelating agents include, without limitation, alanine, arginine, asparagine, aspartic acid, glutamic acid, glutamine, glycine, histidine, isoleucine, leucine, lysine, methionine, proline, serine, threonine, tyrosine, valine, or salts (for example, the sodium salts, calcium salts and/or potassium salts) and combinations thereof.

In some implementations, the chelating agent can include one or more aromatic or aliphatic carboxylic acid chelating agents. Examples of aromatic or aliphatic carboxylic acid chelating agents include, without limitation, oxalic acid, succinic acid, pyruvic acid malic, acid, malonic acid, salicylic acid, and anthranilic acid, and salts (for example, the sodium salts, calcium salts and/or potassium salts) thereof. In some implementations, the methods and compositions described herein include one or more polyphenol chelating agents. One non-limiting example of a polyphenol chelating agent is tannins such as tannic acid.

In some implementations, the chelating agent can include one or more hydroxycarboxylic acid chelating agents. Examples of the hydroxycarboxylic acid type chelating agents include, without limitation, malic acid, citric acid, glycolic acid, heptonic acid, tartaric acid and salts (for example, the sodium salts, calcium salts and/or potassium salts) thereof.

It will be understood that the one or more chelating agents can be provided as the free acid, as an agriculturally acceptable salt, or as combinations thereof. In some implementations, each of one or more the chelating agent(s) is applied as the free acid. In other implementations, the chelating agent(s) can be applied as a salt. Exemplary salts include sodium salts, potassium salts, calcium salts, ammonium salts, amine salts, amide salts, and combinations thereof. In still other implementations, when more than one chelating agent is present, at least one of the chelating agents is applied as a free acid, and at least one of the chelating agents is applied as a salt.

Additives and Adjuvants

In some implementations, the photosensitizer compound can be applied to a plant in combination with one or more agriculturally suitable adjuvants. Each of the one or more agriculturally suitable adjuvants can be independently selected from the group consisting of one or more activator adjuvants (e.g., one or more surfactants; e.g., one or more oil adjuvants, e.g., one or more penetrants) and one or more utility adjuvants (e.g., one or more wetting or spreading agents; one or more humectants; one or more emulsifiers; one or more drift control agents; one or more thickening agents; one or more deposition agents; one or more water conditioners; one or more buffers; one or more anti-foaming agents; one or more UV blockers; one or more antioxidants; one or more fertilizers, nutrients, and/or micronutrients; and/or one or more herbicide safeners). Exemplary adjuvants are provided in Hazen, J. L. Weed Technology 14: 773-784 (2000), which is incorporated by reference in its entirety.

In some implementations, the photosensitizer compound can be applied to a plant in combination with oil. The oil can be selected from the group consisting of a mineral oil (e.g., paraffinic oil), a vegetable oil, an essential oil, and a mixture thereof. In some scenarios, combining the photosensitizer compound with an oil can improve solubility of the photosensitizer compound when in contact with the plant. The oil can be added with the photosensitizer compound, or separately, in the presence or absence of a carrier fluid such as water.

Non-limiting examples of vegetable oils include oils that contain medium chain triglycerides (MCT), or oil extracted from nuts. Other non-limiting examples of vegetable oils include coconut oil, canola oil, soybean oil, rapeseed oil, sunflower oil, safflower oil, peanut oil, cottonseed oil, palm oil, rice bran oil or mixtures thereof. Non-limiting examples of mineral oils include paraffinic oils, branched paraffinic oils, naphthenic oils, aromatic oils or mixtures thereof.

Non-limiting examples of paraffinic oils include various grades of poly-alpha-olefin (PAO). For example, the paraffinic oil can include HT60™, HT100™, High Flash Jet, LSRD™ and N65DW™. The paraffinic oil can include a paraffin having a number of carbon atoms ranging from about 12 to about 50, or from about 16 to 35. In some scenarios, the paraffin can have an average number of carbon atoms of 23. In some implementations, the oil can have a paraffin content of at least 80 wt %, or at least 90 wt %, or at least 99 wt %.

The photosensitizer compound and the oil can be added sequentially or simultaneously. When added simultaneously, the nitrogen-bearing macrocyclic compound and the oil can be added as part of the same composition or as part of two separate compositions. In some implementations, the nitrogen-bearing macrocyclic compound and the oil can be combined in an oil-in-water emulsion. That is, the combination can include the nitrogen-bearing macrocyclic compound combined with the oil and water so that the combination is formulated as an oil-in-water emulsion. The oil-in-water emulsion can also include other additives such as a chelating agent, a surfactant, or combinations thereof.

As used herein, the term "oil-in-water emulsion" refers to a mixture in which one of the oil (e.g., the paraffinic oil) and water is dispersed as droplets in the other (e.g., the water). In some implementations, an oil-in-water emulsion is prepared by a process that includes combining the paraffinic oil, water, and any other components and the paraffinic oil and applying shear until the emulsion is obtained. In other implementations, an oil-in-water emulsion is prepared by a process that includes combining the paraffinic oil, water, and any other components in the mixing tank and spraying through the nozzle of a spray gun.

In some implementations, the photosensitizer compound is part of a composition that includes a carrier fluid. A suitable carrier fluid can allow obtaining a stable solution, suspension and/or emulsion of the components of the composition in the carrier fluid. In some implementations, the carrier fluid is water. In other implementations, the carrier fluid is a mixture of water and other solvents or oils that are non-miscible or only partially soluble in water.

In some implementations, a combination of photosensitizer compound and oil can be used to inhibit growth of a microbial pathogen in a plant. The combination can be an oil-in-water emulsion, where the surfactant is selected such that the photosensitizer compound is maintained in dispersion in the oil-in-water emulsion for delivery to the plant.

The combination can include a surfactant (also referred to as an emulsifier). The surfactant can be selected from the group consisting of an ethoxylated alcohol, a polymeric surfactant, a fatty acid ester, a poly(ethylene glycol), an ethoxylated alkyl alcohol, a monoglyceride, an alkyl monoglyceride, an amphipathic glycoside, and a mixture thereof. For example, the fatty acid ester can be a sorbitan fatty acid ester. The surfactant can include a plant derived glycoside such as a saponin. The surfactant can be present as an adjuvant to aid coverage of plant foliage. The surfactant can be an acceptable polysorbate type surfactant (e.g., Tween 80), a nonionic surfactant blend (e.g., Altox™ 3273), or another suitable surfactant.

In some implementations, the poly(ethylene glycol) can include a poly(ethylene glycol) of Formula $R^{15}$—O—$(CH_2CH_2O)_f$—$R^{16}$, wherein: each $R^{15}$ and $R^{16}$ is each, independently, H, alkyl, substituted alkyl, aryl, substituted aryl, CO(alkyl) or CO(substituted alkyl); and f is an integer selected from 1 to 100; wherein the substituted alkyl groups are, independently, substituted with one or more F, Cl, Br, I, hydroxy, alkenyl, CN and $N_3$.

Compositions Including a Photosensitizer Compound

It should also be understood that the photosensitizer compounds and the other agents (e.g., chelating agent, oil, surfactant, etc.) can be provided to a plant separately or together as part of the same composition. In some implementations, the components of the compositions can be packaged in a concentrated form, without carrier fluid, and the carrier fluid (e.g., water) can be added to form the composition directly by the operator that can then apply the composition to plants.

When the components are provided as part of a single composition, the composition can be provided to have certain concentrations and relative proportions of components. For example, the composition can have between about 100 nM and about 50 mM, between about 5 micromolar and about 10 mM, between about 1 micromolar and about 1000 micromolar, between about 5 micromolar and about 200 micromolar of the photosensitizer compound, between about 10 micromolar and about 150 micromolar of the nitrogen-bearing macrocyclic compound, between about 25 micromolar and about 100 micromolar of the nitrogen-bearing macrocyclic compound, or between about 50 micromolar and about 75 micromolar of the photosensitizer compound.

For example, and without being limiting, the composition can also include between about 2 micromolar and about 10,000 micromolar of the chelating agent, between about 5 micromolar and about 5,000 micromolar of the chelating agent, between about 10 micromolar and about 1,000 micromolar of the chelating agent, between about 25 micromolar and about 500 micromolar of the chelating agent, or between about 50 micromolar and about 100 micromolar of the chelating agent.

For example, and without being limiting, the relative proportion, by weight, of the nitrogen-bearing macrocyclic compound and the chelating agent in the composition can be between about 50:1 and about 1:1000, between about 20:1 and about 1:500, between about 10:1 and about 1:100, or between about 1:1 and about 1:10.

For example, and without being limiting, the photosensitizer compound and the oil can be applied in a relative proportion, by weight, between about 50:1 and about 1:1000, between about 20:1 and about 1:500, between about 10:1 and about 1:100, or between about 1:1 and about 1:10.

The composition including the photosensitizer compound can be applied to plants in various ways. For example, the composition can be prepared to include the photosensitizer compound, a chelating agent as well as a delivery fluid, such as water or a water-oil emulsion. The composition can be applied to the plant by spraying, misting, sprinkling, pouring, or any other suitable method. The anti-microbial composition can be applied to the foliage, roots and/or stem of the plant. Other additives can also be included in the anti-microbial composition, and other application methods can also be performed.

The plants on which the composition is applied can be outdoors or indoors (e.g., greenhouse) where they are exposed to natural sunlight, or in an indoor location where they are exposed to artificial light. The exposure to the incident light is provided such that the photosensitizer compound can generate ROS that, in turn, facilitate disruption of microbial growth.

In some implementations, the photosensitizer compound can be used to treat seeds or seedlings. In some scenarios, the treatment of seeds or seedlings can stimulate germination and growth, and/or can increase resistance of the plant to abiotic stresses. In some implementations, the seeds or seedlings can be treated with the photosensitizer compound prior to being planted into a growing medium. In some implementations, the seeds or seedlings can be treated with the photosensitizer compound after being planted into a growing medium.

The photosensitizer compound can be directly surface-coated onto the seeds, applied to seedlings roots or seedlings leafs (foliar application on seedlings). In some implementations, a solution or emulsion containing the photosensitizer compound can be directly sprayed onto the seeds or seedlings. In some implementations, the seeds or seedlings can be dipped into a solution or emulsion containing the photosensitizer compound. In some implementations, the root of the seedling can be dipped into a solution or emulsion containing the photosensitizer compound. In some implementations, the seeds can be placed into a container, and a solution containing the photosensitizer compound can be introduced into the container. The container can then be shaken for an appropriate period (e.g., between about 1 minute to several minutes) such that the solution contacts the seeds. The shaken seeds can then be dried (e.g., air dried) prior to being planted.

The photosensitizer compound can be applied once, twice, or more than twice to seeds or seedlings, using various modes of application. For example, the seeds can be treated after having been planted into a growing medium. In another example, the seeds and/or seedlings can be treated prior to having been planted and after having been planted (e.g., in furrow treatment and/or foliar application). In yet another example, the seed can be treated prior to having been planted and/or after having been planted, and the ensuing seedling can be further treated (e.g., root treatment and/or foliar treatment).

Microbial Pathogens

The microbial pathogens to which the composition including the photosensitizer compound can be applied include fungal and bacterial pathogens. In such case, the composition can be referred to as an "anti-microbial composition".

The fungal pathogens to which the anti-microbial composition can be applied include *Alternaria solani*, which can infect plants such as tomatoes and potatoes; *Botrytis cinerea*, which can infect grapes, as well as soft fruits and bulb crops; or *Sclerotinia homoeocarpa*, which can commonly infect turfgrasses. Other fungal pathogens in the *Alternaria*, *Botrytis* or *Sclerotinia* genera can also receive application of the anti-microbial composition. The anti-microbial composition can be applied to plants that are affected or susceptible to pathogens that cause various plant diseases, e.g., *Colletotrichum*, *Fusarium*, *Puccinia*, *Erysiphaceae*, *Cercospora*, *Rhizoctonia*, *Bipolaris*, *Microdochium*, *Venturia inaequalis*, *Monilinia fructicola*, *Gymnosporangium juniperi-virginianae*, *Plasmodiophora brassicae*, *Ustilago zeae*, *Phytophthora*, *Pythium*, *Fusarium oxysporum*, *Phytophthora infestans*, *Taphrina deformans*, Powdery Mildew, *Phragmidium* spp., or other fungal pathogens.

The bacterial pathogens to which the anti-microbial composition can be applied include gram-negative bacteria, such as *Erwinia amylovara*, or other bacterial pathogens in the genus *Erwinia* that can infect woody plants. *E. amylovara* causes fire blight on various plants, including pears, apples, and other Rosaceae crops. The anti-microbial composition can be applied to plants that are affected or susceptible to pathogens that cause various plant diseases, e.g., *Pseudomonas*, *Xanthomonas*, *Agrobacterium*, *Curtobacterium*, *Streptomyces*, *E. Coli*, *Xylella fastidiosa* (which causes Olive Quick Decline Syndrome (OQDS) disease), or other bacterial pathogens.

It is also noted that the anti-microbial compositions described herein can have various inhibitory effects on the microbial pathogens depending on the type of plant and pathogen as well as the state of microbial infection. While herein it is described that the anti-microbial composition can inhibit microbial pathogen growth on a plant, such expressions should not be limiting but should be understood to include suppression of microbial pathogens, prevention against microbial pathogens, killing of microbial pathogens or generally increase toxicity toward microbial pathogens.

Abiotic Stresses

As mentioned above, in some implementations, the photosensitizer compounds and compositions of the present description can be used to increase tolerance of plants to one or more abiotic stresses such as photooxidative conditions, drought (water deficit), excessive watering (flooding, and submergence), extreme temperatures (chilling, freezing and heat), extreme levels of light (high and low), radiation (UV-B and UV-A), salinity due to excessive $Na^+$ (sodicity), chemical factors (e.g., pH), mineral (metal and metalloid) toxicity, deficiency or excess of essential nutrients, gaseous pollutants (ozone, sulfur dioxide), wind, mechanical factors, and other stressors.

Cold Hardiness

When the abiotic stress is cold stress, application of the photosensitizer compound, alone or in combination with additives such as an oil, a surfactant and/or a chelating agent, can improve cold hardiness of the plant. That is, application of the photosensitizer compound can allow the plant to withstand temperature conditions that are colder than would typically be experienced in the plant's optimal or native growing conditions. Various types of cold stress are possible, such as unexpected frost (for example an early fall frost when healthy crop, fruit, grain, seeds or leaves are still present on the plant, or a late spring frost that occurs after spring plant growth has begun), a cooler than average growing season, colder than native winter conditions, minimal winter snow cover, ice accumulation, etc.

It should be noted that what constitutes a cold stress condition for one plant may not be a cold stress condition for another plant. With reference to the USDA zone map, a cold stress condition for a zone 9 plant may in fact be a native growing condition for a zone 8 plant. Likewise, the depth of snow cover required for survival of one type of plant may not be required for a second type of plant. It is therefore understood that various types of cold stress are possible, depending on the type of plant in question.

The photosensitizer compound, compositions or combinations described herein may be used to protect plants, including woody plants, non-woody plants and turfgrasses, from frost injury. The frost can be an early frost, for example before harvest, after harvest and before dormancy. The frost can be a late frost, for example after budding. The cold damage can also be winter kill induced by winter temperatures, which may result in a loss of viable branches or shoots and lead to plant mortality. Plants treated by the photosensitizer compound, compositions or combinations described herein can be frost or cold sensitive plants, in that they are naturally susceptible to frost, freezing or cold damage or injury in economically or aesthetically significant amounts.

Increasing resistance to cold stress can be exemplified by a delayed onset of dormancy. Plant dormancy can be triggered by a drop in temperature, e.g., the onset of cold stress. By increasing resistance of the plant to cold stress, dormancy of the plant can be delayed until triggered by a further drop in temperature.

The photosensitizer compound, compositions or combinations described herein can be used periodically (e.g., at 2 or 3-week intervals starting with spring at breaking the dormancy) and/or by applying one or more treatments (e.g., 2 in the fall), to provide a response in reducing or delaying the dormancy period of certain plants.

As used herein, the term "reducing dormancy period" refers to a plant that has a reduced dormancy period or extended growing period relative to a control, e.g., a non-treated plant.

In some implementations, the harvesting step may be carried out one week, one month, two months or more after the last application of the photosensitizer compound, compositions or combinations described herein, with the active agent still being effective to reduce the effects of cold stress on the plant during the intervening period.

In some scenarios, resistance to cold stress includes resistance to early or late frost, or winter damage. In some scenarios, the photosensitizer compound, compositions or combinations described herein can be used to protect early growth from cold during fluctuations in temperature (e.g., in early spring). In some scenarios, the photosensitizer compound, compositions or combinations described herein can be used to protect plants from cold during the cold months (e.g., in winter).

In some scenarios, the photosensitizer compound, compositions or combinations described herein can be applied by soil drenching and/or foliar application (e.g., sprayed until run-off) at the onset or prior to exposure to the low temperature (e.g., fall when the trees have full healthy and vigorous foliage). In some scenarios, the photosensitizer compound, compositions or combinations described herein can be applied by soil drenching and/or foliar application (e.g., sprayed until run-off) during late fall and winter (e.g., for warm climates). In some scenarios, the photosensitizer compound, compositions or combinations described herein can be applied by soil drenching in the late fall following by a foliar application (e.g., sprayed until run-off) in the winter in order to reach maximum hardiness.

In some scenarios, the photosensitizer compound, compositions or combinations described herein can be applied 1-4 times at a 1 to 6-month interval (e.g., every 2 to 3 months). Further treatments may be applied in the spring and/or during the growing season to improve resistance to subsequent cold stress conditions.

Heat Hardiness

When the abiotic stress is heat stress, application of the photosensitizer compound, compositions or combinations described herein can improve tolerance to high temperatures during the growing season. That is, application of the photosensitizer compound, compositions or combinations described herein can allow the plant to withstand temperature conditions that are higher than would typically be experienced in the plant's optimal or native growing conditions. Heat stress can have various causes, such as lack of shade for plants that typically require shaded growing conditions, or higher than normal soil and air temperatures.

It should be noted that what constitutes a heat stress condition for one plant may not be a heat stress condition for another plant.

Photooxidative Hardiness

When the abiotic stress is photooxidative stress, application of the photosensitizer compound, compositions or combinations described herein can improve tolerance to stressful light condition during periods of increased generation of reactive oxygen species. That is, application of the photosensitizer compound, compositions or combinations described herein can allow the plant to withstand light exposure conditions (e.g., ultraviolet irradiation conditions) that are higher than would typically be experienced in the plant's optimal or native growing conditions. Photooxidative stress can have various causes, such as high light conditions or certain types of lighting that induce formation of free radicals.

It should be noted that what constitutes a photooxidative stress condition for one plant may not be a photooxidative stress condition for another plant.

Shade Hardiness

Shade stress, or "low light (LL) stress" can be a problem that influences plant growth and quality. When the abiotic stress is shade stress, application of the photosensitizer compound, compositions or combinations described herein can improve shade hardiness of the plant. That is, application of the photosensitizer compound, compositions or combinations described herein can allow the plant to withstand shady conditions for plants whose optimal or native growing conditions typically require partial or full sun exposure. Various types of shade stress are possible, such as a prolonged period of cloudy weather, excessive growth of adjacent plants or trees that cast shade onto the plant, or lack of availability of a sunny planting location.

Shade can be a periodic problem. For example, during certain months of the year, a structure situated near a plant may cast a shadow on the plant, causing a shade stress. As the earth moves over the course of a year, the structure may no longer cast the shadow on the plant for another series of months and then the situation can be repeated during the next annual cycle. In such instances, the photosensitizer compound, compositions or combinations described herein can be applied to the plant prior to onset of the period of shade stress and can also be applied during the period of shade stress. The damage to the plant that would typically result on account of the period of shade stress can be prevented or reduced.

Shade conditions are not considered to be an abiotic stress condition for many types of plants, as some plants have a requirement for shade as part of their optimal growing conditions. It should also be noted that what constitutes a shade stress condition for one plant may not be a shade stress condition for another plant.

Drought Hardiness

Drought can be defined as the absence of rainfall or irrigation for a period of time sufficient to deplete soil moisture and injure plants. Drought stress results when water loss from the plant exceeds the ability of the plant's roots to absorb water and/or when the plant's water content is reduced enough to interfere with normal plant processes. The severity of the effect of a drought condition may vary between plants, as the plant's need for water may vary by plant type, plant phenological stage, plant age, root depth, soil quality, etc.

The photosensitizer compound, compositions or combinations described herein can be applied to a plant prior to onset of a drought and/or during a drought. Application of the photosensitizer compound, compositions or combinations described herein can increase the resistance of the plant to the drought stress. Increasing resistance can include maintaining or increasing a quality of the plant as compared to an untreated plant subjected to the same drought stress. Increasing resistance can include reducing the degradation in quality of the plant, as compared to an untreated plant subjected to the same drought stress. If plants do not receive adequate rainfall or irrigation, the resulting drought stress can reduce growth more than all other environmental stresses combined.

It should also be noted that what constitutes a drought stress condition for one plant may not be a drought stress condition for another plant.

Prevention of Salt Damage

Salts can be naturally present in the growing environment of a plant. Salinity stress refers to osmotic forces exerted on a plant when the plant is growing in a saline soil or under other excessively saline conditions. For example, plants growing near a body of salt water can be exposed to salt present in the air or in water used to water the plants. In another example, salt applied to road, sidewalk and driveway surfaces during the winter for improved driving conditions can be transferred and/or leach into the soil of plants growing in the proximity. Such increased salt content in a growing environment of the plant can result in salinity stress, which can damage the plant.

Application of the photosensitizer compound, compositions or combinations described herein to the plant can increase the plant's resistance to the salinity stress and prevent or reduce a deterioration in quality of the plant which would occur if untreated. The combination can be applied prior to or during the period of salinity stress.

It should also be noted that what constitutes a salt stress condition for one plant may not be a salt stress condition for another plant.

Transplant Shock Hardiness

A plant that is subjected to transplanting from one growing environment to another, e.g., from a pot to flower bed or garden, can be subjected to transplant shock stress as a result of exposure to new environmental conditions such as wind, direct sun, or new soil conditions. Application of the photosensitizer compound, compositions or combinations described herein to the roots of the plant can reduce the impact to the plant caused by the transplanting. In some scenarios, stunting of plant growth and/or development of a transplanted plant can be reduced or prevented by application of the photosensitizer compound, compositions or combinations described herein.

It should be noted that what constitutes a transplant shock stress condition for one plant may not be a transplant shock stress condition for another plant.

Excess Water or Flooding Hardiness

Although plants require a certain volume of water for healthy plant growth and development, the exposure of a plant to excess volumes of water ("water stress") can damage the plant. Application of the photosensitizer compound, compositions or combinations described herein to a plant prior to the onset of an excess water condition can increase the plant's resistance to the water stress. The photosensitizer compound, compositions or combinations described herein can be applied during the water stress, however, dilution of the photosensitizer compound, compositions or combinations described herein may occur on account of the excess water. Accordingly, pre-treatment in advance of a period of excess water can be more effective.

It should be noted that what constitutes an excess water stress condition for one plant may not be an excess water stress condition for another plant.

Insecticide Activity

In some implementations, the compounds and combinations of the present description can be used to protect the plant from a plant pest. In should be understood that the term "plant pest" or "pest", as used herein, refers to insects and/or their larvae, which are known to or have the potential to cause damage to the plant. In some implementations, the compounds and combinations of the present description can induce photoinduced mortality in plant pests.

In some implementations, the insect pests are selected from the order of Hemiptera (groups of aphids, whiteflies, scales, mealybugs, stink bugs), Coleoptera (groups of beetles), Lepidoptera (groups of butterflies, moths), Diptera (groups of flies), Thysanoptera (group of thrips), Orthoptera (group of grasshoppers, locusts), Hymenoptera (groups of wasps, ants), Blattodea (groups of cockroaches and termites) and mite pests (spider mites).

Non-limiting examples of insect pests include: larvae of the order Lepidoptera, such as armyworms, (e.g., beet armyworm (*Spodoptera exigua*)), cutworms, loopers, (e.g., cabbage looper (*Trichoplusia ni*)) and heliothines, in the family Noctuidae (e.g., fall armyworm (*Spodoptera fugiperda* J. E. Smith)), beet armyworm (*Spodoptera exigua* Hubner), black cutworm (*Agrotis ipsilon* Hufnagel), and tobacco budworm (*Heliothis virescens* Fabricius); borers, casebearers, webworms, coneworms, cabbageworms and skeletonizers from the family Pyralidae (e.g., European corn borer (*Ostrinia nubilalis* Hubner)), navel orangeworm (*Amyelois transitella* Walker), corn root webworm (*Crambus caliginosellus* Clemens), and sod webworms (Pyralidae: Crambinae) such as sod webworm (*Herpetogramma licarsisalis* Walker), leafrollers, budworms, seed worms, and fruit worms in the family Tortricidae (e.g., codling moth (*Cydia pomonella* Linnaeus)), grape berry moth (*Endopiza viteana* Clemens), oriental fruit moth (*Grapholita molesta* Busck) and many other economically important Lepidoptera (e.g., diamondback moth (*Plutella xylostella* Linnaeus)), pink bollworm (*Pectinophora gossypiella* Saunders), and gypsy moth (*Lymantria dispar* Linnaeus); foliar feeding larvae and adults of the order Coleoptera including weevils from the families Anthribidae, Bruchidae, and Curculionidae (e.g., boll weevil (*Anthonomus grandis* Boheman)), rice water weevil (*Lissorhoptrus oryzophilus* Kuschel), granary weevil (*Sitophilus granarius* Linnaeus), rice weevil (*Sitophilus oryzae* Linnaeus), annual bluegrass weevil (Listronotus *maculicollis* Dietz), bluegrass billbug (*Sphenophorus parvulus* Gyllenhal), hunting billbug (*Sphenophorus venatus vestitus*), Denver billbug (*Sphenophorus cicatristriatus* Fahraeus), flea beetles, cucumber beetles, rootworms, leaf beetles, Colorado potato beetles (*Leptinotarsa decemlineata*), and leafminers in the family Chrysomelidae, western corn rootworm (*Diabrotica virgifera virgifera* LeConte); chafers and other beetles from the family Scaribaeidae (e.g., Japanese beetle (*Popillia japonica* Newman)), oriental beetle (*Anomala orientalis* Waterhouse), northern masked chafer (*Cyclocephala borealis* Arrow), southern masked chafer (*Cyclocephala immaculate* Olivier), black turfgrass ataenius (*Ataenius spretulus* Haldeman), green June beetle (*Cotinis nitida* Linnaeus), Asiatic garden beetle (*Maladera castanea* Arrow), May/June beetles (*Phyllophaga* spp.) and European chafer (*Rhizotrogus majalis* Razoumowsky)); carpet beetles from the family Dermestidae; wireworms from the family Elateridae; bark beetles from the family Scolytidae; flour beetles from the family Tenebrionidae; adults and nymphs of the order Orthoptera including grasshoppers, locusts, and crickets (e.g., migratory grasshoppers (e.g., *Melanoplus sanguinipes* Fabricius, *M. differentialis* Thomas)), American grasshoppers (e.g., *Schistocerca americana* Drury), desert locust (*Schistocerca gregaria* Forskal), migratory locust (*Locusta migratoria* Linnaeus), bush locust (*Zonocerus* spp.); adults and larvae of the order Diptera including leafminers, midges, fruit flies (Tephritidae), fruit flies (e.g., *Oscinella frit* Linnaeus), soil maggots; adults and nymphs of the orders Hemiptera and Homoptera such as plant bugs from the family Miridae, leafhoppers (e.g., *Empoasca* spp.) from the family Cicadellidae; planthoppers from the families Fulgoroidae and Delphacidae (e.g., corn plant hopper (*Peregrinus maidis*)); treehoppers from the family Membracidae; chinch bugs (e.g., hairy chinch bug (*Blissusleucopterus hirtus* Montandon) and southern chinch bug (*Blissus insularis* Barber) and other seed bugs from the family Lygaeidae; spittlebugs from the family Cercopidae; squash bugs from the family Coreidae; red bugs and cotton stainers from the family Pyrrhocoridae; mealybugs from the family Pseudococcidae (e.g. *Planicoccus citri* Risso), cicadas from the family Cicadidae; psyllids from the family Psyllidae (e.g. Citrus psyllid *Diaphorina citri*)), whiteflies from the family Aleyrodidae (silverleaf whitefly (*Bemisia argentifolii*)); aphids from the family Aphididae, such as cotton melon aphid (*Aphis gossypil*), pea aphid (*Acyrthisiphon pisum* Harris), cowpea aphid (*Aphis craccivora* Koch), black bean aphid (*Aphis fabae* Scopoli), melon or cotton aphid (*Aphis gossypii* Glover), apple aphid (*Aphis pomi* De Geer), spirea aphid (*Aphis spiraecola* Patch), foxglove aphid (*Aulacorthum solani* Kaltenbach), strawberry aphid *Chaetosiphon fragaefolii* Cockerell), Russian wheat aphid (*Diuraphis noxia* Kurdjumov/Mordvilko), rosy apple aphid (*Dysaphis plantaginea* Paaserini), woolly apple aphid (*Eriosoma lanigerum* Hausmann), mealy plum aphid (*Hyalopterus pruni* Geoffroy), turnip aphid (*Lipaphis erysimi* Kaltenbach), cereal aphid (*Metopolophium dirrhodum* Walker), potato aphid (*Macrosipum euphorbiae* Thomas), peach-potato and green peach aphid (*Myzus persicae* Sulzer), lettuce aphid (*Nasonovia ribisnigri* Mosley), root aphids and gall aphids, corn leaf aphid (*Rhopalosiphum maidis* Fitch), bird cherry-oat aphid (*Rhopalosiphum padi* Linnaeus), greenbug (*Schizaphis graminum* Rondani), English grain aphid (*Sitobion avenae* Fabricius), spotted alfalfa aphid (*Therioaphis maculata* Buckton), black citrus aphid (*Toxoptera aurantii* Boyer de Fonscolombe), brown citrus aphid (*Toxoptera citricida* Kirkaldy) and green peach aphid (*Myzus persicae*); phylloxera from the family Phylloxeridae; mealybugs from the family Pseudococcidae; scales from the families Coccidae, Diaspididae, and Margarodidae; lace bugs from the family Tingidae; stink bugs from the family Pentatomidae; adults and immatures of the order Thysanoptera including onion thrips (*Thrips tabaci* Lindeman), flower thrips (*Frankliniella* spp.), and other foliar feeding thrips. Agronomic pests also include invertebrate arthropods such as mites from the family Tetranychidae: twospotted spider mite (e.g. *Tetranychus urticae* Koch), flat mite from family Rutacea (e.g., citrus flat mite (*Brevipalpus lewisi* McGregor); rust and bud mites from the family Eriophyidae and other foliar feeding mites. Economically important agricultural pests nematodes (e.g., root knot nematodes in the genus *Meloidogyne*, lesion nematodes in the genus *Pratylenchus*, and stubby root nematodes in the genus *Trichodorus*) and members of the classes Nematoda, Cestoda, Trematoda, and Acanthocephala from orders of Strongylida, Ascaridida, Oxyurida, Rhabditida, Spirurida, and Enoplida.

The photosensitizer compounds of the present description can be applied to the plant before, at or after infestation of the plant by the insect pests.

In some implementations, the photosensitizer compounds of the present description can be used as insecticides by applying them to insects (i.e., without applying the photosensitizers to a plant). The present description therefore also provides a method for controlling insect population. The method includes applying to the insects a photosensitizer compound of the present description; and exposing the insects to light to activate the photosensitizer compound and generate reactive oxygen species.

It should be understood that applying the photosensitizer to the insects can include indirectly applying the photosensitizer to the insect pests (e.g., by applying the photosensitizer to a food source that is then fed to the insects) and/or directly applying the photosensitizer to the insect pests (e.g., by directly contacting the insects with the photosensitizer, such as by spraying a composition including the photosensitizer onto the insects).

Types of Plants

The photosensitizer compounds and compositions of the present description can be used for various types of plants. The plant can be a non-woody crop plant, a woody plant or a turfgrass. The plant can be selected from the group consisting of a crop plant, a fruit plant, a vegetable plant, a legume plant, a cereal plant, a fodder plant, an oil seed plant, a field plant, a garden plant, a green-house plant, a house plant, a flower plant, a lawn plant, a turfgrass, a tree such as a fruit-bearing tree, and other plants that may be affected by microbial pathogens and/or one or more abiotic stress. Some of the compounds of the present description can display a certain degree of toxicity against a variety of noxious plant pests, in the absence or presence of light.

In some implementations, the plant is a crop plant selected from the group consisting of sugar cane, wheat, rice, corn (maize), potatoes, sugar beets, barley, sweet potatoes, cassava, soybeans, tomatoes, and legumes (beans and peas).

In other implementations, the plant is a tree selected from the group consisting of deciduous trees and evergreen trees. Examples of trees include, without limitation, maple trees, fruit trees such as citrus trees, apple trees, and pear trees, an oak tree, an ash tree, a pine tree, and a spruce tree.

In yet other implementations, the plant is a shrub.

In yet other implementations, the plant is a fruit or nut plant. Non-limiting examples of such plants include: acerola (barbados cherry), atemoya, carambola (star fruit), rambutan, almonds, apricots, cherries, nectarines, peaches, pistachio, apples, avocados, bananas, plantains, figs, grapes, mango, olives, papaya, pears, pineapple, plums, strawberries, grapefruit, lemons, limes, oranges (e.g., navel and Valencia), tangelos, tangerines, mandarins and plants from the berry and small fruits plant group.

In other implementations, the plant is a vegetable plant. Non-limiting examples of such plants include: asparagus, bean, beets, broccoli, Chinese broccoli, broccoli raab, brussels sprouts, cabbage, cauliflower, Chinese cabbage (e.g., bok choy and mapa), Chinese mustard cabbage (gai choy), cavalo broccoli, collards, kale, kohlrabi, mizuna, mustard greens, mustard spinach, rape greens, celery, chayote, Chinese waxgourd, citron melon, cucumber, gherkin, hyotan, cucuzza, hechima, Chinese okra, balsam apple, balsam pear, bitter melon, Chinese cucumber, true cantaloupe, cantaloupe, casaba, crenshaw melon, golden pershaw melon, honeydew melon, honey galls, mango melon, Persian melon, pumpkin, summer squash, winter squash, watermelon, dasheen (taro), eggplant, ginger, ginseng, herbs and spices (e.g., curly leaf basil, lemon balm, cilantro, Mexican oregano, mint), Japanese radish (daikon), lettuce, okra, peppers, potatoes, radishes, sweet potatoes, Chinese artichoke (Japanese artichoke), corn and tomatoes.

In other implementations, the plant is a flowering plant, such as roses, flowering shrubs or ornamentals. Non-limiting examples of such plants include: flowering and foliage plants including roses and other flowering shrubs, foliage ornamentals & bedding plants, fruit-bearing trees such as apple, cherry, peach, and pear trees, non-fruit-bearing trees, shade trees, ornamental trees, and shrubs (e.g., conifers, deciduous and broadleaf evergreens & woody ornamentals).

In some implementations, the plant is a houseplant. Non-limiting examples of such plants include: chrysanthemum, dieffenbachia, dracaena, ferns, gardenias, geranium, jade plant, palms, philodendron, and schefflera.

In some implementations, the plant is a plant grown in a greenhouse. Non-limiting examples of such plants include: ageratum, crown of thorns, dieffenbachia, dogwood, dracaena, ferns, ficus, holly, lisianthus, magnolia, orchid, palms, petunia, poinsettia, schefflera, sunflower, aglaonema, aster, azaleas, begonias, browallia, camellias, carnation, celosia, chrysanthemum, coleus, cosmos, crepe myrtle, dusty miller, easter lilies, fuchsia, gardenias, gerbera, hellichrysum, hibiscus foliage, hydrangea, impatiens, jade plant, marigold, new guinea, impatiens, nicotonia, philodendron, portulaca, reiger begonias, snapdragon, and zinnias.

Synergistic Effect of the Combinations

In some scenarios, the combinations can exhibit a synergistic response for inhibiting growth of microbial pathogens in plants. It should be understood that the terms "synergy" or "synergistic", as used herein, refer to the interaction of two or more components of a combination (or composition) so that their combined effect is greater than the sum of their individual effects. This may include, in the context of the present description, the action of two or more of the nitrogen-bearing macrocyclic compounds, the oil, and the chelating agent. In some scenarios, the nitrogen-bearing macrocyclic compound and the oil can be present in synergistically effective amounts. In some scenarios, the nitrogen-bearing macrocyclic compound and the chelating agent can be present in synergistically effective amounts. In some scenarios, the oil and the chelating agent can be present in synergistically effective amounts. In some scenarios, the nitrogen-bearing macrocyclic compound, the oil and the chelating agent can be present in synergistically effective amounts.

In some scenarios, the approach as set out in S. R. Colby, "Calculating synergistic and antagonistic responses of herbicide combinations", Weeds 15, 20-22 (1967), can be used to evaluate synergy. Expected efficacy, E, may be expressed as: $E=X+Y(100-X)/100$, where X is the efficacy, expressed in % of the untreated control, of a first component of a combination, and Y is the efficacy, expressed in % of the untreated control, of a second component of the combination. The two components are said to be present in synergistically effective amounts when the observed efficacy is higher than the expected efficacy.

EXAMPLES

Compounds

PP IX-di-DMAE and PP IX-mono-DMAE

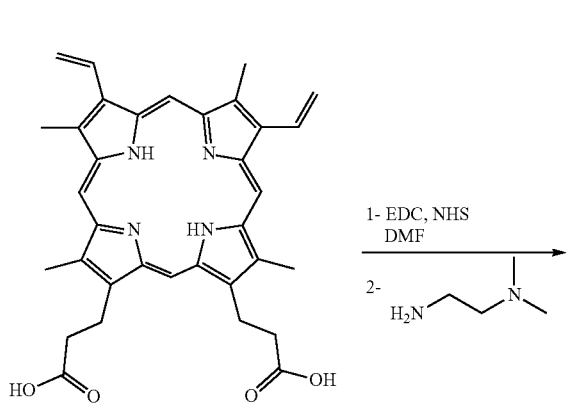

-continued

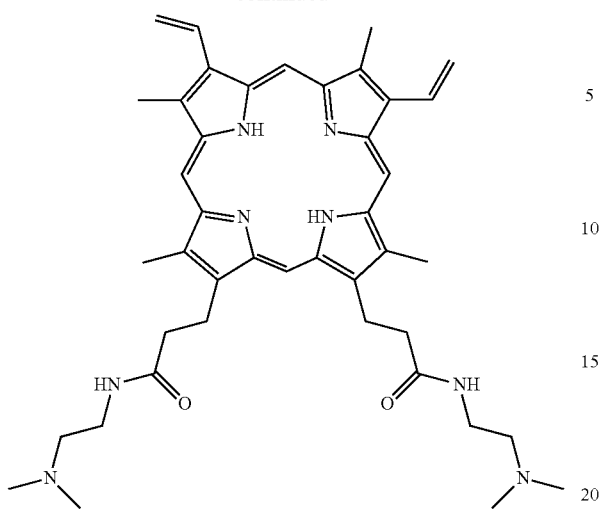

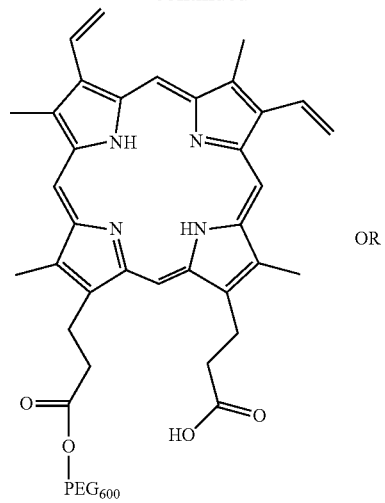

-continued

Protoporphyrin IX (500 mg, 0.89 mmol) and N-Hydroxysuccinimide (NHS, 245 mg, 2.136 mmol) were dissolved in 100 mL of DMF at 0° C. 1-Ethyl-3-(3-dimethylaminopropyl)carbodiimide hydrochloride (EDC, 409 mg, 2.136 mmol) in 10 mL DMF was then added to the reaction mixture and stirred at room temperature for 6 h. 2-Dimethylaminoethylamine (0.188 mg, 2.136 mmol) was then added and the solution was stirred overnight at room temperature. DMF was removed in vacuo and the residue was dissolved in 25 mL of methanol. The product was precipitated in cold ether (yield 80%).

The product contained about 50% di-substituted compound and 50% mono-substituted compound. When the reaction was performed a second time using the first product as starting material, the ratio was brought up to 80% di-substituted compound and 20% mono-substituted compound.

PP IX-mono-DMAE amide: MS-ESI (HRMS) m/z calculated for C38 H44 N6 O3 (M+H$^+$): 633.35. Found: 633.087.

PP IX-di-DMAE amide: MS-ESI (HRMS) m/z calculated for C42 H54 N8 O2 (M): 703.44 Found: 703.611.

PP IX mono-PEG$_{600}$

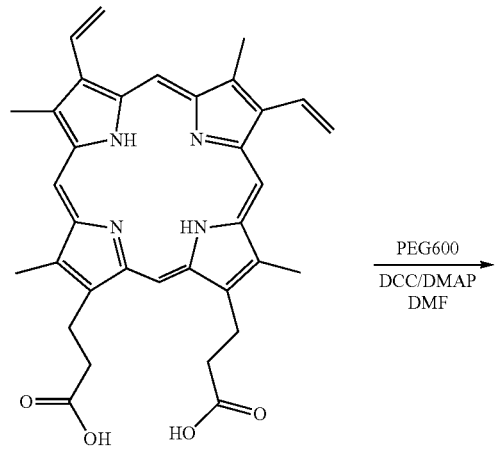

PEG600
———————→
DCC/DMAP
DMF

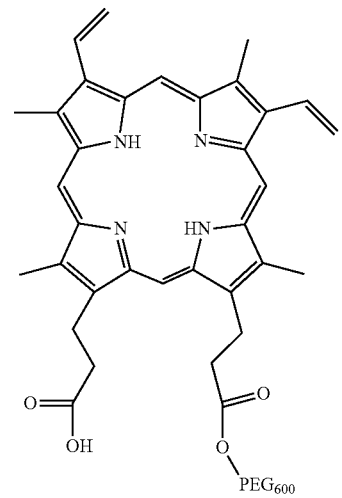

Protoporphyrin IX (500 mg, 0.89 mmol) and N-Hydroxysuccinimide (NHS, 307 mg, 2.67 mmol) were dissolved in DMF (50 ml). The solution of 1-ethyl-3-(3-dimethylaminopropy-I)carbodiimidehydrochloride (EDC, 512 mg, 2.67 mmol) in DMF (10 ml) was then added to the reaction mixture and allowed to stirred overnight at room temperature. Methoxyl polyethylene glycol 600 (mPEG-OH600, 640 mg, 1.06 mmol) was added to the solution and stirred overnight at room temperature. The mixture was concentrated to afford the product. The crude product was purified by flash column chromatography over silica gel, eluting with PE/ME (5:1 to 2:1) to give the product.

Mass spectrometry and $^1$H NMR analyses confirmed that a mixture of both PP IX mono-PEG$_{600}$ was obtained.

PP IX di-PEG$_{600}$

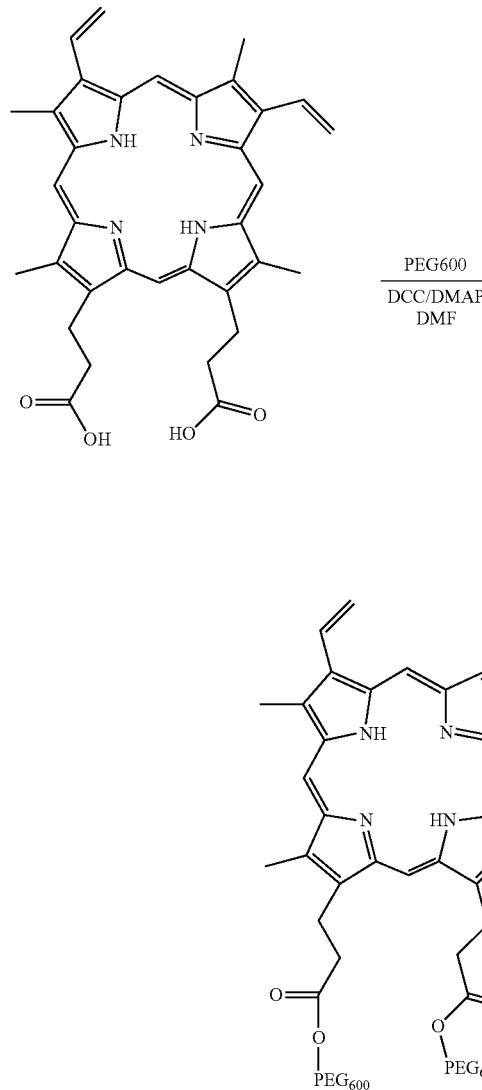

PP IX-mono-L-Alanine

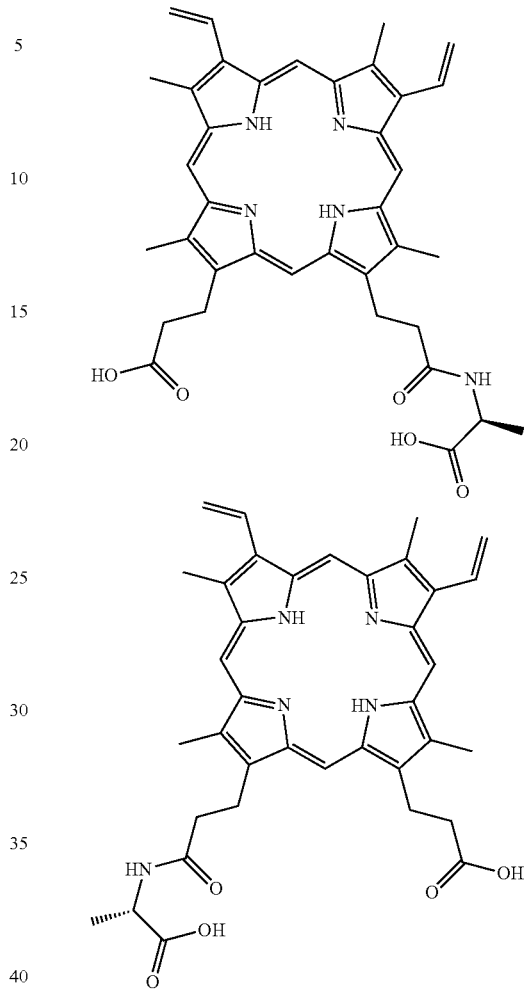

A mixture of Protoporphyrin IX (500 mg, 0.89 mmol) and N-Hydroxysuccinimide (307 mg, 2.67 mmol) in DMF (50 ml) was stirred at 0° C. for 1 h. A solution of 1-ethyl-3-(3-dimethylaminopropyl)carbodiimidehydrochloride (512 mg, 2.67 mmol) in DMF (10 ml) was then added to the reaction mixture and allowed to stir overnight at room temperature.

To a solution of L-Alanine in water, cooled to 0° C., was added triethylamine and di-tert-butyl dicarbonate. The reaction mixture was stirred at room temperature for 2 h. The pH was adjusted to about 6 by progressively adding a 10% w/v aqueous citric acid solution. The combined aqueous layers were extracted with ethyl acetate and the combined organic layers were dried over $Na_2SO_4$ and concentrated under vacuum. The product obtained (200 mg) was added to the previously obtained EDC-activated reaction mixture.

The mixture was adjusted to pH 9 with 10% HCl and concentrated to afford a crude product. The crude product was dissolved in methanol (50 ml) and filtered. The filtrate was slowly dripped into methyl tert-butyl ether (200 ml) at 0° C. and filtered to obtain PP IX-mono-L-Analine as a mixture containing mainly the two L-Alanine mono-substituted PP IX compounds.

Protoporphyrin IX (500 mg, 0.89 mmol) and N-Hydroxysuccinimide (NHS, 610 mg, 5.2 mmol) were dissolved in DMF (50 ml) stirring at 0° C. for 1 h. A solution of 1-ethyl-3-(3-d imethylaminopropyl)carbodiimidehydrochloride (EDC, 1012.0 mg, 5.2 mmol) in DMF (10 ml) was then added to the solution. The mixture was stirred overnight at room temperature. PEG600 (1290.0 mg, 2.2 mmol) was then added to the solution and further stirred overnight at room temperature. The mixture was concentrated to afford the crude product. The crude product was purified by flash column chromatography over silica gel, eluting with PE/ME (5:1 to 2:1) to give the product.

Mass spectrometry and $^1$H NMR analyses confirmed that PP IX di-PEG$_{600}$ was obtained as the major product.

Mass spectrometry and $^1$H NMR analyses confirmed that PP IX-mono-L-Alanine was obtained as the major product.

PP IX-mono-L-Valine

PP IX-mono-Glycine

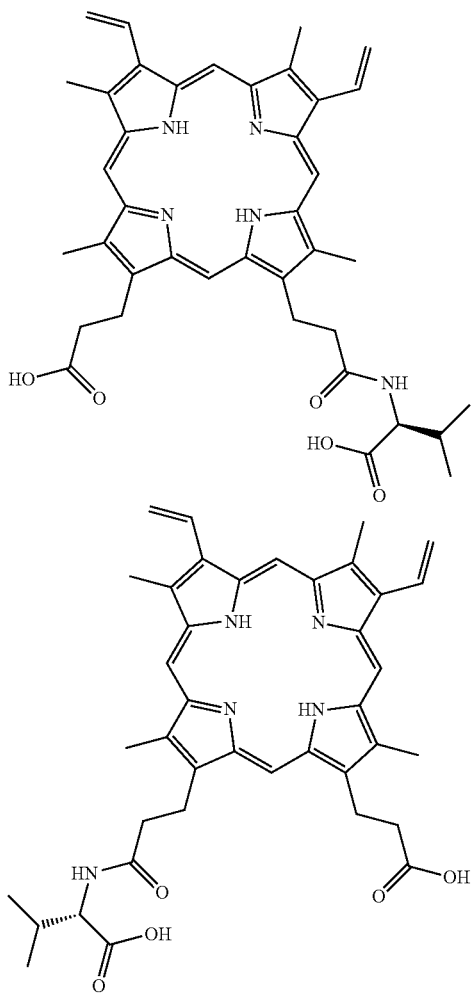

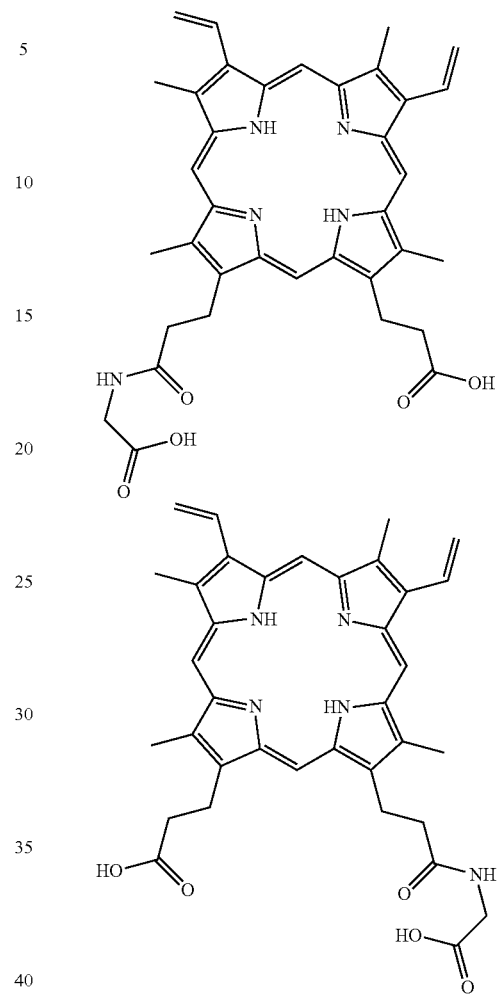

A mixture of Protoporphyrin IX (500 mg, 0.89 mmol) and N-Hydroxysuccinimide (307 mg, 2.67 mmol) in DMF (50 ml) was stirred at 0° C. for 1 h. A solution of 1-ethyl-3-(3-dimethylaminopropyl)carbodiimidehydrochloride (512 mg, 2.67 mmol) in DMF (10 ml) was then added to the reaction mixture and allowed to stir overnight at room temperature.

To a solution of L-Valine in water, cooled to 0° C., was added triethylamine and di-tert-butyl dicarbonate. The reaction mixture was stirred at room temperature for 2 h. The pH was adjusted to about 6 by progressively adding a 10% w/v aqueous citric acid solution. The combined aqueous layers were extracted with ethyl acetate and the combined organic layers were dried over $Na_2SO_4$ and concentrated under vacuum. The product obtained (200 mg) was added to the previously obtained EDC-activated reaction mixture.

The mixture was adjusted to pH 9 with 10% HCl and concentrated to afford a crude product. The crude product was dissolved in methanol (50 ml) and filtered. The filtrate was slowly dripped into methyl tert-butyl ether (200 ml) at 0° C. and filtered to obtain PP IX-mono-L-Valine as a mixture containing mainly the two L-Valine mono-substituted PP IX compounds.

Mass spectrometry and $^1$H NMR analyses confirmed that PP IX-mono-L-Valine was obtained as the major product.

A mixture of Protoporphyrin IX (500 mg, 0.89 mmol) and N-Hydroxysuccinimide (307 mg, 2.67 mmol) in DMF (50 ml) was stirred at 0° C. for 1 h. A solution of 1-ethyl-3-(3-dimethylaminopropyl)carbodiimidehydrochloride (512 mg, 2.67 mmol) in DMF (10 ml) was then added to the reaction mixture and allowed to stir overnight at room temperature.

To a solution of Glycine in water, cooled to 0° C., was added triethylamine and di-tert-butyl dicarbonate. The reaction mixture was stirred at room temperature for 2 h. The pH was adjusted to about 6 by progressively adding a 10% w/v aqueous citric acid solution. The combined aqueous layers were extracted with ethyl acetate and the combined organic layers were dried over $Na_2SO_4$ and concentrated under vacuum. The product obtained (200 mg) was added to the previously obtained EDC-activated reaction mixture.

The mixture was adjusted to pH 9 with 10% HCl and concentrated to afford a crude product. The crude product was dissolved in methanol (50 ml) and filtered. The filtrate was slowly dripped into methyl tert-butyl ether (200 ml) at 0° C. and filtered to obtain PP IX-mono-Glycine as a mixture containing mainly the two glycine mono-substituted PP IX compounds.

Mass spectrometry and $^1$H NMR analyses confirmed that PP IX-mono-L-Glycine was obtained as the major product.

Biological Activity

Example 1

In this example, control of the gram-negative bacterial plant pathogen *Pseudomonas syringae* pv. *tabaci* with PP IX and modified PP IX was assessed, with and without chelating agents. Treatments were prepared in Phosphate Buffered Saline (PBS) in 96 well plates at desired concentrations. A bacterial suspension was inoculated into the PBS and incubated at 28° C. in the dark for 30 minutes. After 30 minutes, the 96 well plate was placed under illumination for 1 hour (at 21° C.). Following illumination, bacterial suspensions were serially diluted and 10 μL of each dilution is spread uniformly on Tryptic Soy Agar (TSA) plates and placed in the dark in an incubator at 28° C. for 48 hours. After 48 hours, bacterial colonies were counted, and the results were log transformed (log colony forming units (CFU)/mL). The relative inactivation was determined by taking the difference between log CFU (PBS control) and log CFU (treatments). Sample Illumination was provided by LED lights (Heliospectra RX30) emitting about 1000 μmol/m$^2$/s photosynthetically active radiation (PAR). The results are summarized in Table 1 below.

TABLE 1

Effect of 10 μM PP IX and derivatives on *Pseudomonas syringae*

| Compound | log CFU/ml |
|---|---|
| PBS (control) | 8.7 |
| 10 μM PP IX disodium salt | 7.4 |
| 10 μM (PP IX-mono-DMAE:PP IX-di-DMAE - 50:50) | 8.7 |
| 10 μM (PP IX-mono-DMAE:PP IX-di-DMAE - 20:80) | 5.5 |
| 10 μM PP IX disodium salt + 5 mM NaEDTA | 3.8 |
| 10 μM (PP IX-mono-DMAE:PP IX-di-DMAE - 50:50) + 5 mM NaEDTA | 3.1 |
| 10 μM (PP IX-mono-DMAE:PP IX-di-DMAE - 20:80) + 5 mM NaEDTA | 0.0 |

Example 2

In this example, control of dollar spot fungus (*Sclerotinia homoeocarpa*) with PP IX and modified PP IX was assessed. Treatments were prepared in Phosphate Buffered Saline (PBS) in 24 well plates (in duplicates for light vs. dark incubation) at desired concentrations. Then, a 5 mm diameter plug of a *Sclerotinia homoeocarpa* isolate (3 isolates total tested) was inoculated into the PBS and incubated at 21° C. in the dark for 2 hours. After 2 hours, one of the 24 well plates (with isolates in triplicate) was left in the dark and one 24 well plate was placed under illumination for 1 hour (all at 21% C). Following illumination, fungal plugs were removed from PBS, blotted dry on sterile filter paper and transferred to non-amended Potato Dextrose Agar (PDA). Radial growth of the fungus was monitored daily until the growth of *S. homoeocarpa* reaches the edge of the Petri-dish. Illumination was provided by LED lights emitting about 1000 μmol/m2/s photosynthetically active radiation (PAR). The results are summarized at Tables 2A and 2B below.

TABLE 2A

Results in Dark (no light exposure)

| Treatment[1] | Mean Radial Growth[2,3] | % Inhibition[4] |
|---|---|---|
| PBS (control) | 10.1 | — |
| 31 μM Protoporphyrin IX disodium salt + 0.21% BrijO10:ArlasolveDMI (1:4) | 10.5 | -3.8 |
| 31 μM (PP IX-mono-DMAE:PP IX-di-DMAE - 20:80) + 0.21% BrijO10:ArlasolveDMI (1:4) | 0.0 | 100.0 |
| 31 μM (PP IX-mono-DMAE:PP IX-di-DMAE - 50:50) + 0.21% BrijO10:ArlasolveDMI (1:4) | 0.0 | 100.0 |
| 0.21% BrijO10:ArlasolveDMI (1:4) | 10.3 | -1.6 |

Notes on above table:
[1]Treatments were prepared in Phosphate Buffered Saline (PBS), incubated on shaker (200 rpm) for 2 hours in the dark, then kept in dark for 1 hour with no shaking.
[2]Means were calculated based on 3 fungal isolates replicated 3 times, with 2 measurements per replicate (18 total measurements)
[3]Means represent growth that occurred between 24 and 48 hours of incubation at 21° C.
[4]% Inhibition calculated relative to non-amended control

TABLE 2B

Results in Light (exposed to light for 1 hour)

| Treatment[1] | Mean Radial Growth[2,3] | % Inhibition[4] |
|---|---|---|
| PBS (control) | 10.2 | — |
| 31 μM Protoporphyrin IX disodium salt + 0.21% BrijO10:ArlasolveDMI (1:4) | 0.0 | 100.0 |
| 31 μM (PP IX-mono-DMAE:PP IX-di-DMAE - 20:80) + 0.21% BrijO10:ArlasolveDMI (1:4) | 0.0 | 100.0 |
| 31 μM (PP IX-mono-DMAE:PP IX-di-DMAE - 50:50) + 0.21% BrijO10:ArlasolveDMI (1:4) | 0.0 | 100.0 |
| 0.21% BrijO10:ArlasolveDMI (1:4) | 6.1 | 40.2 |

Notes on above table:
[1]Treatments were prepared in Phosphate Buffered Saline (PBS), incubated on shaker (200 rpm) for 2 hours in the dark, then exposed to light (Helios, 1000 PAR) for 1 hour.
[2]Means were calculated based on 3 fungal isolates replicated 3 times, with 2 measurements per replicate (18 total measurements)
[3]Means represent growth that occurred between 24 and 48 hours of incubation at 21° C.
[4]% Inhibition calculated relative to non-amended control

Example 3

Control of the fungal plant pathogen *Colletotrichum orbiculare* ATC20767 (Cgm) on the host plant *Nicotiana benthamiana* following treatment with modified PP IX compounds was assessed. Treatments were applied to *N. benthamiana* plants approximately 2 h prior to inoculation with a spore suspension of Cgm. Plants were then exposed to light for a 24-hour period followed by dark incubation until disease symptoms were evident on the water treated control plants. Once disease symptoms were evident, lesions were counted, and leaf area measured in order to determine the number of lesions/cm$^2$ leaf area. Four replicate plants were used per treatment and plants were randomized under the light source. Illumination is provided by LED lights emitting about 180 μmol/m$^2$/s photosynthetically active radiation (PAR). The results are shown below.

TABLE 3

Effect of modified PP IX compounds on *Colletotrichum orbiculare*.

| Treatment | % inhibition |
|---|---|
| untreated control | 0 |
| 0.05% (PP IX-mono-DMAE:PP IX-di-DMAE - 20:80) | 93 |

TABLE 3-continued

| Effect of modified PP IX compounds on *Colletotrichum orbiculare*. | |
|---|---|
| Treatment | % inhibition |
| 0.05% (PP IX-mono-DMAE:PP IX-di-DMAE - 50:50) | 89 |
| 0.05% PP IX-mono-$PEG_{600}$ | 56 |
| 0.05% PP IX-mono-L-valine | 50 |
| 0.05% PP IX-mono-glycine | 35 |

All publications, patents, and patent documents cited herein above are incorporated by reference herein, as though individually incorporated by reference. The compounds, compositions, methods and uses described herein have been described with reference to various embodiments and techniques. However, one skilled in the art will understand that many variations and modifications can be made while remaining within the spirit and scope of the appended claims.

The invention claimed is:

1. A method for promoting the health of a plant, the method comprising:

applying to the plant a compound of Formula I:

Formula I 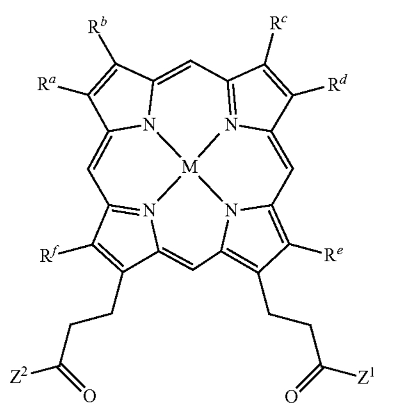 or an agriculturally acceptable salt thereof, wherein:

one of $Z^1$ and $Z^2$ is $OR^1$; and the other one of $Z^1$ and $Z^2$ is $NR^2R^3$, $NR^2—(CH_2)_n—NR^4R^5$, $NR^2—(CH_2)_n—N^+R^4R^5R^6$ $Y^-$, $NR^2—(CH_2)_n—O$ $(PO_3H)—W^+$, $NR^2—(CH_2)_n—Si$ $(R^7)_3$, $NR^2—(CH_2)_n—SR^8$, $NR^2—(CH_2)_n—NR^4—(CH_2)_p—NR^9R^{10}$, $NR^2—(CH_2)_n—NR^4—(CH_2)_p—N^+R^9R^{10}R^{11}$ $Y^-$, $NR^2—(CH_2)_n—NR^4—(CH_2)_p—O(PO_3H)^-W^+$, $NR^2—(CH_2)_n—NR^4—(CH_2)_p—Si(R^7)_3$, $NR^2(CH_2)_n—NR^4—(CH_2)_p—SR^8$, $O(CH_2)_n—NR^4R^5$, $O(CH_2)_n—N^+R^4R^5R^6$ $Y^-$, $O(CH_2)_n—O$ $(PO_3H)^-W^+$, $O(CH_2)_n$-Si $(R^7)_3$, $O(CH_2)_n—SR^8$, $O(CH_2)_n—NR^4—(CH_2)_p—NR^9R^{10}$, $O(CH_2)_n—NR^4—(CH_2)_p—N^+R^9R^{10}R^{11}$ $Y^-$, $O(CH_2)_n—NR^4—(CH_2)_p—O(PO_3H)^-W^+$or $O(CH_2)_n—NR^4—(CH_2)_p—Si$ $(R^7)_3$;

or $Z^1$ is $NR^2R^3$, $NR^2—(CH_2)_n—NR^4R^5$, $NR_2—(CH_2)_n—N^+R^4R^5R^6$ $Y^-$, $NR^2—(CH_2)_n—O(PO_3H)^-W^+$, $NR^2—(CH_2)_n—Si(R^7)_3$, $NR^2—(CH_2)_n—SR^8$, $NR^2—(CH_2)_n—NR^4—(CH_2)_p—NR^9R^{10}$, $NR^2—(CH_2)_n—NR^4—(CH_2)_p—N^+R^9R^{10}R^{11}$ $Y^-$, $NR^2—(CH_2)_n—NR^4—(CH_2)_p—O$ $(PO_3H)^-W^+$, $NR^2—(CH_2)_n—NR^4—(CH_2)_p—Si(R^7)_3$, $NR^2—(CH_2)_n—NR^4—(CH_2)_p—SR^8$, $O(CH_2)_n—NR^4R^5$, $O(CH_2)_n—N^+R^4R^5R^6$ $Y^-$, $O(CH_2)_n—O(PO_3H)^-W^+$, $O(CH_2)_n—Si(R^7)_3$, $O(CH_2)_n$-$SR^8$, $O(CH_2)_n—NR^4—(CH_2)_p—NR^9R^{10}$, $O(CH_2)_n—NR^4—(CH_2)_p—N^+R^9R^{10}R^{11}$ $Y^-$, $O(CH_2)_n—NR^4—(CH_2)_p—O(PO_3H)^-W^+$or $O(CH_2)_n—NR^4—(CH_2)_p—Si(R^7)_3$; and $Z^2$═$Z^1$;

each $R^1$ and $R^2$ is, independently, H, alkyl, substituted alkyl, aryl, substituted aryl, alkenyl, substituted alkenyl, alkynyl or substituted alkynyl;

$R^3$ is alkyl, substituted alkyl, aryl, substituted aryl, alkenyl, substituted alkenyl, alkynyl or substituted alkynyl;

each $R^4$, $R^6$, $R^8$, $R^9$, $R^{10}$ and $R^{11}$ is, independently, H, alkyl, substituted alkyl, aryl, substituted aryl, alkenyl, substituted alkenyl, alkynyl, substituted alkynyl or $—(CH_2)_q—(CH_2CH_2O)_m—R^{13}$;

$R^5$ is alkyl, substituted alkyl, aryl, substituted aryl, alkenyl, substituted alkenyl, alkynyl, substituted alkynyl or $—(CH_2)_q—(CH_2CH_2O)_m—R^{13}$;

$R^7$ is alkyl, O (alkyl) or O (tri-substituted silyl);

$R^{13}$ is H, alkyl, substituted alkyl, aryl, substituted aryl, alkenyl, substituted alkenyl, alkynyl, substituted alkynyl, CO(alkyl), CO(substituted alkyl), CO(alkenyl), CO(substituted alkenyl), CO(alkynyl) or CO(substituted alkynyl);

$W^+$is an agriculturally acceptable cation;

$Y^-$is an agriculturally acceptable anion;

n is an integer selected from 1 to 16;

p is an integer selected from 1 to 16;

m is an integer selected from 1 to 100;

q is an integer selected from 0 to 16;

each $R^a$, $R^b$, $R^c$, $R^d$, $R^e$ and $R^f$ is, independently, H, alkyl, substituted alkyl, aryl, substituted aryl, alkenyl, substituted alkenyl, alkynyl or substituted alkynyl;

====== is a single bond or a double bond;

====== is a single bond or a double bond; and

M is 2H or a metal species, wherein each substituted alkyl, substituted aryl, substituted alkenyl and substituted alkynyl groups are, independently, substituted with one or more OH, F, Cl, Br, I, CN and $N_3$.

2. The method of claim 1, wherein $R^a$, $R^c$, $R^e$ and $R^f$ are methyl; and $R^b$ and $R^d$ are vinyl.

3. The method of claim 1, wherein M is a metal species selected from the group consisting of Mg(II), Zn(II), Pd(II), Sn(IV), Al(III), Pt(II), Si(IV), Ge(IV), Ga(III), In(III), Cu(II), Co(II), Fe(II) and Mn(II).

4. The method of claim 1, wherein:

$R^1$ is H;

$R^2$ is H;

$R^3$ is alkyl;

$R^4$ is H or alkyl;

$R^5$ is alkyl;

$R^6$ is alkyl;

$R^7$ is O (tri-substituted silyl);

$R^8$ is H or alkyl;

$R^9$ is alkyl;

$R^{10}$ is alkyl;

$R^{11}$ is alkyl;

R[13] is H, alkyl, alkenyl, CO (alkyl) or CO (alkenyl);

n is an integer selected from 2 to 4;

p is an integer selected from 2 to 4; and m is an integer selected from 1 to 20.

5. The method of claim 1, wherein:

$Z^1$ is $NR^2R^3$, $NR^2—(CH_2)_n—NR^4R^5$, $NR^2—(CH_2)_n—N^+R^4R^5R^6\ Y^-$, $NR^2—(CH_2)_n—O(PO_3H)^-W^+$, $NR^2—(CH_2)_n—Si(R^7)_3$, $NR^2—(CH_2)_n—SR^8$, $NR^2—(CH_2)_n—NR^4—(CH_2)_p—NR^9R^{10}$, $NR^2—(CH_2)_n—NR^4—(CH_2)_p—N^+R^9R^{10}R^{11}\ Y^-$, $NR^2—(CH_2)_n—NR^4—(CH_2)_p—O(PO_3H)^-W^+$, $NR^2—(CH_2)_n—NR^4—(CH_2)_p—Si(R^7)_3$, $NR^2—(CH_2)_n—NR^4—(CH_2)_p—SR^8$, $O(CH_2)_n—NR^4R^5$, $O(CH_2)_n—N^+R^4R^5R^6\ Y^-$, $O(CH_2)_n—O(PO_3H)^-W^+$, $O(CH_2)_n—Si(R^7)_3$, $O(CH_2)_n—SR^8$, $O(CH_2)_n—NR^4—(CH_2)_p—NR^9R^{10}$, $O(CH_2)_n—NR^4—(CH_2)_p—N^+R^9R^{10}R^{11}\ Y^-$, $O(CH_2)_n—NR^4—(CH_2)_p—O(PO_3H)^-W^+$ or $O(CH_2)_n—NR^4—(CH_2)_p—Si\ (R^7)_3$; and $Z^2=Z^1$.

6. The method of claim 1, wherein:

one of $Z^1$ and $Z^2$ is $NR^2R^3$, $NR^2—(CH_2)_n—NR^4R^5$, $NR^2—(CH_2)_n—N^+R^4R^5R^6\ Y^-$, $NR^2—(CH_2)_n—O(PO_3H)^-W^+$, $NR^2—(CH_2)_n—Si(R^7)_3$, $NR^2—(CH_2)_n—SR^8$ or $NR^2—(CH_2)_n—NR^4—(CH_2)_p—NR^9R^{10}$; and the other one of $Z^1$ and $Z^2$ is $OR^1$.

7. The method of claim 1, wherein:

$Z^1$ is $NR^2R^3$, $NR^2—(CH_2)_n—NR^4R^5$, $NR^2—(CH_2)_n—N^+R^4R^5R^6\ Y^-$, $NR^2—(CH_2)_n—O(PO_3H)^-W^+$, $NR^2—(CH_2)_n—Si(R^7)_3$, $NR^2—(CH_2)_n—SR^8$ or $NR^2—(CH_2)_n—NR^4—(CH_2)_p—NR^9R^{10}$; and $Z^2=Z^1$.

8. The method of claim 1, wherein the compound of Formula I is:

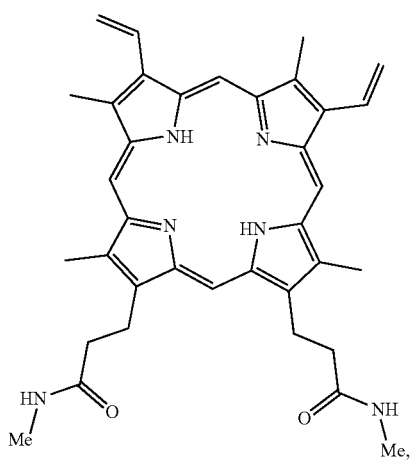

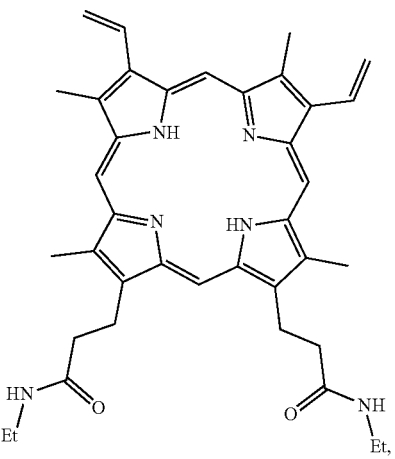

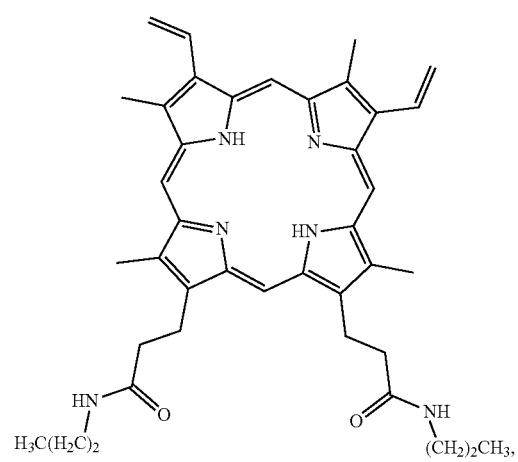

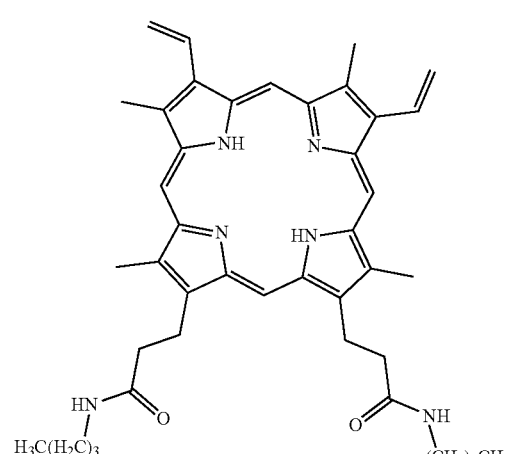

89
-continued
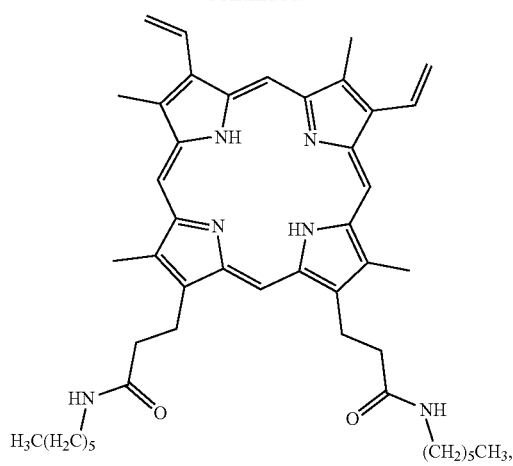
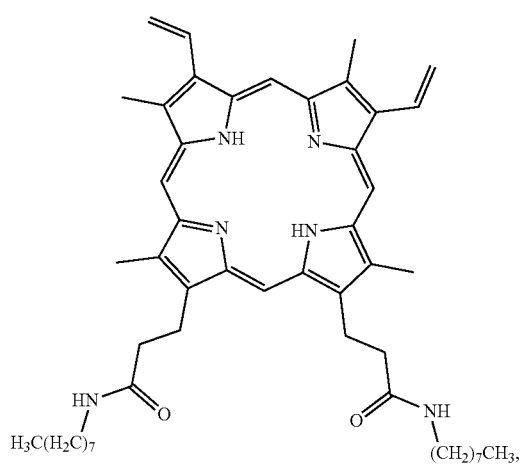
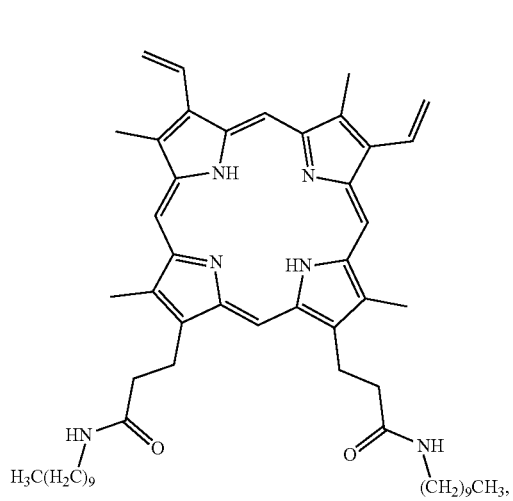
90
-continued
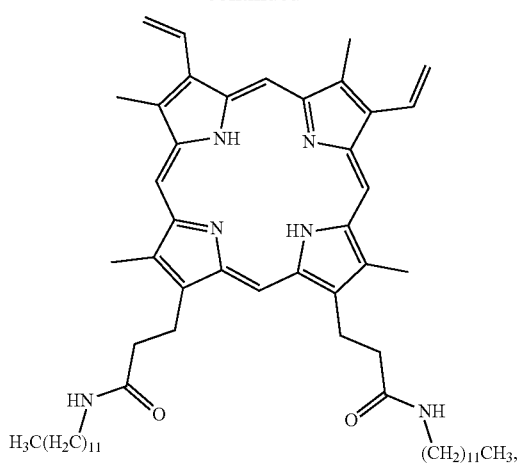
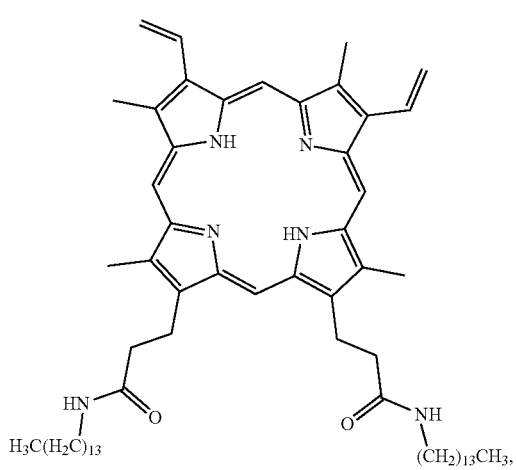
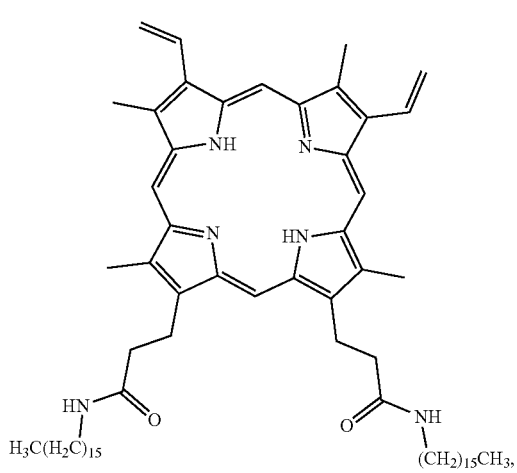

91
-continued
92
-continued
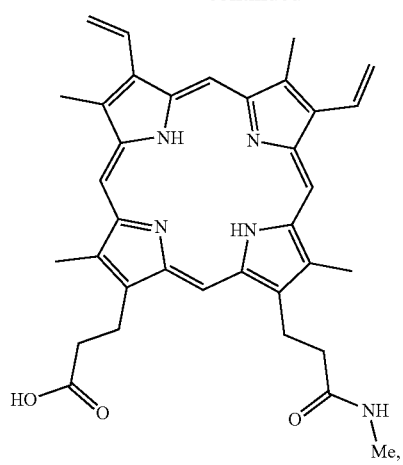
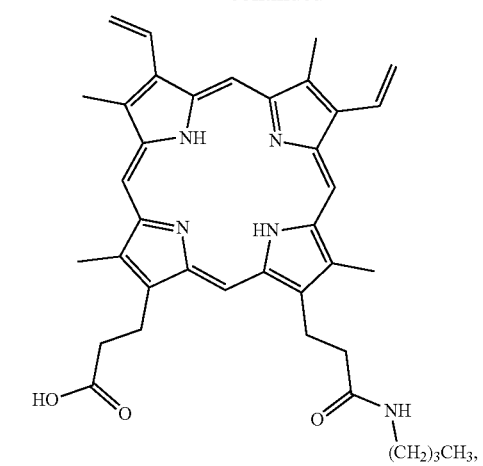
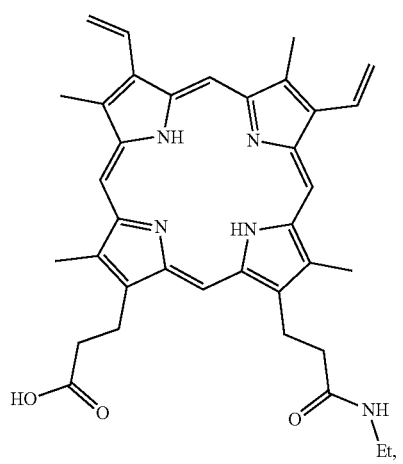
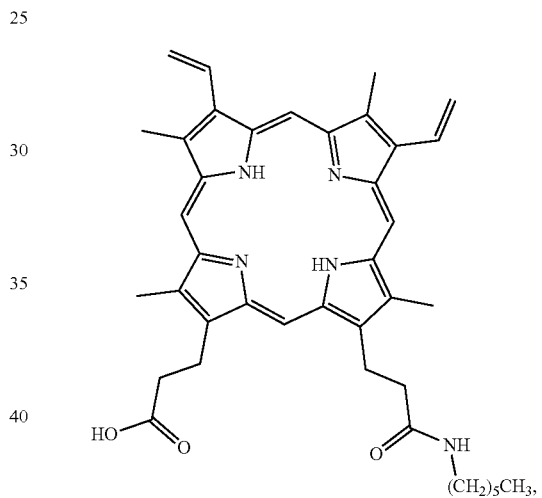
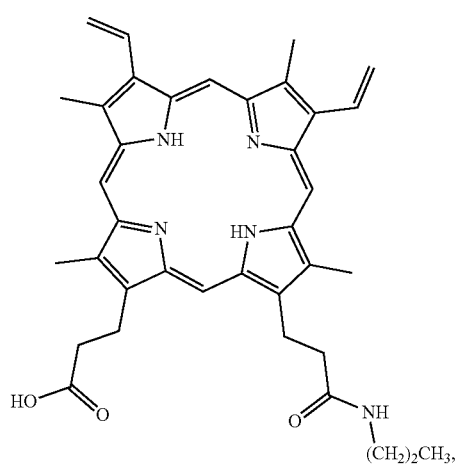
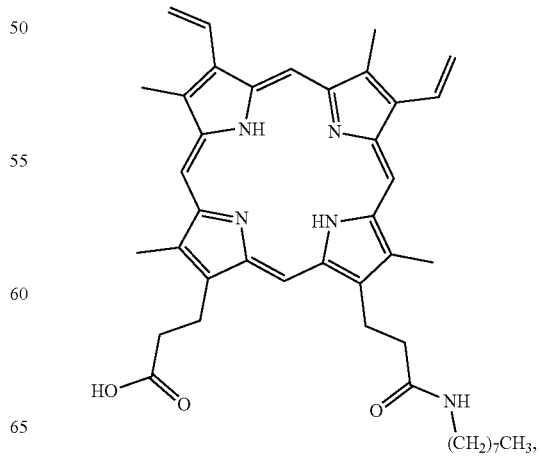

93
-continued
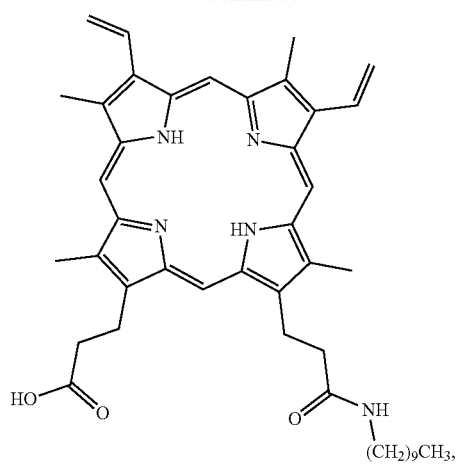
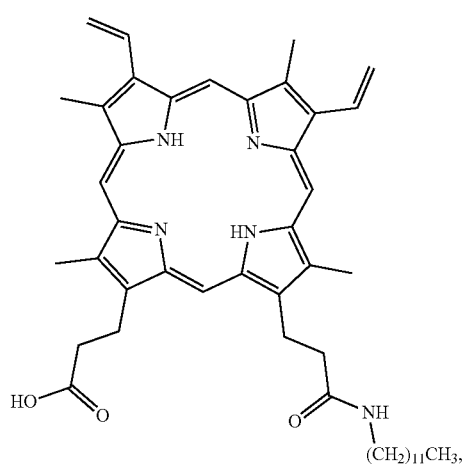
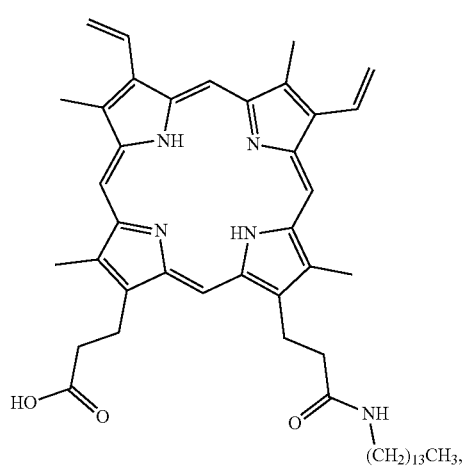
94
-continued
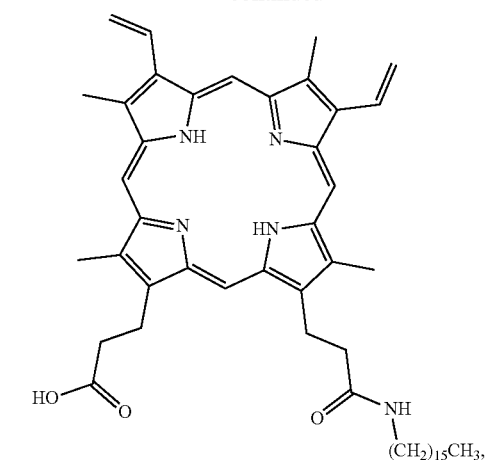
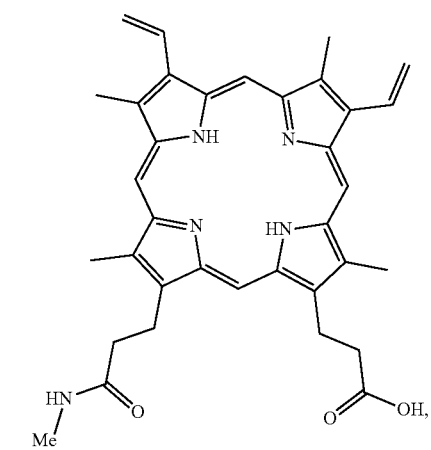
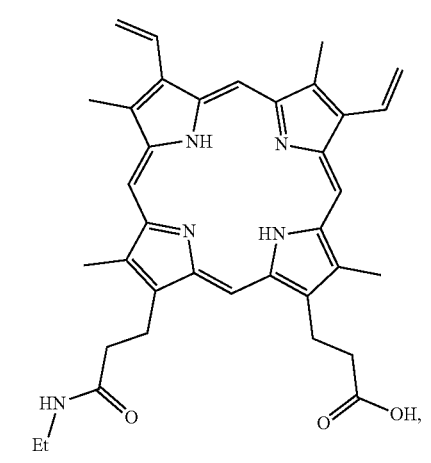

95
-continued
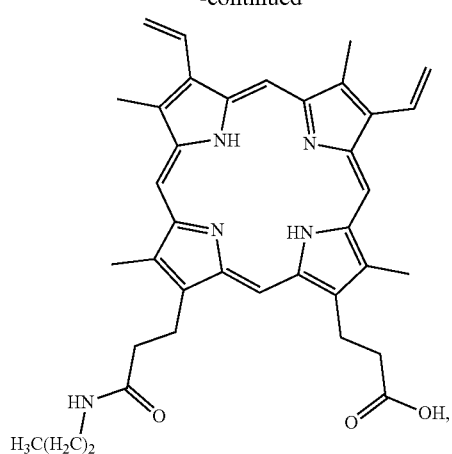
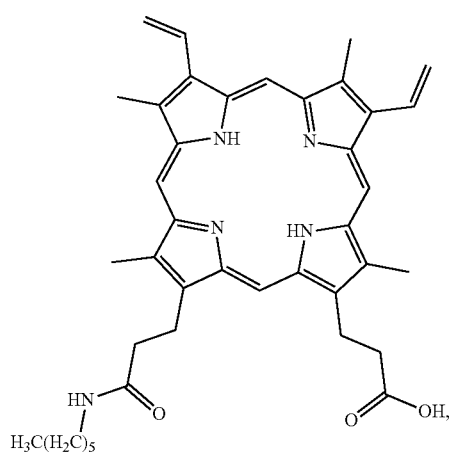
96
-continued
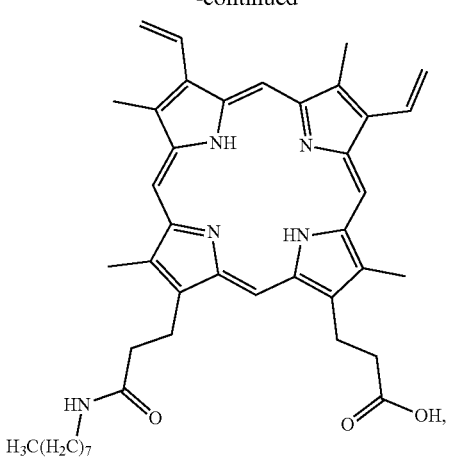
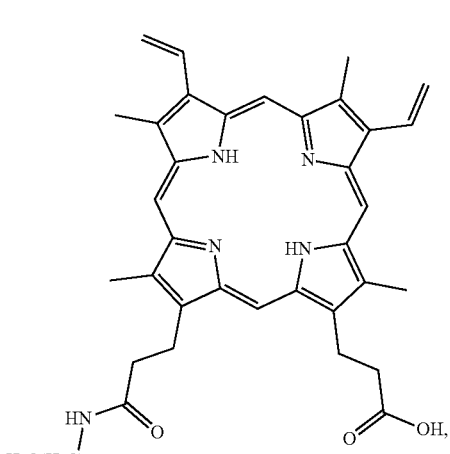

97
-continued
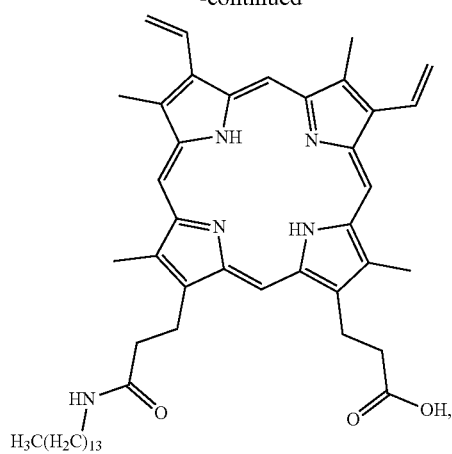
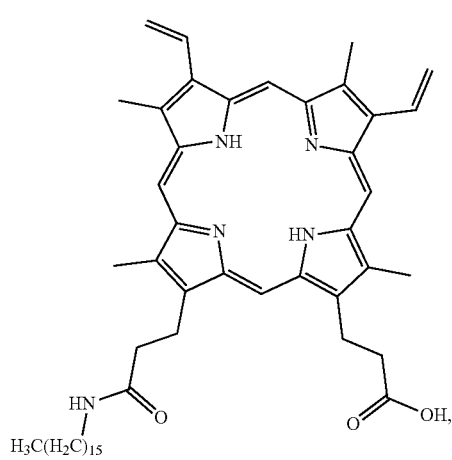
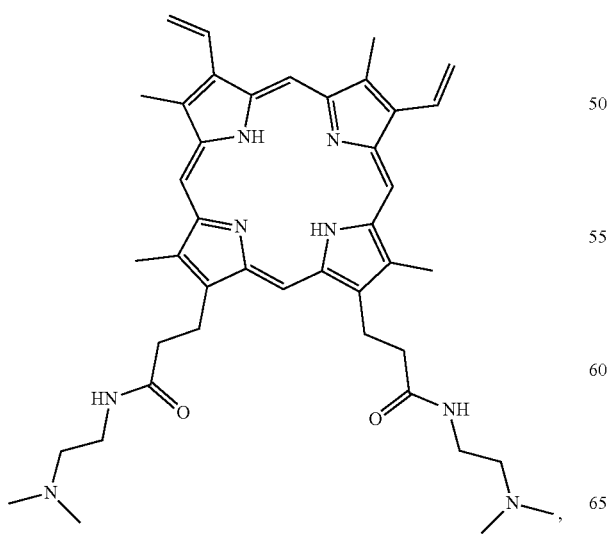
98
-continued
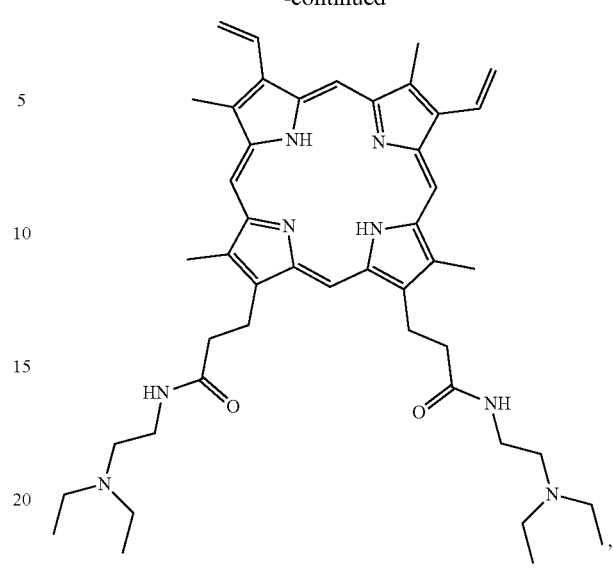
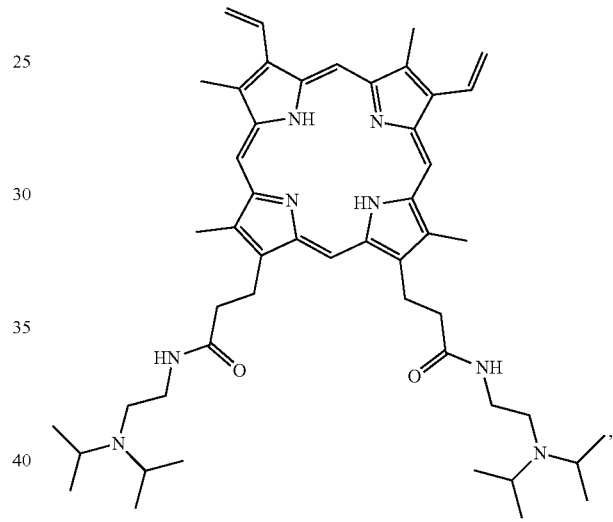
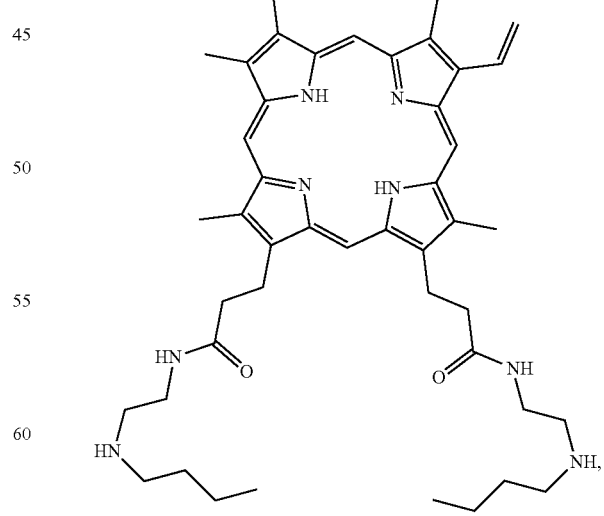

99
-continued
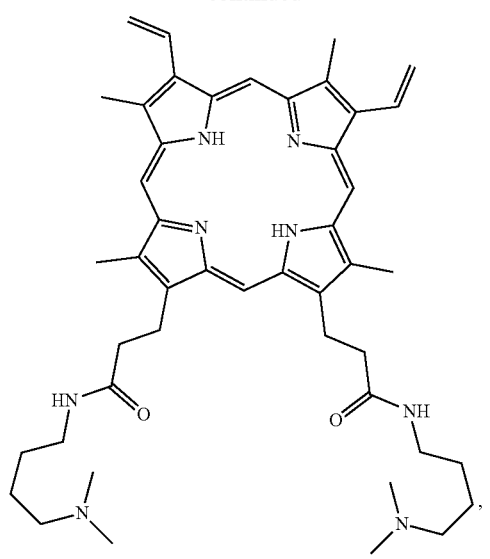
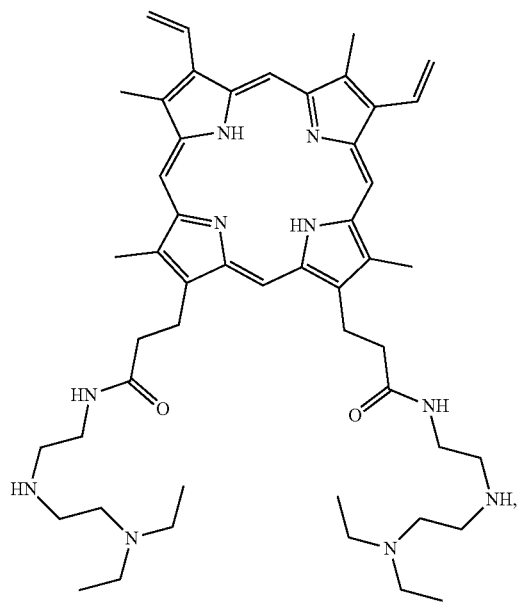
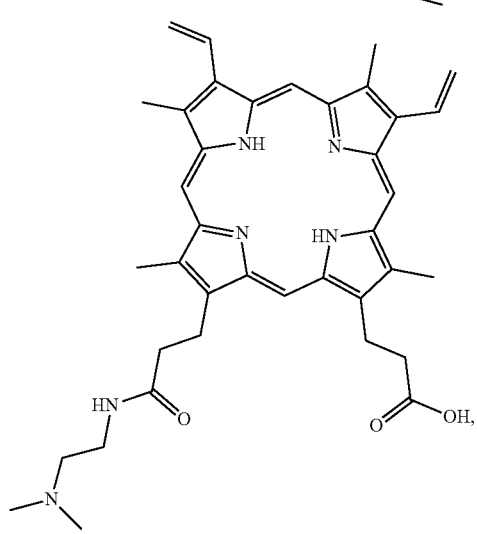
100
-continued
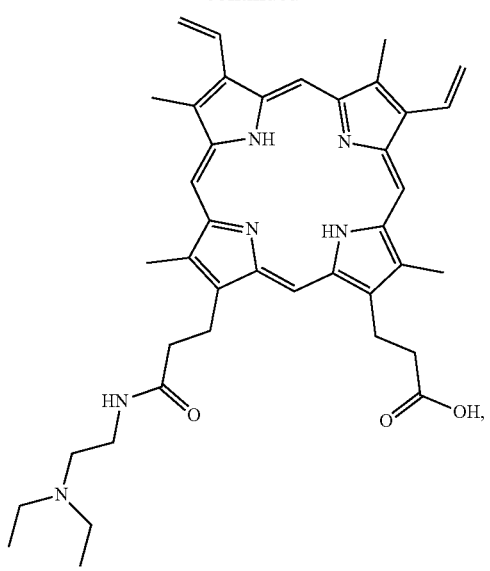
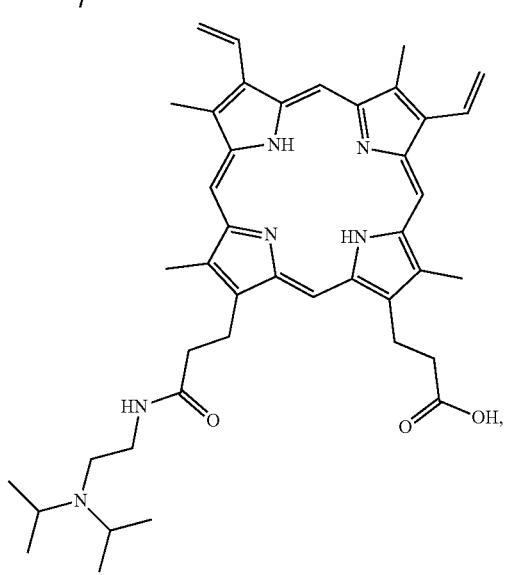

101
-continued
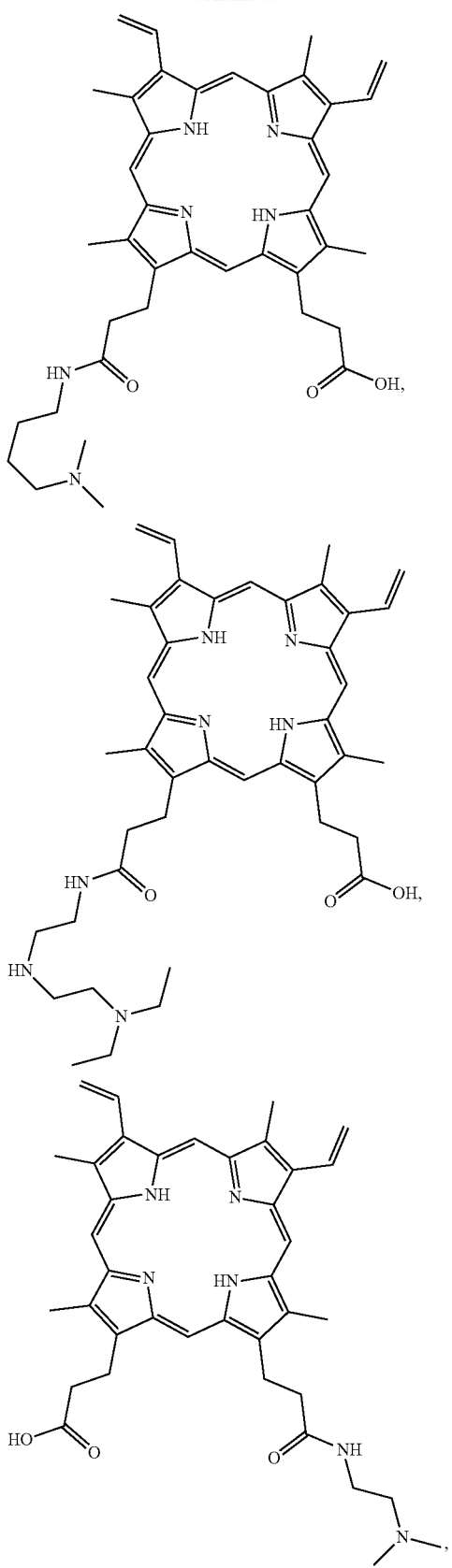
102
-continued
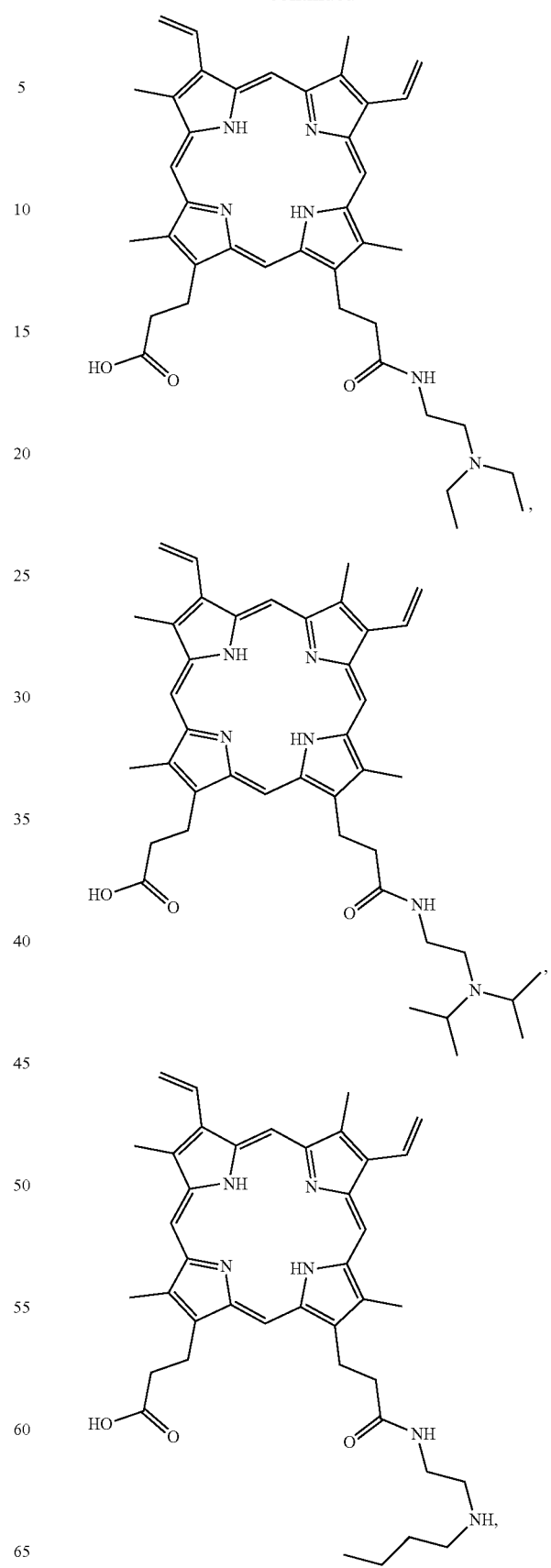

-continued
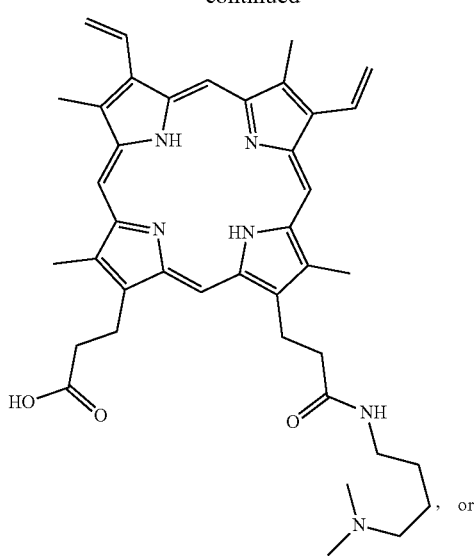
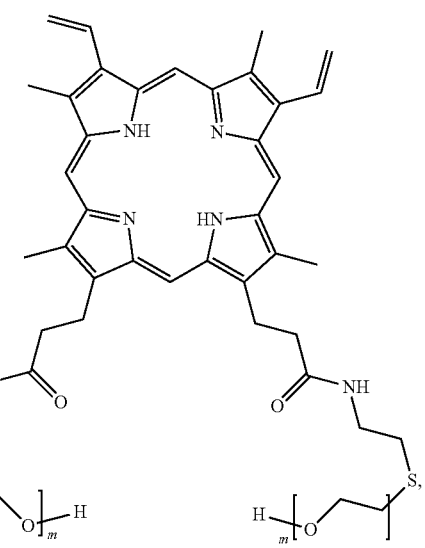
or an agriculturally acceptable salt thereof.
9. The method of claim 1, wherein the compound of Formula I is:
or an agriculturally acceptable salt thereof, wherein m is an integer selected from 4 to 15.
10. The method of claim 1, wherein the compound of Formula I is:

105
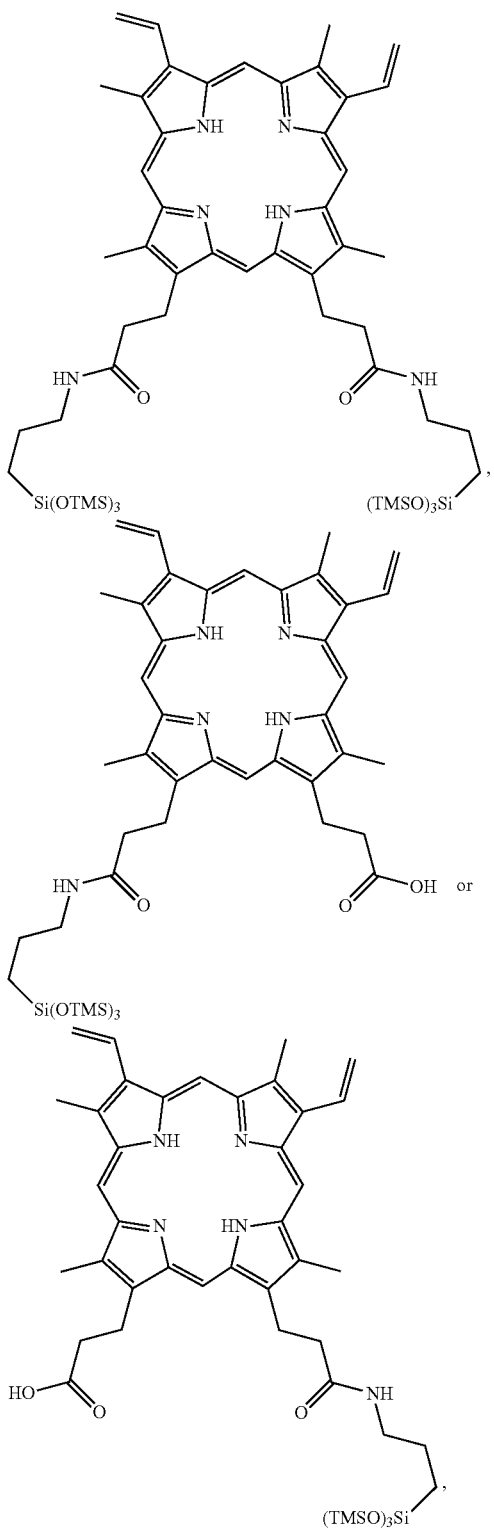
or an agriculturally acceptable salt thereof.
11. The method of claim 1, wherein the compound of Formula I is:
106
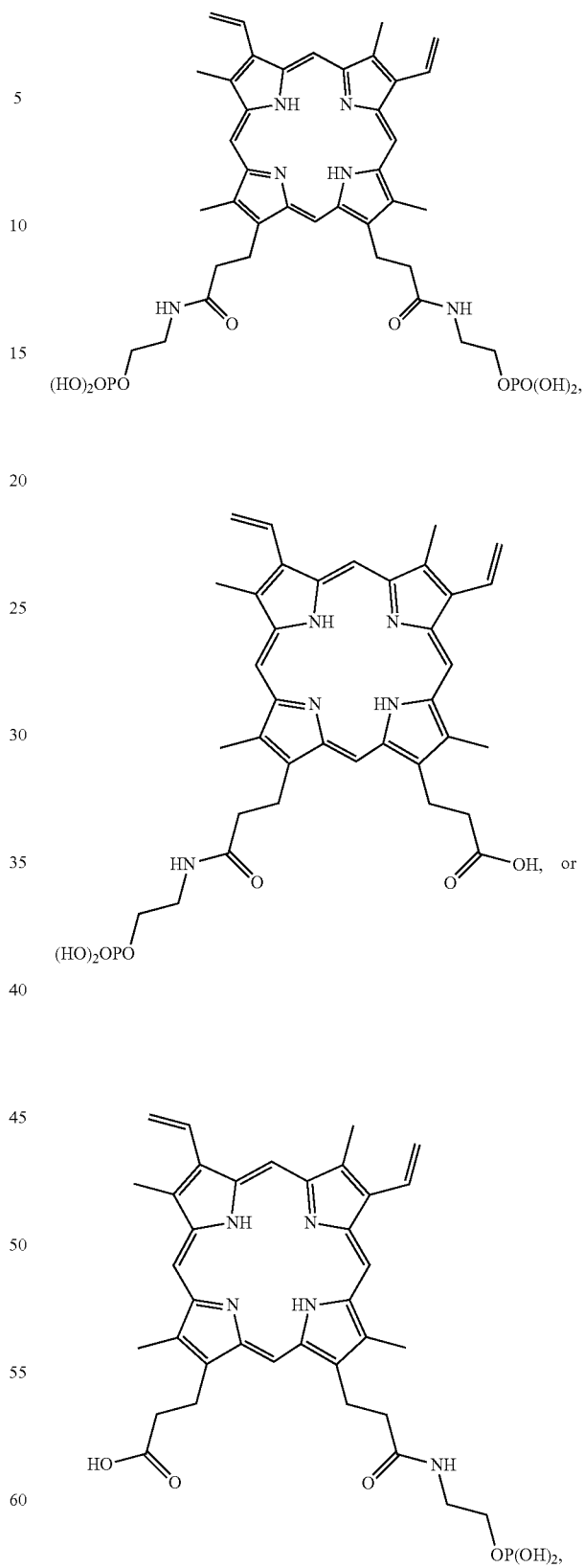
or an agriculturally acceptable salt thereof.
12. The method of claim 1, wherein the compound of Formula I is:

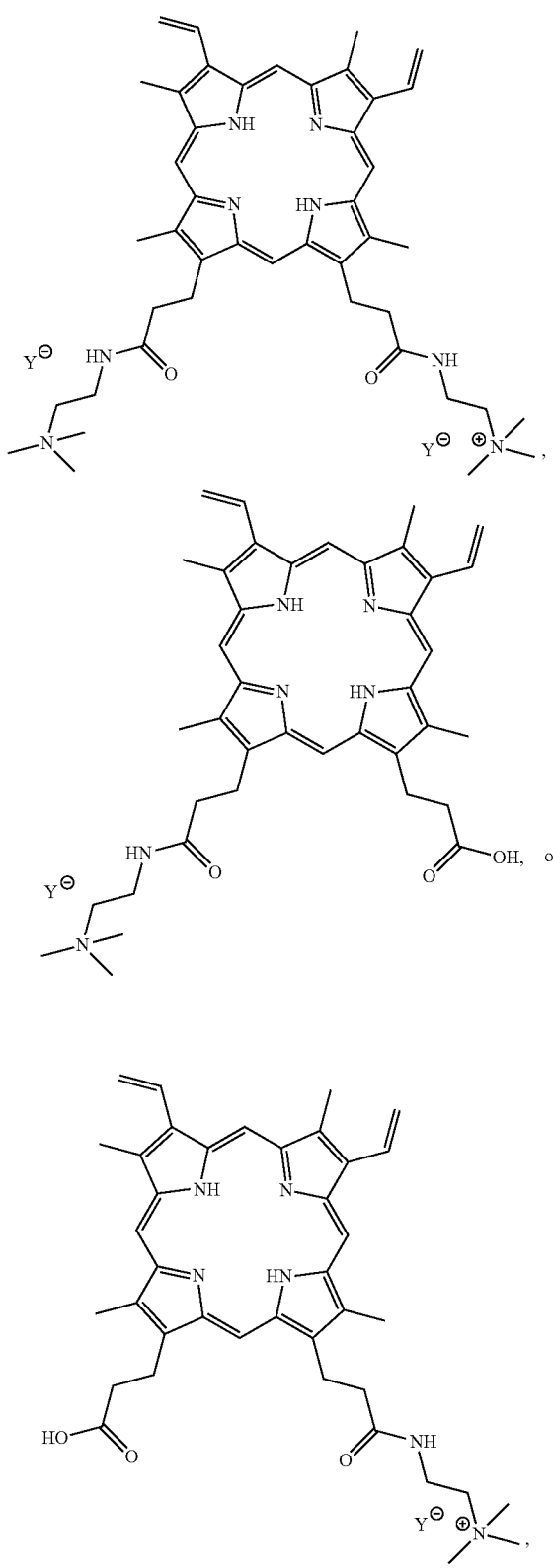

wherein Y⁻ is an agriculturally acceptable anion selected from the group consisting of: chloride, bromide, phosphate, dimethylphosphate, methylsulfate, ethylsulfate, acetate, citrate, tartrate and lactate.

13. A method for promoting the health of a plant, the method comprising:

applying to the plant a compound of Formula I-B1:

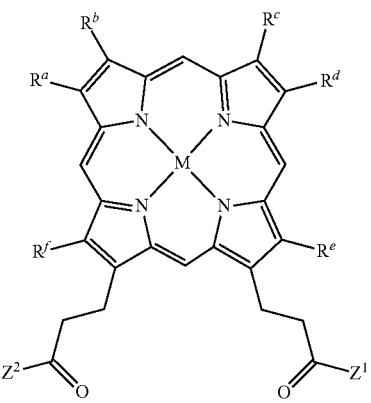

Formula I-B1 or an agriculturally acceptable salt thereof, wherein:

one of $Z^1$ and $Z^2$ is $NR^2$—$(CH_2CH_2O)_m$—$R^{13}$ or O—$(CH_2CH_2O)_m$—$R^{13}$; and the other one of $Z^1$ and $Z^2$ is $OR^1$;

or $Z^1$=$NR^2$—$(CH_2CH_2O)_m$—$R^{13}$ or O—$(CH_2CH_2O)_m$—$R^{13}$; and $Z^2$=$Z^1$;

each $R^1$ and $R^2$ is, independently, H, alkyl or substituted alkyl;

$R^{13}$ is H, alkyl, substituted alkyl, alkenyl, substituted alkenyl, alkynyl, substituted alkynyl, CO(alkyl), CO(substituted alkyl), CO(alkenyl), CO(substituted alkenyl), CO(alkynyl) or CO(substituted alkynyl);

m is an integer selected from 1 to 100;

each $R^a$, $R^b$, $R^c$, $R^d$, $R^e$ and $R^f$ is, independently, H, alkyl, substituted alkyl, alkenyl, substituted alkenyl, alkynyl or substituted alkynyl; and M is 2H or a metal species, wherein the substituted alkyl, substituted alkenyl and substituted alkynyl groups are, independently, substituted with one or more OH, F, Cl, Br, I, CN and N3.

14. The method of claim 13, wherein the compound of Formula I-B1 is:

109
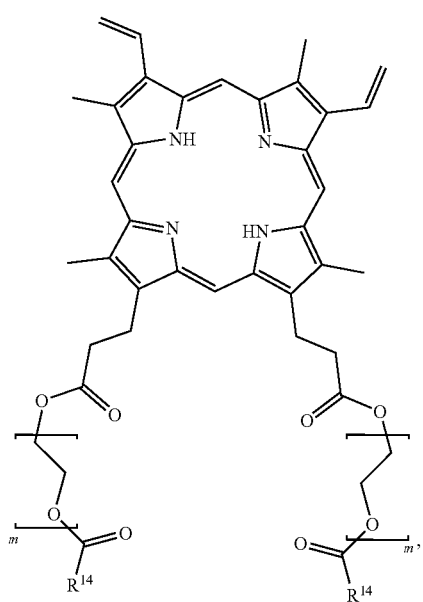
-continued
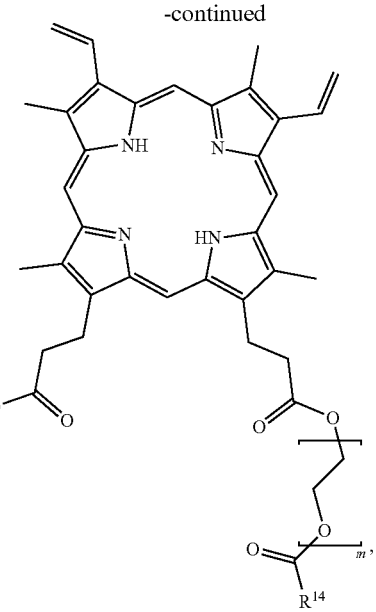
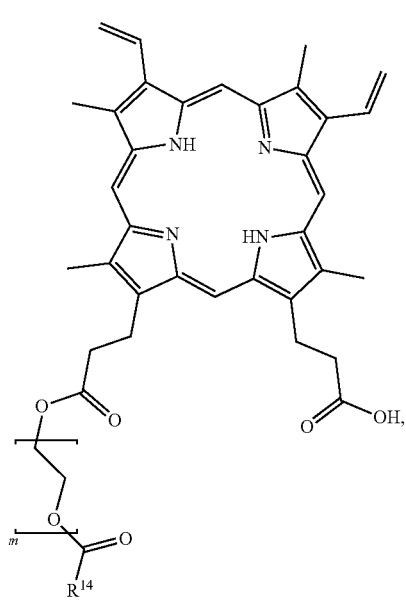
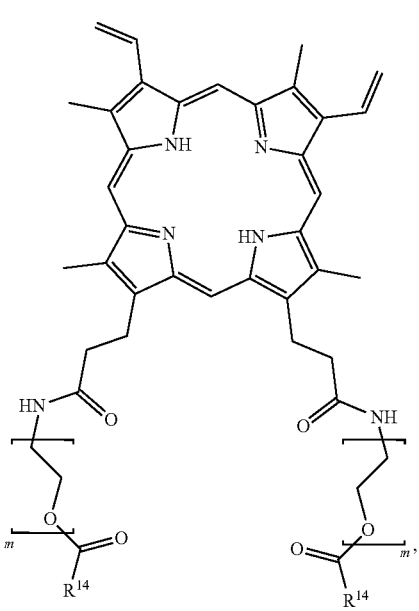

-continued

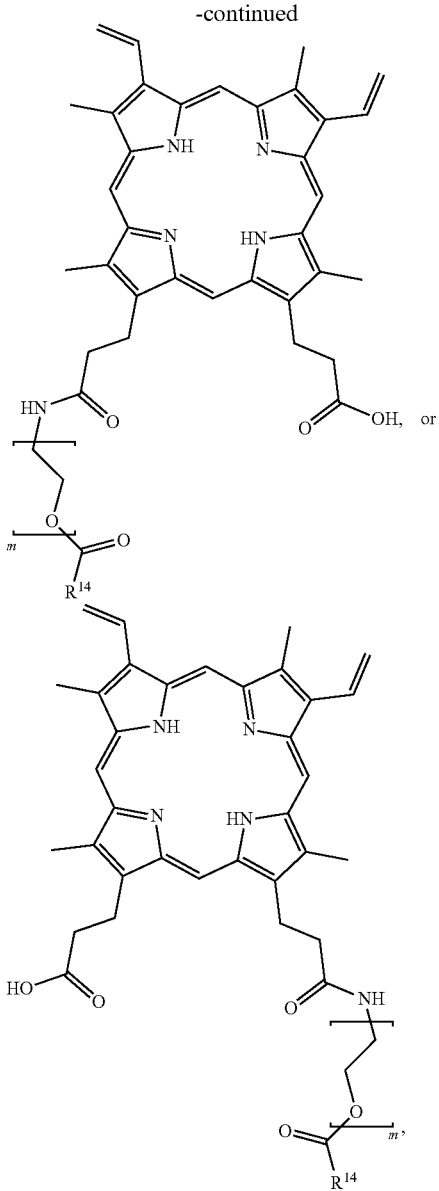

or an agriculturally acceptable salt thereof, wherein m is an integer selected from 1 to 100; and $R^{14}$ is alkyl, alkenyl, alkynyl, substituted alkyl, substituted alkenyl or substituted alkynyl.

15. A method for promoting the health of a plant, the method comprising:
applying to the plant a compound of Formula I-B1:

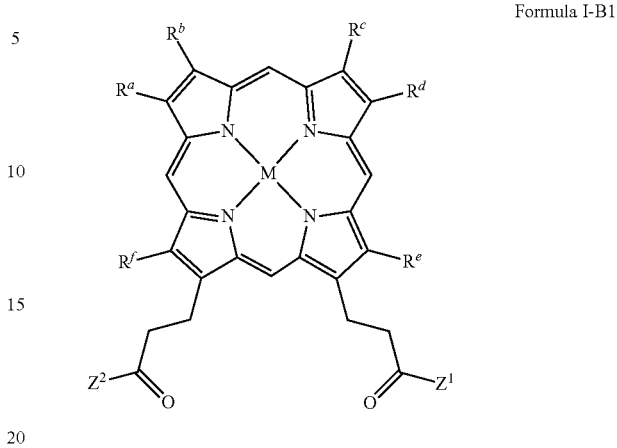

Formula I-B1 or an agriculturally acceptable salt thereof, wherein:
one of $Z^1$ and $Z^2$ is a natural amino acid attached to the compound by its amino group bonded to the alpha carbon; and
the other one of $Z^1$ and $Z^2$ is $OR^1$;
or
$Z^1$ is a natural amino acid attached to the compound by its amino group bonded to the alpha carbon; and
$Z^2=Z^1$;
each $R^1$ and $R^2$ is, independently, H, alkyl or substituted alkyl;
each $R^a$, $R^b$, $R^c$, $R^d$, $R^e$ and $R^f$ is, independently, H, alkyl, substituted alkyl, alkenyl, substituted alkenyl, alkynyl or substituted alkynyl; and
M is 2H or a metal species,
wherein the substituted alkyl, substituted alkenyl and substituted alkynyl groups are, independently, substituted with one or more OH, F, Cl, Br, I, CN and $N_3$.

16. The method of claim 15, wherein:
$Z^1$ is Glycine, L-Alanine, or L-Valine and $Z^2$ is OH;
$Z^2$ is Glycine, L-Alanine, or L-Valine and $Z^1$ is OH; or
$Z^1$ is Glycine, L-Alanine or L-Valine and $Z^2=Z^1$.

17. The method of claim 1, wherein promoting the health of the plant comprises preventing or inhibiting growth of a microbial pathogen of the plant.

18. The method of claim 1, wherein promoting the health of the plant comprises increasing resistance of the plant to one or more abiotic stress.

19. The method of claim 1, wherein promoting the health of the plant comprises controlling insects and insect larvae on the plant.

20. The method of claim 1, wherein the plant is a non-woody crop plant, a woody plant or a turfgrass.

* * * * *